United States Patent [19]

Rosenberg

[11] Patent Number: 5,332,742
[45] Date of Patent: Jul. 26, 1994

[54] RENIN INHIBITORS

[75] Inventor: Saul H. Rosenberg, Libertyville, Ill.

[73] Assignee: Abbott Laboratories, Abbott Park, Ill.

[21] Appl. No.: 147,208

[22] Filed: Nov. 3, 1993

Related U.S. Application Data

[60] Division of Ser. No. 928,190, Aug. 14, 1992, Pat. No. 5,284,849, which is a continuation-in-part of Ser. No. 564,925, Aug. 9, 1990, abandoned, which is a continuation-in-part of Ser. No. 522,349, May 11, 1990, abandoned.

[51] Int. Cl.$^5$ .................. A61K 31/495; A61K 37/00; C07D 417/00
[52] U.S. Cl. ...................... 514/253; 514/19; 514/212; 514/227.8; 514/235.8; 514/236.5; 514/236.8; 514/252; 544/59; 544/60; 544/122; 544/132; 544/137; 544/138; 544/140; 544/158; 544/159; 540/603
[58] Field of Search .................. 514/253, 19; 544/369

[56] References Cited

U.S. PATENT DOCUMENTS 4,845,079  7/1989  Luly et al. .......................... 514/18
4,906,613  3/1990  Watkins et al. .................... 514/16

FOREIGN PATENT DOCUMENTS 309766  4/1989  European Pat. Off. .
311012  4/1989  European Pat. Off. .

Primary Examiner—Cecilia Tsang
Attorney, Agent, or Firm—Steven R. Crowley

[57] ABSTRACT

A renin inhibiting compound of the formula:

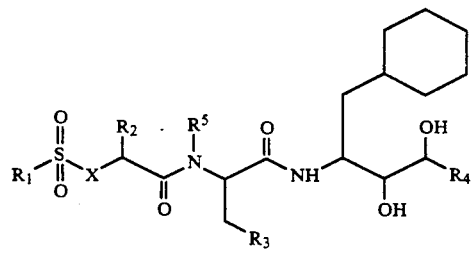

wherein
$R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;
$R_2$ is benzyl, 2-phenylethyl, 1-naphthylmethyl or 2-naphthylmethyl;
$R_3$ is 4-thiazolyl, 2-amino-4-thiazolyl, 2-thiazolyl, 5-thiazolyl, 1-pyrazolyl, 3-pyrazolyl, 1-imidazolyl, n-propyl, isopropyl, $CH_3S$— or $CH_3SCH_2$—;
$R_4$ is isobutyl or cyclopropyl;
$R_5$ is hydrogen or loweralkyl; and
X is $CH_2$ or NH; or a pharmaceutically acceptable salt, ester or prodrug thereof; with the proviso that when X is NH and $R_3$ is 2-amino-4-thiazolyl, then $R_4$ is cyclopropyl.

6 Claims, 1 Drawing Sheet

RENIN INHIBITORS

This is a division of U.S. patent application Ser. No. 07/928,190, filed Aug. 14, 1992 now U.S. Pat. No. 5,284,849, a continuation-in-part of U.S. patent application Ser. No. 564,925, filed Aug. 9, 1990, abandoned, which is a continuation-in-part of U.S. patent application Ser. No. 522,349, filed May 11, 1990, abandoned.

TECHNICAL FIELD

The present invention relates to novel compounds and compositions which inhibit renin, processes for making the compounds and a method of treating hypertension or congestive heart failure, glaucoma, vascular disease, renal failure or psoriasis with a compound of the invention. In addition, the present invention relates to a method for inhibiting a retroviral protease or treating a retroviral infection with a compound of the invention.

BACKGROUND ART

Renin is a proteolytic enzyme synthesized and stored principally in a specific part of the kidney called the juxtaglomerular apparatus. Any of three different physiologic circumstances may cause the release of renin into the circulation; (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme. Recent patents have disclosed novel small peptide renin inhibitors which contain novel dipeptide isosteres as transition state analogs (Szelke, et al., U.S. Pat. No. 4,609,643; Boger, et al., U.S. Pat. No. 4,668,770; Baran, et al., U.S. Pat. No. 4,657,931; Matsueda, et al., U.S. Pat. No. 4,548,926; Luly, et al., U.S. Pat. No. 4,645,759; and Luly, et al.; U.S. Pat. No. 4,680,284).

DISCLOSURE OF THE INVENTION

Figure 1A:
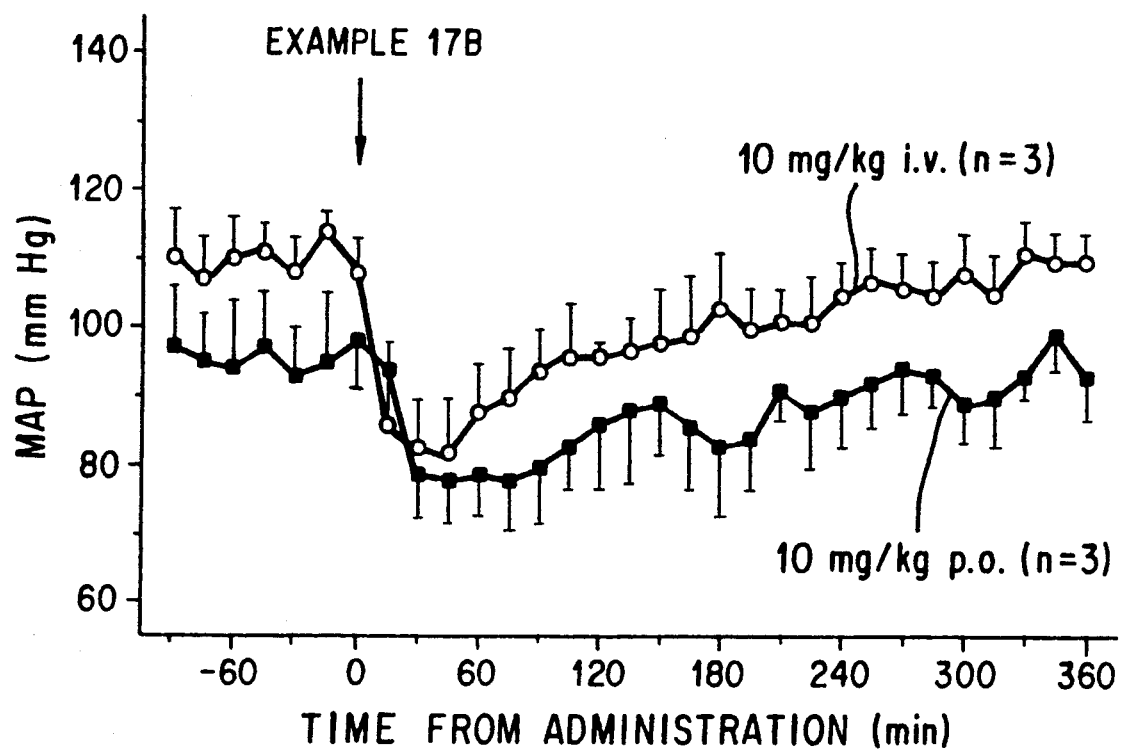
FIGS. 1A and 1B show plots of the average change in mean arterial blood pressure (MLAP) and plasma renin activity (PRA) respectively in salt depleted dogs after oral or i.v. dosing with the compound of Example 17B (monomethanesulfonate salt).

In accordance with the present invention, there are compounds of the formula:

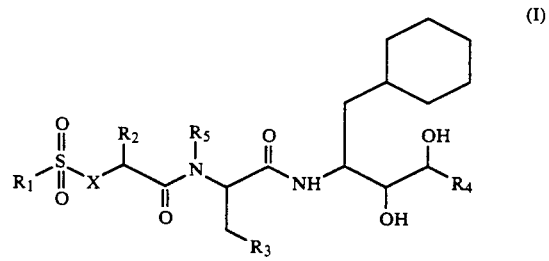

wherein $R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;

$R_2$ is benzyl, 2-phenylethyl, 1-naphthylmethyl or 2-naphthylmethyl;

$R_3$ is 4-thiazolyl, 2-amino-4-thiazolyl, 2-thiazolyl, 5-thiazolyl, 1-pyrazolyl, 3-pyrazolyl, 1-imidazolyl, n-propyl, isopropyl, $CH_3S-$ or $CH_3SCH_2-$;

$R_4$ is isobutyl or cyclopropyl;

$R_5$ is hydrogen or loweralkyl; and

X is $CH_2$ or NH; or a pharmaceutically acceptable salt, ester or prodrug thereof; with the proviso that when X is NH and $R_3$ is 2-amino-4-thiazolyl, then $R_4$ is cyclopropyl.

Preferred compounds of the present invention are compounds of the formula:

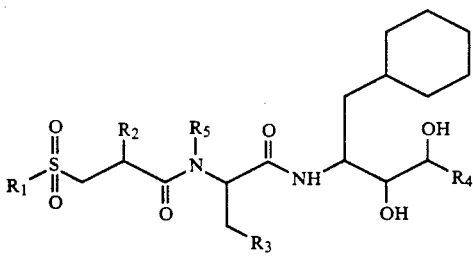

wherein
- $R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;
- $R_2$ is benzyl, 2-phenylethyl, 1-naphthylmethyl or 2-naphthylmethyl;
- $R_3$ is 4-thiazolyl, 2-amino-4-thiazolyl, 2-thiazolyl, 5-thiazolyl, 1-pyrazolyl, 3-pyrazolyl, 1-imidazolyl, n-propyl, isopropyl, CH$_3$S— or CH$_3$SCH$_2$—;
- $R_4$ is isobutyl or cyclopropyl; and
- $R_5$ is hydrogen or loweralkyl; or a pharmaceutically acceptable salt, ester or prodrug thereof.

More preferred compounds of the invention are compounds of the formula:

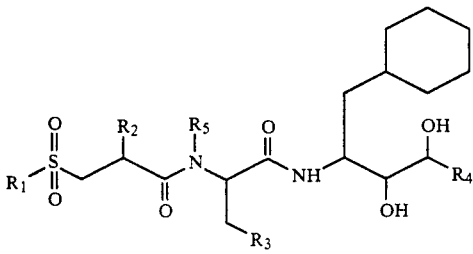

wherein
- $R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;
- $R_2$ is benzyl;
- $R_3$ is 4-thiazolyl or 2-amino-4-thiazoiyl;
- $R_4$ is isobutyl or cyclopropyl; and
- $R_5$ is hydrogen or loweralkyl; or a pharmaceutically acceptable salt, ester or prodrug thereof.

Still more preferred compounds of the invention are compounds of the formula:

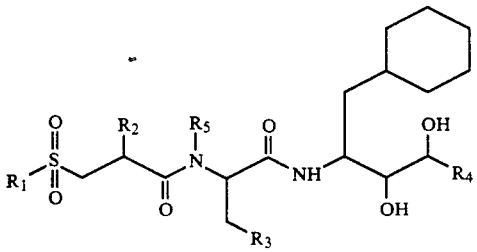

wherein
- $R_1$ is 1-methyl-4-piperazinyl;
- $R_2$ is benzyl;
- $R_3$ is 4-thiazolyl or 2-amino-4-thiazolyl;
- $R_4$ is isobutyl or cyclopropyl; and
- $R_5$ is hydrogen or methyl; or a pharmaceutically acceptable salt, ester or prodrug thereof.

Most preferred compounds of the invention are selected from the group consisting of:

(2S)-2-Benzyl-3-(1-methyl-piperazin-4-ylsulfonyl) propionyl-(L)-(4-Thiazolyl)Ala Amide of (2S, 3R, 4S)-2-Amino-1-cyclohexyl3,4-dihydroxy-6-methylheptane;

2S )-2 -Benzyl-3-(1 -methylpiperazin- 4 -ylsulfonyl)propionyl-(L)-(2-aminothiazol-4-yl) Ala Amide of (2S, 3R, 4S)-2-Amino-1-cyclohexyl-3,4-dihydroxy-6-methylheptane;

(2S )-2-Benzyl-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-4-(cyclopropyl)-butane; and (2S)-2-Benzyl-3-(1-methylpiperazin-4-ylsulfonyl) propionyl-(L)-(2-aminothiazol-4-yl) Ala Amide of (2S,3R,4S)-2-Amino-cyclohexyl-3,4-dihydroxy-4-(cyclopropyl)butane; or a pharmaceutically acceptable salt, ester or prodrug thereof.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

The term "loweralkyl" as used herein refers to straight or branched chain alkyl radicals containing from 1to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "halogen" or "halide" as used herein refers to F, Cl, Br or I.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The terms "alkoxy" and "thioalkoxy" as used herein refer to $R_{30}O—$ and $R_{30}S—$, respectively, wherein $R_{30}$ is a loweralkyl group or benzyl.

The term "haloalkoxy" as used herein refers to $R_{31}O—$ wherein $R_{31}$ is a haloalkyl group.

The term "aminocarbonyl" as used herein refers to —C(O) NH$_2$.

The term "alkylaminocarbonyl" as used herein refers to —C(O)NHR$_{32}$ wherein R$_{32}$ is loweralkyl.

The term "dialkylaminocarbonyl" as used herein refers to —C(O)NR$_{33}$R$_{34}$ wherein R$_{33}$ and R$_{34}$ are independently selected from loweralkyl.

The term "alkoxycarbonyl" as used herein refers to —C(O)OR$_{35}$ wherein R$_{35}$ is loweralkyl.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which hereby incorporated by reference. N-protecting groups comprise carbamates, amides, N- alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl, t-butyloxycarbonyl (Boc), benzyloxycarbonyl (Cbz) and the like. N-protecting groups also include an L- or D-aminoacyl residue, which can itself be N-protected.

The term "Ala", as used herein refers to alanine. general, the amino acid abbreviations follow the IUPAC-IUB joint Commission on Biochemical Nomenclature for amino acids and peptides (Eur. J. Blochem. 1984, 158, 9–31).

The compounds of the invention ($\underline{I}$) can be prepared as shown in Schemes I and II. As shown in Scheme I, carboxylic acid $\underline{1}$, or an activated derivative thereof, ($P_1$ is hydrogen or an N-protecting group, $R_5$ is as defined above and $R_3$ is as defined above (or an N-protected derivative thereof)) can be coupled with amine $\underline{2}$ ($R_4$ is as defined above) using standard peptide coupling methods. Removal of the protecting group $P_1$ from the resulting product provides $\underline{4}$. Amine $\underline{4}$ can then be coupled with carboxylic acid $\underline{3}$, or an activated derivative thereof, ($R_1$ and $R_2$ are defined as above) using standard peptide coupling methods to provide $\underline{I}$.

Alternatively, carboxylic acid $\underline{3}$, or an activated derivative thereof, can be coupled with $\underline{6}$ ($P_2$ is loweralkyl or benzyl). Removal of the protecting group $P_2$ from the resulting product by hydrolysis or hydrogenation provides $\underline{5}$. Carboxylic acid $\underline{5}$, or an activated derivative thereof, can then be coupled with $\underline{2}$ to provide $\underline{I}$.

Scheme II discloses alternative methods for preparing $\underline{I}$ wherein X is NH. Compound $\underline{7}$ ($R_1$ is as defined above and Z is halogen, for example, Cl, or Z is another group suitable for activating the sulfonyl group in a coupling reaction with an amine) is coupled with amine $\underline{8}$ ($P_3$ is loweralkyl or benzyl). Removal of the protecting group $P_3$ from the resulting product by hydrolysis or hydrogenation provides $\underline{9}$. Compound $\underline{9}$ can be coupled with $\underline{4}$ to provide $\underline{I}$.

Alternatively, compound $\underline{7}$ can be coupled with $\underline{10}$ ($P_4$ is loweralkyl or benzyl and $R_3$ is as defined above or an N-protected derivative thereof). Removal of the protecting group $P_4$ from the resulting product by hydrolysis or hydrogenation provides $\underline{5}$. Compound $\underline{5}$ can then be coupled with $\underline{2}$ to provide $\underline{I}$.

Yet another alternative method is disclosed wherein $\underline{7}$ is coupled with $\underline{11}$ ($R_3$ is as defined above or an N-protected derivative thereof) to provide, after removal of the N-protecting group, compound $\underline{I}$.

Activated derivatives of carboxylic acids as mentioned herein include acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimlde derived esters, N-hydroxybenzotriazoie derived esters, N-hydroxy-5-norbornene-2,3-dicarboxamide derived esters, 2,4,5-trichlorophenol derived esters and the like.

SCHEME I

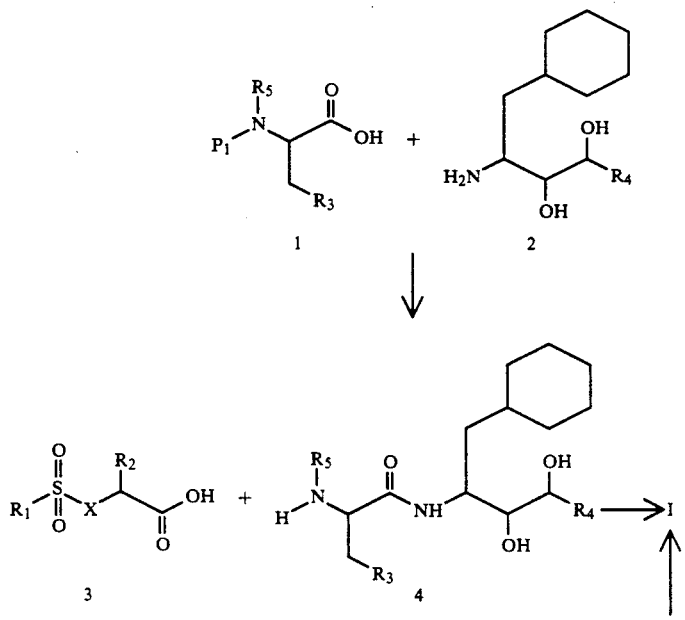

SCHEME I

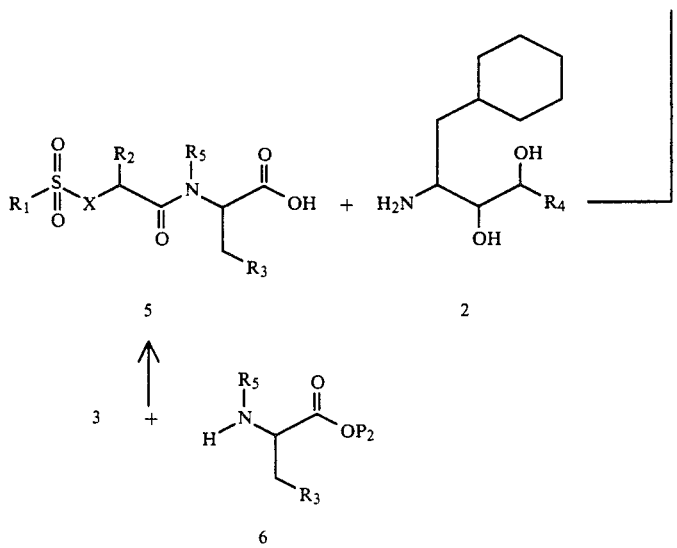

SCHEME II

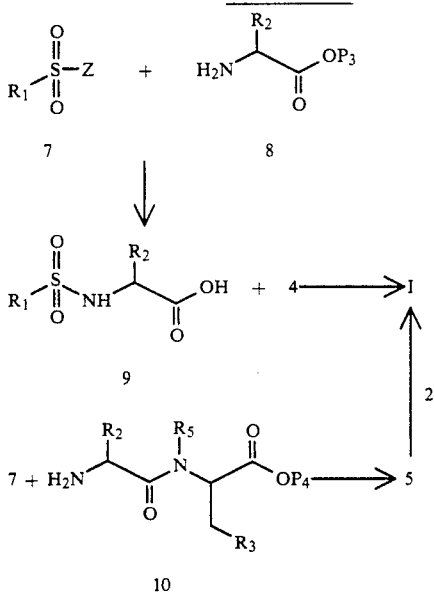

Intermediates useful for the preparation of the novel compounds of this invention include compounds of the formula:

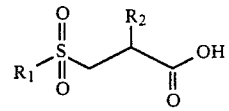

wherein
$R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl; and
$R_2$ is benzyl, 2-phenylethyl, 1-naphthylmethyl or 2-naphthylmethyl; or an acid addition salt thereof; or an activated derivative thereof.

Other compounds which are useful as intermediates for the preparation of the novel compounds of the invention are compounds of the formula:

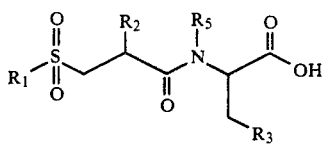

wherein
$R_1$ is 4-piperazinyl, 1-methyl-4-piperazinyl, 1-methyl-1-oxo-4-piperazinyl, 2-oxo-4-piperazinyi, 4-morpholinyl, 4-thiomorpholinyl or 1-methyl-4-homopiperazinyl;
$R_2$ is benzyl, 2-phenylethyl, 1-naphthylmethyl or 2-naphthylmethyl;
$R_3$ is 4-thiazolyl, 2-amino-4-thiazolyl, 2-(N-protected amino)-4-thiazolyl, 2-thiazolyl, 5-thiazolyl, 1-pyrazolyl, 3-pyrazolyl, 1-imidazolyl, n-propyl, isopropyl, $CH_3S$— or $CH_3SCH_2$—; and
$R_5$ is hydrogen or loweralkyl; or an acid addition salt thereof; or an activated derivative thereof.

The following Examples will serve to further illustrate preparation of the novel compounds of the present invention.

EXAMPLE 1

(2S)-2-Benzyl-3-(1-methyl-piperazin-4-ylsulfonyl) propionyl-(L)-(4-Thiazolyl)Ala Amide of (2S,3R,4S)-2-Amino-1-cyclohexyl-3,4-dihydroxy-6-methylheptane

EXAMPLE 1A

Methyl 3-Hydroxy-2-methylene-3-phenylpropionate

A mixture of benzaldehyde (82.1 mL, 0.81 mol), methyl acrylate (109.1 mL, 1.211 mol), 1,4-diazabicyclo(2,2,2)octane (13.6 g, 0.12 mol), and acetic acid (1.4 mL, 0.024 mol) was allowed to stir at 35° C. for 60 h, at which point the reaction was determined to have proceeded to 70% completion by $^1$H NMR. Methyl acrylate (20.9 mL, 0.23 mol) was then added and the solution was allowed to react at 35° C. for an additional 48 h. The mixture was diluted with diethyl ether (1.0 L) and was washed with 2×200 mL portions of a pH 7 phosphate buffer. After concentration in vacuo, the remaining mixture was distilled at reduced pressure (12 mm) to afford 6.5 g of unreacted benzaldehyde and 130.0 g (90%) of the desired product as a colorless oil: b.p. 130° C. (12 mm); IR (film) 1718, 1440 cm$^{-1}$; $^1$H NMR (CDCl$_3$) δ 3.67 (s, 3H), 5.52 (br s, 1H), 5.83–5.85 (m, 1H), 6.29–6.31 (m, 1H), 7.23–7.39 (m, 5H); $^{13}$C NMR (75 MHz, CDCl$_3$) δ 51.8, 72.9, 125.8, 126.5, 127.7, 128.3, 141.2, 141.9, 166.6.

EXAMPLE 1B (Z)-1-Bromo-2-carbomethoxy-3-phenyl-2-propene

To a 2 L, 3-neck Morton flask fitted with a thermometer, a mechanical stirrer, and an addition funnel was added the resultant compound from Example 1A (305.9 g, 1.585 mol) followed by addition of 48% HBr (505 mL, 4.46 mol) in one portion. The flask was immersed in an ice-water bath, at which time concentrated sulfuric acid (460 mL, 8.62 mol) was added dropwise over 90 min and the internal temperature of the reaction mixture was maintained at 23°–27° C. throughout the addition process. After removal of the ice-water bath, the mixture was allowed to stir at ambient temperature overnight. The solution was then transferred to a separatory funnel and the organic layer was allowed to separate from the acid layer. The acids were drained and the organic layer was diluted with 2 L of a 1:1 ethyl acetate/hexane solution, washed with saturated aqueous sodium bicarbonate solution (1 L), dried over sodium sulfate, and concentrated to yield 400 g (99%) of the desired product as a light yellow oil, which was used without any additional purification: b.p. 180° C. (12 mm); IR (film) 1718, 712 cm$^{-1}$; $^1$H NMR (CDCl$_3$) δ 3.89 (s, 3H), 4.40 (s, 2H), 7.38–7.45 (m, 3H), 7.56–7.60 (m, 2H), 7.83 (s, 1H); $^{13}$C NMR (75 MHz, CDCl$_3$) δ 26.77, 52.47, 128.63, 128.87, 129.61, 134.20, 142.95, 166.62.

EXAMPLE 1C (Z)-2-Carbomethoxy-3-phenyl-2-propene-1-sulfonic Acid Sodium Salt To a 12 L, 3-neck round bottom flask fitted with a mechanical stirrer, thermometer and an addition funnel was added the resultant product from Example 1B (400 g, 1.57 mol) and methanol (4 L). The mixture was warmed to 50° C. and a solution of sodium sulfite (199 g, 1.57 mol) dissolved in water (4 L) was added over 75 min while the internal temperature of the flask was maintained at 50° C. After the addition was complete, the clear solution was allowed to stir at 50° C. for an additional 45 min. The reaction mixture in solution was taken to the next step without additional purification. The compound may be isolated by concentration to an amorphous powder, which is contaminated with an equivalent of sodium bromide: IR (KBr) 1711, 1628, 1215 cm$^1$; $^1$H NMR (DMSO D-6) δ 3.70 (s, 3H), 3.77 (s, 2H), 7.33–7.41 (m, 3H), 7.48 (s, 1H), 7.87–7.89 (m, 2H); $^{13}$C NMR (75 MHz, DMSO D-6) δ 49.88, 51.93, 127.36, 128.33, 128.91, 129.82, 134.75, 139.06, 168.60.

EXAMPLE 1D

2-Carbomethoxy-3-phenylpropane-1-sulfonic Acid Sodium Salt

To the 8 L of 1:1 methanol/water mixture containing the resultant compound from Example 1C was added 60 g of W-24 raney nickel. The resulting suspension was pressurized under 50 psi of hydrogen and was allowed to shake on a Parr shaker for 24 h, at which time an additional 20 g of raney nickel catalyst was added. After 6 h under 50 psi of hydrogen, the catalyst was removed by filtration and the solution was concentrated to dryness. To the dry white solid was added ethyl acetate (6 L) and heptane (4 L) and the solution was vigorously stirred with a mechanical stirrer overnight. The white suspension was removed by filtration yielding 530 g (88%) of the desired product as an amorphous powder that was contaminated with approximately one equivalent of NaBr. The compound was used without any additional purification: IR (KBr) 1740, 1215, 1050 cm$^{-1}$. $^1$H NMR (DMSO D-6) δ 2.48–2.54 (m, 1H), 2.74–2.87 (m, 2H), 2.91–3.04 (m, 2H), 3.48 (s, 3H), 7.12–7.32 (m, 5H), $^{13}$C NMR (75 MHz, D$_2$O/DMSO D-6) δ 38.18, 44.80, 52.67, 52.82, 127.42, 129.13, 129.34, 138.14, 176.84.

EXAMPLE 1E

2-Carbomethoxy-3-phenyl-1-propanesulfonyl Chloride

To a 3 L round bottom flask was added the resultant compound from Example 1D (530 g, 1.39 mol) and toluene (520 mL) followed by the addition of PCl$_5$ (317 g, 1.52 mol). The mixture was warmed to 50° C. with stirring for 45 min. It was then diluted with toluene (1 L) and was filtered through celite. After concentration in vacuo, 371 g (96%) of the desired product was obtained as a light brown oil: IR (film); 1740, 1380, 1170 cm$^{-1}$; $^1$H NMR (CDCl$_3$); δ 2.92 (dd, 1H, J=8.1, 14.0), 3.17 (dd, 1H, J=6.6, 14.0), 3.41–3.50 (m, 1H), 3.67 (dd, 1H, J=3.3, 14.3), 3.72 (s, 3H), 4.20 (dd, 1H, J=8.8, 14.3), 7.15–7.18 (m, 2H), 7.25–7.35 (m, 3H); $^{13}$C NMR (75 MHz, CDCl$_3$) δ 37.26, 42.88, 52.65, 64.89, 127.49, 128.87, 128.92, 135.61, 171.79.

EXAMPLE 1F

Methyl 2-Benzyl-3-(1-methyl-piperazin-4-ylsulfonyl)propionate

To a 1 L round bottom flask was added the resultant compound from Example 1E (84.5 g, 0.305 mol) and dichloromethane (305 mL). The mixture was cooled to 0° C. in an ice water bath and a solution of N-methyl piperazine (35.5 mL, 32.1 g) dissolved in dichloromethane (305 mL) was added dropwise with vigorous stirring over 90 min. After the addition was completed, the ice-water bath was removed and the mixture was stirred an additional 4 h while warming to ambient temperature. The solution was then poured into a separatory funnel containing 1 L of a 5% aqueous NaOH solution. The layers were partitioned and the organic layer was dried over potassium carbonate. Concentration in vacuo yielded an oil, which was filtered through 200 g of silica gel using 4:1 hexane/ethyl acetate as an eluant. Concentration gave 84.3 g (81%) of the desired product as a yellow oil: IR (film); 1735, 1165, 955 cm$^{-1}$; $^1$H NMR (CDCl$_3$) δ 2.30 (s, 3H), 2.42 (t, 4H, J=4.8), 2.88 (dd, 1H, J=7.7, 14.0), 2.93 (dd, 1H, J=3.7, 14.0), 3.06 (dd, 1H, J=7.0, 13.6), 3.18-3.27 (m, 5H), 3.43 (dd, 1H, J=8.82, 13.9), 3.67 (s, 3H), 7.14-7.17 (m, 2H), 7.24-7.34 (m, 3H); $^{13}$C NMR (75 MHz, CDCl$_3$) δ 37.91, 42.22, 45.36, 45.83, 49.61, 52.21, 54.36, 127.06, 128.66, 128.92, 129.06, 136.79, 173.33.

EXAMPLE 1G (2S) 2-Benzyl-3-(1-methyl-piperazin-4-ylsulfonyl)propionic Acid

The resultant racemic ester from Example 1F (135 g, 397 mmol) was suspended in acetone (300 mL) and water (900 mL). While being stirred vigorously at a temperature of 35° C., a crude preparation of Subtilisin Carlsberg (10 mL, Alcalase 2.4 L, Novo Laboratories) was added. Sodium hydroxide solution (6 M) was used to maintain the reaction at pH 7.5-8.0. After 3 days, the acetone was removed under reduced pressure and the aqueous phase was extracted with CHCl$_3$ (1 L) to remove the unreacted ester. The aqueous phase was adjusted to pH 7 with 3 M HCl and was desalted by eluting through a column of Amberlite XAD-16 (2 kg, prewashed sequentially with water, methanol, and water) using a water to water/methanol gradient. Evaporation of the solvent afforded 46 g (70%) of a white solid: mp 184.5° C.; TLC (25% ethyl acetate/25% water/25% acetic acid/25% n-butanol) R$_f$=0.43;

Anal. (C$_{15}$H$_{22}$N$_2$O$_4$S.0.25 H$_2$O) Calcd: C, 54.44; H, 6.85; N, 8.47. Found: C, 54.77; H, 6.53; N, 8.39.

EXAMPLE 1H

Diethyl (2-Bromoallyl) acetamidomalonate

To a stirred mixture of diethyl acetamidomalonate (217 g, 1.0 mol) and 2,3-dibromopropene (240 g, 1.2 mol) in dry tetrahydrofuran (2.50 L), under nitrogen, was added sodium hydride (26.4 g, 1.1 mol) in several portions. The reaction mixture was stirred at room temperature for 30 min, then heated to reflux. After heating for 18 h, the resultant slurry was cooled to room temperature and suction filtered through a short pad of silica gel. The solid residue was washed with tetrahydrofuran (2×50 mL), and the filtrates were combined and concentrated. The residue was dissolved in ethyl acetate (2.0 L), washed with water and brine, and then was dried over MgSO$_4$. Filtration and concentration gave a yellow oil which solidified upon drying. The resultant solid was recrystallized from a mixture of hot ethyl acetate/hexane to give 301 g (89%) of the desired product: m.p. 85°-87° C. $^1$H NMR (300 MHz, CDCl$_3$) δ 1.28 (t, J=7.4 Hz, 6H), 2.04 (s, 3H), 3.57 (s, 2H), 4.27 (m, 4H), 5.55 (bs, 1H), 5.61 (bs, 1H), 6.82 (broad, 1H); IR (KBr) 1745, 1635 cm$^{-1}$.

Anal. Calcd. for C$_{12}$H$_{18}$BrNO$_5$: C, 42.87; H, 5.40; Br, 23.77; N, 4.12. Found: C, 43.25; H, 5.56; Br, 22.97; N, 4.12.

EXAMPLE 1I

Diethyl (3-Bromo-2-oxo-propyl)acetamidomalonate

To a cold (0° C.), stirred solution of the resultant compound from Example 1H (280 g, 0.83 mol) in a mixture of 2:1 acetonitrile/water (1.68 L) was added solid N-bromosuccinimide (193 g, 1.08 mol) in three portions over a period of 15 min. The resultant orange mixture was stirred at 0° C. for an additional period of 1 h and then was allowed to warm to room temperature. After 4 h, the reaction mixture was treated with 10% aqueous sodium thiosulfate, diluted with ethyl acetate, and washed sequentially with water, 10% aqueous NaHSO$_4$(3×), water, and brine. Drying (MgSO$_4$) and concentration afforded a yellow solid which was recrystallized from a mixture of ethyl acetate and hexane to give 247 g (85%) of the desired compound as a white solid: m.p. 97°-98.5° C.

$^1$H NMR (300 MHz, CDCl$_3$) δ 1.25 (t, J=7.5 Hz, 6H), 2.01 (s, 3H), 3.87 (s, 2H), 3.93 (s, 2H), 4.25 (q, J=7.5 Hz, 4H), 7.0 (broad, 1H); IR (KBr) 1760, 1732, 1634 and 1209 cm$^{-1}$. Anal. Calcd. for C$_{12}$H$_{18}$BrNO$_6$: C, 40.93; H, 5.15; Br, 22.62; N, 3.98. Found: C, 41.05; H, 5.23; Br, 23.28; N, 3.93.

EXAMPLE 1J

Diethyl (4-Thiazolylmethyl)acetamidomalonate

A 5 L, 3-neck round bottom flask equipped with a mechanical stirrer, stopper and a drying tube was charged with the resultant compound from Example 1 (325 g, 0.92 mol) and flushed witch nitrogen. A freshly prepared solution of thioformamide in tetrahydrofuran (0.8 M, 1.25 L) was added in one portion. The reaction mixture was stirred at room temperature for 4 h. The resultant slurry was then diluted with ether (1.25 L) and cooled to 0° C. The solid was then collected by suction filtration and washed with cold ether (3×) to give the title compound as the hydrobromide salt. This material was transferred to a 4 L separatory funnel, slurried with ethyl acetate (2 L) and basified by the careful addit ion of 2 M aqueous NaOH. The organic layer was separated, washed with water and brine, and then dried over MgSO$_4$. Filtration and concentration afforded a pale yellow oil which solidified upon drying to give 242 g of the desired compound. This material was recrystallized from an ethyl acetate/hexane mixture to afford 185.6 g (64%) of pure material: m.p. 104°-106° C. Anal. Calcd. for C$_{13}$H$_{18}$N$_2$O$_5$S: C, 49.67; H, 5.77; N, 8.91; S, 10.20. Found: C, 49.90; H, 5.72; N, 8.97; S, 10.29.

EXAMPLE 1K

N-Acetyl-3-(4-thiazolyl)-DL-alanine Ethyl Ester

To a stirred solution of the resultant compound from Example 1J (185.6 g, 0.59 mol) in a mixture of tetrahydrofuran (620 mL) and ethanol (310 mL) was added aqueous 2 M LiOH (325 mL, 0.65 mol) dropwise over 20 min. After stirring at room temperature for 2.5 h, reaction mixture was concentrated and the resultant aqueous mixture was extracted with ether (3×200 mL), adjusted to pH 3 with 3 M HCl, and concentrated under reduced pressure. Residual water was removed by evaporating portions of toluene (2×200 mL). The residue was diluted with toluene (1.5 L) and the resultant slurry was heated to reflux with separation of residual water (Dean-Stark trap). After 3 h the reaction mixture was cooled to room temperature, diluted with ethyl acetate (1.5 L) and suction filtered through SiO$_2$ (60 g). The solids were washed with additional ethyl acetate (4×500 mL) and the combined organics were concentrated to afford a pale yellow oil which solidified on drying (0.5 torr) to afford 119.6 g (84%) of the desired compound: m.p. 58°-62° C.

EXAMPLE 1L

N-Acetyl-3-(4-thiazolyl)-L-alanine and N-Acetyl-3-(4-thiazolyl)-D-alanine Ethyl Ester A 5 L, 3-neck round bottom flask equipped with a mechanical stirrer was charged with the resultant compound from Example 1K (210 g, 0.87 mol), distilled water (1.6 L), and 1 M aqueous KCl (0.8 L). The homogeneous solution was adjusted to pH 7.0 with 0.1 M NaOH and then was treated with Subtilisin Carlsberg (1.8 g) dissolved in 0.1 M aqueous KCl (25 mL). The reaction mixture was stirred at room temperature with 1.0 M NaOH added as required to maintain the pH at 6.25-7.25. After 4 h, 430 mL of base had been consumed and the reaction was judged to be complete. The react ion mixture was then extracted with chloroform (4×1.5 L), the aqueous phase was carefully acidified to pH 4 with 2 M HCL and then was concentrated under reduced pressure. Residual water was removed by consecutive evaporation from toluene (3×500 mL) and ethanol (3×500 mL). The residue was taken up in warm ethanol and suction filtered to remove inorganic salts. The solids were washed with warm ethanol (3×400 mL) and the filtrates were concentrated to afford 92.6 g (50%) of N-acetyl-3-(4-thiazolyl)-L-alanine as a white solid: m.p. 186° C.

The combined chloroform fractions from the extractions were washed with saturated aqueous NaHCO$_3$, water, and brine and then were dried over MgSO$_4$. Filtration and concentration gave 103 g (49%) of N-acetyl-3-(4-thiazolyl)-D-alanine ethyl ester. This material could be further purified by recrystallization from ethyl acetate/hexane: m.p. 79°-80.5° C.

EXAMPLE 1M

Epimerization of N-Acetyl-3-(4-thiazolyl)-D-alanine Ethyl Ester

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 1L (102 g, 0.42 mol) was added. The reaction mixture was then heated to reflux. After 3 h the solution was cooled to room temperature, quenched with glacial acetic acid (0.045 mol) and concentrated to remove ethanol. The residue was diluted with ethyl acetate, washed with water and brine and dried over MgSO$_4$. Filtration and concentration gave a yellow oil which was purified by recrystallizing from a mixture of hot ethyl acetate and hexane to yield 89 g (87%) of material identical to that obtained from Example 1K.

EXAMPLE 1N 3-(4-Thiazolyl)-L-alanine Dihydrochloride

A 2 L round bottom flask equipped with a magnetic stirrer was charged with N-acetyl-3-(4-thialzoyl)-L-alanine from Example 1L (92.6 g, 0.43 mol) and 6 M HCl (1 L). The resultant solution was heated to reflux. After 3 h the mixture was allowed to cool to room temperature. The solution was then concentrated under reduced pressure, evaporated from toluene (3×200 mL), and dried under vacuum overnight to give 120 g of a slightly wet solid. This material was used in the next reaction without further purification.

EXAMPLE 1O

N-Boc-3-(4-thiazolyl)-L-alanine

A 4 L Erlenmeyer flask equipped with a mechanical stirrer was charged with the resultant compound from Example 1N (125.9 g) and tetrahydrofuran (1.5 L) and the mixture was adjusted to pH 6.6 with saturated aqueous sodium bicarbonate. The resultant solution was then adjusted to pH 8.9 with 3.0 M NaOH and a solution of di-tert-butyldicarbonate (117.8 g, 0.51 mol) in tetrahydrofuran (150 mL) was added. The reaction mixture was vigorously stirred at room temperature for 40 h. The tetrahydrofuran was removed under vacuum, the pH of the residue was adjusted to 2.0 with 3.0 M HCl and the mixture was extracted with ethyl acetate (3×300 mL). The combined extracts were dried over MgSO$_4$, filtered, and concentrated to give 150 g of a white solid. Recrystallization from hot 1:1 ethyl acetate/hexane (1.06 L) gave 107.6 g (82% from the resultant compound of Example 1L) of the desired compound: m.p. 115° C.; []D = +129.8 (c=1.04, CHCl$_3$).

Anal. Calcd. for C$_{11}$H$_{16}$N$_2$O$_2$: C, 48.53; H, 5.88; N, 10.29. Found: C, 48.58; H, 5.91; N, 10.17.

EXAMPLE 1P

Boc-L-(4-Thiazolyl) Ala Amide of (2S, 3R, 4S)-2-Amino- 1-cyclohexyl-3,4-dihydroxy-6-methylheptane (2S, 3R, 4S)-2- [(tert-Butyloxycarbonyl)amino]-1-cyclohexyl-3,4-dihydroxy-6-methylheptane (5.05 g, 14.7 mmol, Luly et al., *J. Org. Chem.* 1988, 53, 6109) was stirred for 90 min in 4 M HCl in ethanol and then evaporated. Ether was added and evaporated 3 times and the residue was dried under high vacuum. To this residue was added 1-hydroxybenzotriazole (5.57 g, 41.2 mmol), the resultant acid from Example 1 O (4.00 g, 14.7 mmol), dimethylformamide (60 mL) and N-methylmorpholine (3.40 mL, 30.9 mmol). The mixture was cooled to −23° C., treated with 1-(3-dimethylaminopropyl)-3-ethylcarbodiimide hydrochloride (4.03 g, 21.0 mmol). After 2 h at −23° C. and 21 h at ambient temperature the mixture was poured into saturated NaHCO$_3$ solution and extracted into ethyl acetate. The organic layer was washed with water and brine, then dried over Na$_2$SO$_4$ and evaporated to a white solid which was recrystallized from 1:15 (v/v) methylene chloride/ether (multiple crops) affording 6.28 g (86%) of the desired product as a flaky white solid: m.p. 159°-160° C.; TLC (15% CH$_3$OH/85% CHCl$_3$) R$_f$=0.63; $^1$H NMR (CDCl$_3$) δ 8.78 (1H, d), 7.14 (1H, d), 6.18 (2H, br d), 4.44 (1H, dd), 4.27 (1H, m), 4.10 (1H, m), 3.37 (1H, dd), 3.30-3.12 (3H, m), 1.89 (1H, septet), 1.46 (9H, s), 0.94 (3H, d), 0.88 (3H, d).

Anal. Calcd. for C$_{25}$H$_{43}$N$_3$O$_5$S: C, 60.33; H, 8.71; N, 8.44. Found: C, 60.43; H, 8.68; N, 8.51.

EXAMPLE 1Q

H-L-(4-Thiazolyl)Ala Amide of (2S, 3R, 4S)-2-Amino-1-cyclohexyl-3,4-dihydroxy-6-methylheptane Trifluoroacetic acid (50 mL) was slowly added via cannula to a solution of the resultant compound from Example 1P (6.27 g, 12.6 mmol) in methylene chloride (50 mL) at 0° C. The reaction was stirred 3 h at 0° C. and concentrated in vacuo (40° C. bath) to an oil which was basified to pH 10-11 with aqueous $K_2CO_3$. The product was extracted into chloroform, dried over $Na_2SO_4$, filtered, and concentrated to a foam. Recrystallization from 1:4 (v/v) methylene chloride/hexane gave 5.00 g (100%) of the desired product as a fluffy white solid: m.p. 111°-112° C.; TLC (15% $CH_3OH$/85% $CHCl_3$) $R_f=0.46$; $^1H$ NMR ($CDCl_3$) δ 8.77 (1H, d), 7.40 (1H, br d), 7.13 (1H, d), 4.54 (1H, m), 4.25 (1H, m), 3.80 (1H, dd), 3.33 (1H, dd), 3.25-3.12 (3H, m), 0.95 (3H, d), 0.86 (3H, d).

Anal. Calcd. for $C_{20}H_{35}N_3O_3S$: C, 60.42; H, 8.87; N, 10.57. Found: C, 60.05; H, 8.65; N, 10.42.

EXAMPLE 1R (2S)-2-Benzyl-3-(1-methylpiperazin-4-ylsulfonyl)propionyl-(L)-(4-Thiazolyl) Ala Amide of (2S,3R,4S)-2-Amino-1-cyclohexyl-3,4-dihydroxy-6-methylheptane To the resultant acid from Example 1G (1.000 g, 3.064 mmol), the resultant amine from Example 1Q (1.110 g, 2.792 mmol), and 1-hydroxybenzotriazole (1.022 g, 7.563 mmol) in dimethylformamide (20 mL) was added N-methylmorpholine (0.35 mL, 3.2 mmol). The mixture was cooled to −23° C. and treated with 1-(3-dimethylaminopropyl)-3-ethylcarbodiimide hydrochloride (0.760 g, 3.96 mmol). After 2 h at −23° C. and 14 h at ambient temperature, the reaction was poured into saturated $NaHCO_3$ solution (100 mL) and extracted into ethyl acetate (2×50 mL) which was washed with water (2×50 mL) and brine (50 mL) and then was dried over $Na_2SO_4$ and evaporated to afford 1.94 g.

Recrystallization from ethanol (15 mL)/hexane (90 mL) afforded 1.559 (79%) of a white solid: m.p. 169°-170° C.; TLC (10% $CH_3OH$/90% $CHCl_3$) Rf=0.40; $^1H$ NMR ($CDCl_3$) δ 8.73 (1H, d), 7.43 (1H, d), 7.37-7.16 (6H, m), 6.23 (1H, d), 4.63 (1H, dd), 2.30 (3H, s), 0.95 (3H, d), 0.87 (3H, d).

Anal. Calcd. for $C_{35}H_{55}N_5O_6S_2 0.75 H_2O$: C, 58.43; H, 7.91; N, 9.73. Found: C, 58.51; H, 7.74; N, 9.60.

EXAMPLE 2

Alternative Preparation of N-Boc-3-(4-thiazolyl)-L-alanine

EXAMPLE 2A

Ethyl (2-Bromoallyl)acetamidoacetate

To a solution of the product of Example 1H (3.36 g, 10.0 mmol) in dimethylformamide (10 mL) was added sodium chloride (586 mg, 10.0 mmol), water (360 μL, 20 mmol) and 4N hydrochloric acid in dioxane (0.12 mL, 0.5 mmol). The reaction vessel was placed under a positive nitrogen pressure. The reaction mixture was heated at reflux for 24 hours and then concentrated in vacuo. The residue obtained was diluted with water (5 mL) and extracted with ether (3×15 mL). The combined organic extracts were decolorized with charcoal (0.5 g), dried over magnesium sulfate, filtered, and concentrated in wacuo to afford Ehe title product (2.51 g, 95%) as a pale yellow oil. $^1H$ NMR (300 MHz, $CDCl_3$) δ 1.29 (t, 3H), 2.04 (s, 3H), 2.99 (m, 2H), 4.22 (q, 2H), 4.79 (m, 1H), 5.53 (d, 1H), 5.68 (m, 1H), 6.44 (d, 1H); IR (film) 1195, 1220, 1370, 1540, 1660, 1740, 2990, 3050 and 3300 cm$^{-1}$. MS (DCI/$NH_3$) m/e 264/266 (M+H)+, 281/283 (M+H+$NH_3$)+. Anal Calcd. for $C_9H_{14}NO_3Br$: C, 40.92; H, 5.34; N, 5.30. Found: C, 42.04; N, 5.48; N, 5.26.

EXAMPLE 2B

N-Boc-(2-Bromoallyl)glycine

A slurry of the product of Example 2A (16.2 g, 61.3 mmol) in 0.1 N potassium chloride solution (300 mL) containing 0.2 M pH 7.0 phosphate buffer (30 mL) was treated with a solution of Subtilisin Carlsberg (4 rag) in 0.1 N potassium chloride solution (3 mL). The pH was maintained between 6.50 and 7.25 by addition of 2.0 N sodium hydroxide solution via a pH-Stat. After 25 minutes, the rate of hydrolysis noticeably slowed; and unreacted D-ester was extracted with methylene chloride (3×150 mL). The resulting aqueous phase was treated with cobalt (II) acetate (6 mg) and Acylase I (80 mg). The reaction mixture was stirred for 4 hours and determined to be complete.

The pH of the reaction mixture was adjusted to 10 by the addition of solid sodium carbonate. The resultinq solution was treated with di-tert-butyl dicarbonate (6.55 g, 30 mmol) dissolved in THF (100 mL) and vigorously stirred for 16 hours. The aqueous solution was washed with hexane (200 mL) to remove any unreacted protecting-reagent. The aqueous layer was adjusted to pH 2.5 by the addition of solid potassium hydrogen sulfate and extracted with ethyl acetate (2×200 mL). The combined organic layers were washed with brine (100 mL), dried over magnesium sulfate, and concentrated in vacuo to give the title compound (7.30 g, 81%) as a pale yellow crystalline solid. $[α]_D$ at 25° C.=−9.86° (MeOH), c=1.085. $^1H$ NMR (300 MHz, $CDCl_3$) δ1.48 (s, 9H), 2.91 (m, 2H), 4.52 (m, 1H), 5.19 (d, 0.5H), 5.53 (m, 1H), 5.71 (s, 1H), 6.79 (d, 0.5H), 11.3 (s, 1H); IR ($CDCl_3$) 1150, 1250, 1400, 1500, 1620, 1640, 1710, 3000, 3350, and 3520 cm$^{-1}$. (DCI/$NH_3$) m/e 311/313 (M+H+$NH_3$)+. Anal. Calcd. for $C_{10}H_{16}NO_4Br$: C, 42.12; H, 5.66; N, 4.91. Found: C, 41.38; H, 5.59; N, 4.75.

EXAMPLE 2C (2R)-N-Boc-2-amino-5-bromo-4-oxopentanoic Acid

To a solution of the product of Example 2B (2.00 g, 6.80 mmol) in water (30 mL) and tetrahydrofuran (15 mL) cooled to 0° C. was added N-bromosuccinimide (1.45 g, 8.16 mmol) in three portions over twenty minutes. After the addition was complete, the ice bath was removed and the solution was stirred for four hours. The tetrahydrofuran was removed in vacuo and the product was extracted with ethyl acetate (3×35 mL). The organic extracts were combined and washed with 5% sodium chloride solution (25 mL) and brine (25 mL), dried over magnesium sulfate, and concentrated in vacuo to afford the title compound (1.70 g, 81%). $^1H$ NMR (300 MHz, $CDCl_3$)δ1.45 (s, 9H), 3.30 (m, 2H), 3.93 (S, 2H), 4.61 (m, 1H), 5.51 (d, 1H). MS (DCI/$NH_3$) m/e 310/312 (M+H)+, 327/329 (M+H+$NH_3$)+.

EXAMPLE 2D

(2R)-N-Boc-2-Amino-3-(4-thiazolyl)propanoic Acid

To a solution of the product of Example 2C (91 mg, 0.293 mmol) in tetrahydrofuran (5 mL)-was added thioformamide (17.7 rag, 0.29 mmol). [Thioformamide was prepared by reacting a slight excess of phosphorus pentasulfide with formamide in tetrahydrofuran. The resulting solution was diluted with hexanes and filtered through a silica gel plug and stored at −25° C.] The resulting solution was allowed to stand for sixteen hours and then concentrated in vacuo to afford a residue which was partitioned between diethyl ether and aqueous sodium bicarbonate. The aqueous layer was washed with ether (2×10 mL) and methylene chloride (10 mL), adjusted to pH 2.3 with solid potassium hydrogen sulfate, and extracted with ether (3×20 mL). The comb inet organic extracts were dried over magnesium sulfate and concentrated in vacuc to afford the title compound as a white crystalline solid (55 mg, 71%). $^1$H NMR (300 MHz, CDCl$_3$) δ1.48 (s, 9H), 3.48 (m, 2H), 4.52 (m, 1H), 5.61 (m, 1H), 7.18 (d, 1H), 8.91 (d, 1H).

EXAMPLE 3

Alternative Preparation of (2R)-N-Boc-2-Amino-5-bromo-4-oxopentanoic acid

EXAMPLE 3A

Diethyl (2-Chloroallyl)acetamidomalonate

To a suspension of 95% sodium hydride (17.2 g, 680 mmol) in tetrahydrofuran (1.2 L) was added 2,3-dichloropropene (100 g, 900 mmoi), diethylacetamidomalonate (146 g, 672 mmol) and tetrabutylammonium bromide (6.00 g). The resulting thick suspension was warmed at retiux under nltrogen for 20 hours. The reaction mixture was concentrated in vacuo the resulting residue was partitioned between water (200 mL) and a mixture of ether (300 mL) and methylene chloride (100 mL). The organic phase was washed with 5% sodium chloride solution (200 mL) and brine (200 mL), dried over magnesium sulfate, filtered, and concentrated in vacuo. The resulting solid (195 g) was dissolved in hot hexanes (1300 mL) and allowed to cool to room temperaLure and sit overnight to afford the title compound as a crysnaiiine solid (157 g, 80%). mp 76.3° C. $^1$H NMR (300 MHz, CDCl$_3$) δ1.29 (t, 6H), 2.05 (s, 3H), 3.48 (s, 2H), 4.28 (m, 4H), 5.18 (m, 1H), 5.29 (m, 1H), 6.92 (bs, 1H); IR (CDCl$_3$) 1140, 1180, 1200, 1240, 1270, 1300, 1500, 1630, 1680, 1740, 2950, 2990, and 3300 cm$^{-1}$. MS (DCI/NH$_3$) m/e 292/294 (M+H)$^+$. 309/311 (M+H+NH$_3$)$^+$. Anal. Calcd. for C$_{12}$H$_{18}$NO$_5$Cl: C, 49.41; H, 6.22; N, 4.80. Found: C, 49.18; H, 6.29; N, 4.75.

EXAMPLE 3B

Ethyl (2-Chloroallyl)acetamidoacetate

The product of Example 3A (137 g, 500 mmol) was hydrolyzed and decarboxylated by the procedure described in Example 2A to afford the title compound (105.4 g, 96%) as a pale yellow oil which crystallized upon standing. $^1$H NMR (300 MHz, CDCl$_3$) δ1.31 (t, 3H), 2.05 (s, 3H), 2.79 (m, 2H), 4.22 (q, 2H), 4.79 (m, 1H), 5.23 (m, 1H), 5.29 (m, 1H), 6.61 (m, 1H); IR 1200, 1220, 1280, 1300, 1370, 1440, 1550, 1638, 1659, 1740, 2890, 2990, 3050and 3300 cm$^{-1}$. MS (DCI/NH$_3$) m/e 220/222 (M+H)$^+$, 237/239 (M+H+NH$_3$)$^+$. Anal. Calcd. for C$_9$H$_{14}$NO$_3$Cl: C, 49.21; H, 6.42; N, 6.38. Found: C, 46.58; H, 6.05; N, 6.02.

Example 3C

(2R)-N-Boc-2-Amino-5-bromo-4-oxopentanoic acid

The product of Example 3B is treated according to the procedure of Example 2B and 2C to provide the desired product.

EXAMPLE 4

Alternative Preparation of 2(S) Benzyl-3-(1-methylpiperazin-4-ylsulfonyl)propionic acid

EXAMPLE 4A

2-Carbomethoxy-3-phenylpropane-1-sulfonic acid Sodium salt

To a 0.3M ethanolic solution of the product of Example 1B, (Z)-1-bromo-2-carbomethoxy-3-phenyl-2-propene, (0.98 molar equivalents) was added over one hour at 50° C. a 1.4M aqueous solution of sodium sulfite (1.0 molar equivalent). The mixture was stirred for 10 hours at 50° C., and then the ethanol was removed under reduced pressure at 50° C. Ethyl acetate (3 kg per 1 kg of bromide) was added and the mixture stirred for an additional 15 minutes and let stand for 10 minutes. The layers were separated and the aqueous layer was washed as above with two additional aliquots of ethyl acetate (1 kg per 1 kg of bromide).

Raney nickel (1 kg per 10 kg of aqueous solution) was added to the aqueous solution which was then evacuated and purged with nitrogen followed by hydrogen (3x) and placed under 40 psi of hydrogen for 6.5 to 9.5 hours. The Raney nickel was removed by filtration using nitrogen pressure, and the filtrate was concentrated under reduced pressure at 55° C. A 10% aqueous acetone solution (0.3 kg per 1 kg of starting bromide) was added to the residue obtained, and the mixture was warmed at 50° C. for 30 minutes. Additional acetone (3 kg per 1 kg of starting bromide) was slowly added over one hour to effect crystallization ot the product. After stirring for one hour, the product was removed by filtration and washed with acetone to afford the title compound in 60–65%. m.p. 255° C. dec. A second crop was obtained by adding additional acetone (2.5 kg per 1 kg of starting bromide) and cooling to −20 ° C. for 10–12 hours and removing the second crop by filtration. An additonal 13–40% yield of title compound was obtained in that way.

EXAMPLE 4B

Methyl 2-Benzyl-3-(1-methylpiperazin-4-ylsulfonyl)propionate

The product of Example 4A (1 molar equivalent) was mixed with phosphorus pentachloride (1.5 molar equivalents) and warmed at 70°–75° C. for 3–4 hours. The reaction mixture was cooled to room temperature and then diluted with toluene (16.7 molar equivalents) and added to 10% aqueous sodium chloride solution (4 kg per 1 kg of phosphorus pentachloride) while maintaining the temperature below 40° C. The mixture was stirred for 5 minutes, allowed to settle for 15 minutes, and then the phases were separated. The sodium chloride wash was repeated as described above. The toluene phase was cooled to 5° C. and N-methylpiperazine (3 molar equivalents in 3 molar equivalents of toluene) was added maintaining the temperature below 15° C. The mixture was stirred for 4-6 hours and then washed with 8% aqueous sodium hydroxide (2×3.4 kg per 1 kg of phosphorus pentachloride). The combined basic washes were re-extracted with toluene (0.25 kg per 1 kg of sodium hydroxide solution). The combined toluene extracts were washed with water (1 kg per 1 kg cf phosphorus pentachloride), and the toluene was removed by distillation at reduced pressure to afford the title compound (65-70%) as a viscous oil which crystallizes on standing. MS (DCI/NH$_3$) m/e 341 (M+H)$^+$.

EXAMPLE 4C (2S)-2-Benzyl-3-(1-methylpiperazin-4-ylsulfonyl)propionic Acid

The product of Example 4B (69 kg, 202 mol) in acetone (420 kg)/water (960 kg) was adjusted to pH 8.0 using 1N sodium hydroxide. Alcalase TM (Novo Industries, Denmark) (Subtilisin Carlsberg) (6.9 liters) was added and the pH was maintained between 7.9 and 8.4 by the addit ion of 1N sodium hydroxide. When 80% of the theoretical amount of sodium hydroxide had been consumed, the react ion was quenched by the addition of ethyl acetate. The reaction mixture was concentrated to half the original volume under reduced pressure and then washed with ethyl acetate (2×700 kg). The volume of the aqueous phase was concentrated by half and the pH adjusted to 5.2. The reaction mixture was treated with XAD-16 resin (50 kg), stirred for 18 hours, and applied to an XAD-16 resin column (50 kg). The column was eluted with water (500 kg) and then 35% ethanol in water (1000 kg) to afford a residue which was treated with isopropanol (270 kg) and warmed to 75° C. Upon cooling to room temperature and subsequently to −5° C., crystalline material was obtained. The solid was removed by filtration, washed with cold isopropanol (30 kg) and dried at 50° C. to afford the title compound (13 kg, 49%). MS (DCI/NH$_3$) m/e 327 (M+H)$^+$. This compound can be recrystallized from 1:1 isopropanol/water.

EXAMPLE 5

Alternative Preparation of 2 (S)-2-Benzyl-3-(1-methyl piperazin-4-ylsulfonyl)propionyl-L-(4-thiazolyl) Ala Amide of (2S, 3R, 4S)-2-Amino-1-cyclohexyl-3,4-dihydroxy-6-methylheptane

EXAMPLE 5A (2S, 3R, 4S)-2-Amino-1-cyclohexyl-3,4-dihydroxy-6-methylheptane

A 3.5% solution of 2S-t-butyloxycarbonylamino-1-cyclohexyl-3R,4S-dihydroxy-6-methylheptane in 4N ethanolic hydrochloric acid was prepared at 0°-5° C. After 4 hours at 0°-5° C., nitrogen was bubbled through the reaction mixture to remove dissolved hydrochloric acid. The solvent was removed under reduced pressure at 50° C. to afford a solid which was dissolved in ethyl acetate and water. Potassium carbonate was added to bring the pH of the mixture to between 10 and 11, and the layers were separated. The aqueous layer was extracted with additional portions of ethyl acetate. The combined organic extracts were washed with water and brine, dried over magnesium sulfate, and concentrated under reduced pressure at 50° C. to afford a solid. The solid was crystallized by dissolving in a minimum amount of ethanol at 40° C. and then water was slowly added until the ratio of ethanol to water was 40/60 (w/w). The solution was cooled to 0°-5° C. for 2 hours and the product was collected by filtration. The solid was then dried under vacuum at 45° C. to provide title compound as a white crystalline solid (65-72%). m.p. 106°-108° C. MS (DCI/NH$_3$) m/e 244 (M+H)$^+$.

EXAMPLE 5B

Boc-L-(4-Thiazolyl)-Ala Amide of (2S, 3R, 4S)-2-Amino-1-cyclohexyl-3,4-dihydroxy-6-methylheptane To a solution of the product of Example 5A (14.25 g, 58.5 mmol), N-Boc-L-(4-Thiazolyl)Alanine (17.45 g, 64.4 mmol), and 1-hydroxybenzotriazole hydrate (HOBT) (9.86 g, 64.4 mmol) dissolved in dimethylformamide (DMF) (33 mL) and cooled to 0°-5° C. in an ice bath was added dropwise over 30 minutes, a solution of 1,3-dicyclohexylcarbodiimide (DCC) (14.5 g, 70.3 mmol) dissolved in DMF (27 mL). After one hour, the reaction mixture was allowed to warm to room temperature and stirred for 24 hours. The reaction was quenched by the addition of citric acid (1.14 g, 6.0 mmol) and ethanol (1.31 mL, 1.05 g, 22.0 mmol). The mixture was stirred for 1 hour and then ethyl acetate was added (285 mL). After an additional 30 minutes, the solid by-product was removed by filtration and washed with ethyl acetate (48 mL). Additional ethyl acetate (1.9 L) was added and the organic phase was washed with 1% sodium chloride (713 mL), 5% citric acid containing 1% sodium chloride (2×713 mL), 8% sodium bicarbonate (2×713 mL) and 20% sodium chloride (2×713 mL) and concentrated under reduced pressure to afford an off-white solid. The solid was dissolved in isopropanol (200 mL) with warming, treated with decolorizing carbon at 50° C. for one hour, and filtered through Celite. The liltrate was diluted with isopropanol (50 mL) and stirred at room temperature with a mechanical stirrer for 15 hours. The solid suspension was cooled to 0°-5° C. with an ice bath and stirred at this temperature for 3 hours. The solid was removed by cold filtration, washed with cold 1:1 isopropanol/heptane (100 mL), and dried in a vacuum oven at 50° C. for 48 hours to afford the title compound as a white solid in 85% yield. m.p. 156°-158° C. MS (DCI/NH$_3$) m/e 498 (M+H)$^+$.

EXAMPLE 5C

H-L-(4-Thiazolyl)Ala Amide of (2S,3R,4S)-2-Amino-1-cyclohexyl-3,4-dihydroxy-6-methylheptane A 12% solution of the product of Example 5B at 15°-25° C. in 3N aqueous hydrochloric acid was prepared. After 4 hours at 15°-25° C., the reaction mixture was quenched by pouring it into a mixture of 4% sodium hydroxide/15% sodium chloride/ethyl acetate. The pH of the mixture was brought up to 10-12 by the addition of 10% sodium hydroxide. The layers were separated and the aqueous layer extracted with ethyl acetate (2×). The combined organic extracts were washed with 25% sodium chloride (2×), dried over magnesium sulfate, treated with activated carbon at 50° C. for 1 hour, and filtered through Cetite. The filtrate was concentrated to a solid under reduced pressure at 45° C. The solid was crystallized by dissolving in a minimum amount of ethyl acetate (5× by weight) and triturating with heptane until the ratio of ethyl acetate to heptane was 30/70 (w/w). The solution was cooled to 0°-5° C. and stirred for two hours and then filtered. The solid was dried in a vacuum oven at 45° C. for 60 hours or until the loss on drynq was less than 0.1%. The title compound was obtained as a white crystalline solid in 70-82% yield. m.p. 109°-112° C. MS (DCI/NH$_3$) m/e 398 (M+H)+.

EXAMPLE 5D (2S)-2-Benzyl-3-(i-methylpiperazin-4-yl sulfonyl) propionyl-L-(4-Thiazolyl)Ala Amide of (2S, 3R, 4S)-2-Amino-1-cyclohexyl3,4-dihydroxy-6-methylheptane The product of Example 5C (3.00 g, 7.6 mmol), the product of Example 4C, 2S-benzyl-3-(1-methylpiperazin-4-yl sulfonyl)propionic acid, (2.59 g, 7.9 mmol), and HOBT (1.27 g, 8.3 mmol) were dissolved in DMF (30 mL). After stirring at room temperature for t hour, the react ion mixture was cooled to 0°-5° C. in an ice bath and treated with the dropwise addition over a 30 minute period of a solution of DCC (1.72 g, 8.3 mmol) dissolved in DMF (8 mL). After 1 hour, the reaction mixture was allowed to warm to amjDient temperature and stirred for 24 hours. The reaction mixture was quenched with citric acid (0.15 g, 0.26 mmol) and ethanol (0.17 mL, 3.04 mmol) and stirred for 1 hour. Ethyl acetate (60 mL) was added and the mixture was stirred for an additional hour. The by-product was removed by filtration and washed with ethyl acetate (10 mL). The filtrate was diluted with ethyl acetate (400 mL) and washed with 5% sodium bicarbonate solution (2×100 mL), 1% sodium chloride solution (100 mL), and 20% sodium chloride solution (100 mL). The solvent was removed under reduced pressure to afford an off-white solid. The solid was dissolved in isopropanol (80 mL) with warming, treated with decolorizing carbon at 55° C. for 1 hour, filtered through Celite, and stirred at ambient temperature with a mechanical stirrer for 12 hours. The white solid suspension was cooled to 0°-5° C. in an ice bath for 3 hours and filtered cold. The solid obtained was washed with cold 1:1 heptane/isopropanol (25 mL) and dried in a vacuum oven at 55° C. for 48 hours to afford the title comound (4.32 g, 81%) as a white solid. m.p. 169°-170° C. MS (DCI/NH$_3$) m/e 706 (M+H)+.

EXAMPLE 6

(2S)-2-Benzyl--3-(piperazin-4ylsulfonyl)propionyl-(L-4-Thiazolyl)Ala Amide of (2S, 3R, 4S)-2-Amino-1-cyclohexyl-3,4-dihydroxy-6-methylheptane

EXAMPLE 6A

Methyl 2-Benzyl-3-(1-benzyl-piperazin-4-ylsulfonyl)propionate

To a 3 L round bottom flask was added the resultant compound from Example 1E (370.5 g, 1.34 mol) and dichloromethane (2 L). The mixture was cooled to 0° C. in an ice water bath and a solution of N-benzyl piperazine (295.8 g, 1.68 mol) was added dropwise with vigorous stirring over 2 h. After the addition was completed, the mixture was stirred an additional 4 h while at 0° C. The solution was then poured into a separatory funnel containing 2 L of a 5% aqueous NaOH solution. The layers were partitioned and the organic layer was dried over potassium carbonate. Concentration in vacuo yielded an oil, which was filtered through 1 kg of silica gel using 3:2 hexane/ethyl acetate as an eluant. Concentration gave 467 g (84%) Of the desired product: $^1$H NMR (CDCl$_3$) δ7.37-7.12 (m, 10H), 3.66 (s, 3H), 3.51 (s, 2H), 3.42 (dd, 1H), 3.29-3.13 (m, 5H), 3.06 (dd, 1H), 2.96-2.84 (m, 2H), 2.50-2.42 (m, 4H).

EXAMPLE 6B

Methyl 2-Benzyl-3-(piperazin-4-ylsulfonyl) propionate Hydrochloride

The resultant compound from Example 6A (466 g, 1.12 mol) was dissolved in methylene chloride and treated with gaseous HCl. The solution was evaporated and the residue was dissolved in methanol, treated with 10% Pd/C and hydrogenated under 50 psi hydrogen. The mixture was evaporated to afford 330 g (81%)of the desired product: $^1$H NMR (CDCl$_3$) δ7.37-7.13 (m, 5H), 368 (s, 3H), 3.42 (dd, 1H), 3.29-3.18 (m, 1N), 3.18-3.12 (m, 4H), 3.07 (dd, 1H), 2.97-2.82 (m, 6H).

EXAMPLE 6C (2S) 2-Benzyl-3-[(1-tert-butyloxycarbonyl)-piperazin-4-ylsulfonyl]propionic Acid.

The resultant ester from Example 6B (56 g, 150 mmol) was suspended in an aqueous anionic solution (0.1 M KCl, 3 L) containing CH$_3$CN (200 mL) in a 5 L 3-neck round bottom flask, equipped with a mechanical stirrer. The pH at this point was 6.6. A solution of NaOH (0.2 M, 350 mL) was added to bring the pH to 7.8. Chymotrypsin (1.57 g, 3.1 w/w enzyme/substrate) was added and the pH of the reaction was maintained between 7.6-7.8. After 12 h, the reaction had consumed 75% of the theoretical amount of base (0.2 M NaOH, 250 mL). The medium was extracted with CHCl$_3$ (1 L) to remove unreacted starting material. The aqueous phase was then placed in a 12 L 3-neck round bottom flask along with dioxane (1 L). The pH at this point was 5.5 and it was adjusted to 9 using 6 M NaOH. Di-tert-butyldicarbonate (20.9 g, 96 mmol) in dioxane (100 mL) was added dropwise over 4 h while maintaining the pH at 9 (1 M NaOH, 100 mL). After stirring over night, the total volume of the reaction mixture was reduced to 2 L, and the mixture was washed with ether (800 mL). The aqueous phase was acidified to pH 4 with 3 M HCl, and then was extracted with CHCl$_3$ (2×1 L). After drying over MgSO$_4$, filtration and evaporation afforded 28 g (88%) of a white solid, m.p. 146° C.

EXAMPLE 6D (2S)-2-Benzyl-3-(piperazin-4-ylsulfonyl)propionyl-(L)-(4-Thiazolyl)Ala Amide of (2S, 3R, 4S)-2-Amin0-1-cyclohexyl-3,4-dihydroxy-6-methylheptane To the resultant acid from Example 6C (0.350 g, 0.85 mmol), the resultant amine from Example 1Q (0.340 g, 0.86 mmol), and 1-hydroxybenzotriazole (0.310 g, 2.29 mmol) in dimethylformamide (5 mL) was added N-methylmorpholine (0.11 mL, 1.0 mmol). The mixture was cooled to −23° C. and treated with 1-(3-dimethylaminopropyl)-3-ethylcarbodiimide hydrochloride (0,235 g, 1.23 mmol). After 2 h at −23° C. and 14 h at ambient temperature, the reaction was poured into saturated NaHCO$_3$ solution and extracted into ethyl acetate which was washed with water and brine and then was dried over Na$_2$SO$_4$ and evaporated to afford 0.69 g.

This material was dissolve in methylene chloride (25 mL), cooled to 0° C., and treated -with trifluoroacetic acid (25 mL). After 3 h at 0° C., the solvent was evaporated, and the residue was dissolved in water and basified to pH 9 with solid Na$_2$CO$_3$. The mixture was extracted into chloroform which was dried over Na$_2$SO$_4$ and evaporated. Recrystallization from chloroform (10 mL)/hexane (25 mL) afforded 0.540 (92%) of a white solid: m.p. 168°–169° C.; TLC (15% CH$_3$OH/85% CHCl$_3$) R$_f$=0.29.

Anal. Calcd. for C$_{34}$H$_{53}$N$_5$O$_6$S$_2$.0.75 H$_2$O: C, 59.02; H, 7.72; N, 10.12. Found: C, 58.62; H, 7.65; N, 10.04.

EXAMPLE 7

N-(4-Morpholinylsulfonyl)-(L)-phenylalanyl-L)-(2-amino-4-thiazolyl)alanyl amide of (2S, 3R, 4S)-2-Amino-1-cyclohexyl-3,4-dihydroxy-6-methylheptane The title compound can be prepared according to the procedure disclosed in European Patent Application No . EP 399556, published November 28, 1990.

EXAMPLE 8

(2S, 3R, 4S)-N-Boc-2-Amino-1-cyclohexyl-3,4-dihydroxy-4-(cyclopropyl)butane

The title compound can be prepared according to the procedure disclosed in European Patent Application No. EP-332008, published Sep. 13, 1989.

EXAMPLE 9

Alternative Preparation of (2S)-2-Benzyl-3-(1-methylpiperazin-4-ylsulfonyl) propionyl-(L)-(4-Thiazolyl)Ala Amide of (2S, 3R 4S)-2-Amino-1-cyclohexyl-3,4-dihydroxy-6-methylheptane (Method B)

The resultant compound from Example 6D (114 g, 144 mmol) in methanol (800 mL) at 0° C. was treated with 37.3% aqueous formaldehyde (22 mL, 300 mmol) and 4.0 M HCl in dioxane (18 mL, 72 mmol). Sodium cyanoborohydride (9.00 g, 144 mmol) was added and the mixture was stirred at 0° C. for 30 min. The solvent was evaporated and the residue was taken up in ethyl acetate which was washed with saturated NaHCO$_3$ solution, water, and brine; and then was dried over Na$_2$SO$_4$ and evaporated. Recrystalization of the residue from ethanol (1 L)/hexane (6 L) afforded 65.41 g (65%) of the title product. Recrystalization of the mother liquors from ethyl acetate (360 mL) / hexane (360 mL) afforded an additional 13.05 g of product for an overall yield of 77%.

EXAMPLE 10

(2S)-2-Benzyl-3-(1-methyl-1-oxo-piperazin-4-ylsulfonyl)-propionyl-(L)-(4-Thiazolyl)Ala Amide of (2S,3R,4S)-2-Amino-1-cyclohexyl-3,4-dihydroxy-6-methylheptane

EXAMPLE 10A (2S) 2-Benzyl-3-(1-methyl-1-oxo-piperazin,4-ylsulfonyl)propionic Acid Sodium Salt The resultant acid from Example 1G (100.2 mg, 0.307 mmol) in water (4 mL) was treated with NaOH in water (0.30 mL, 0.31 mmol, 1.04 M) followed by H$_2$O$_2$(0.070 mL, 6.85 mmol, 30% solution). After 40 h, a second portion of H$_2$O$_2$ (0.070 mL, 6.85 mmol, 30% solution) was added and the reaction was stirred for an additional 50 h. A small amount of Pt black was added, and following the cessation of gas evolution, the mixture was filtered and lyophilized to a white powder: TLC (25% ethyl acetate/25% water/25% acetic acid/25% n-butanol) R$_f$=0.63; $^1$H NMR (CD$_3$OD) 7.32–7.15 (m, 5H) , 3.22 (s, 3H) , 2.83 (dd, 1H), 2.71 (dd, 1H).

EXAMPLE 10B (2S)-2-Benzyl-3-(1-methyl-1-oxo-piperazin-4-ylsulfonyl)propionyl-(L)- (4Thiazolyl)Ala Amide of (2S,3R,4S)-2-Amino-1-cyclohexyl-3,4-dihydroxy-6-methylheptane Using the procedure of Example 1R and replacing the resultant acid from Example 1G with the resultant acid salt from Example 10A gave, after chromatography on silica gel with 10% methanol and 1% NH$_4$OH in chloroform, the desired product (58%) as a solid: m.p. 108°–115° C.; TLC (10% methanol/1% NH$_4$OH /89% chloroform) R$_f$=0.095; $^1$H NMR (CDCl$_3$) 8.77 (d, 1H) , 7.65 (d, 1H) , 7.38–7.15 (m, 6H), 7.00 (br d, 1H) , 4.77 (dd, 1H) , 4.30–4.17 (m, 1H), 3.43 (s, 3H) 0.93 (d, 3H) , 0.87 (d, 3H).

Anal (C$_{35}$H$_{55}$N$_5$O$_7$S$_2$ . 0.25 H$_2$O)
Calcd: C, 57.87; H, 7.70; N, 9.64.
Found: C, 57.57; H, 7.43; N, 9.53.

EXAMPLE 11

(2S)-2-Benzyl-3-(2-oxo-piperazin-4-ylsulfonyl)propionyl-(L)-(4-Thiazolyl) Ala Amide of (2S,3R,4S)-2-Amino-1-cyclohexyl-3,4-dihydroxy-6-methylheptane

EXAMPLE 11A

Benzyl α-Benzylacrylate.

αBenzylacrylic acid (2.20 g, 13.6 mmol) in dry ether (40 mL) was treated with dicyclohexylcarbodiimide (2.60 g, 12.6 mmol ), benzyl alcohol (1.30 mL, 12.6 mmol ) and 4-dimethylaminopyridine (0.310 g, 2.54 mmol). After stirring at room temperature for 44 h, the mixture was filtered and evaporated. Chromatography of the residue on silica with 5% ethyl acetate in hexane afforded 2.70 g (85%) of a colorless oil: TLC (20% ethyl acetate/80% hexane) R$_f$=0.59; $^1$H NMR (CDCl$_3$) 7.15–7.40 (m, 10H), 6.28 (m, 1H) , 5.49 (m, 1H), 5.17 (s, 2H) , 3.67 (s, 2H).

Anal. (C$_{17}$H$_{16}$O$_2$ . 0.15 H$_2$O)
Calcd: C, 80.07; H, 6.44.
Found: C, 80.17; H, 6.47.

EXAMPLE 11B

Benzyl 3-Acetylmercapto-2-benzylpropionate

The resulting compound from Example 11A (7.00 g, 27.7 mmol) in dry ether (10 mL) was treated with thiolacetic acid (3.00 mL, 42.0 mmol) and pyridine (2.30 mL, 28.4 mmol). After 114 h at room temperature the mixture was evaporated and chromatographed on silica gel (500 g) with 5–10% ethyl acetate in hexane to afford 8.34 g (92%) of a mobile oil: TLC (20% ethyl acetate/80% hexane) R$_f$=0.40; $^1$H NMR (CDCl$_3$) 7.05–7.40 (m, 10H), 5.05 (s, 2H) , 2.87–3.20 (m, 5H), 2.31 (s, 3H).

Anal. (C$_{19}$H$_{20}$O$_3$S. 0.5 H$_2$)
Calcd: C, 67.63; H, 6.27.
Found: C, 67.98; H, 6.04.

EXAMPLE 11C

2-Benzyloxycarbonyl-3-phenyl-1-propylsulfonyl Chloride.

Chlorine was bubbled into a mixture of the resultant compound from Example 11A (8.34 g, 25.4 mmol) in water (250 mL) for 30 min at room temperature followed by nitrogen which was bubbled through the mixture for 15 min. The mixture was extracted with methylene chloride which was dried over $MgSO_4$ and evaporated to afford 8.55 g (95%) of an oil which was used without further purification. $^1H$ NMR ($CDCl_3$) 7.05–7.45 (m, 10H), 5.13 (s, 2H), 4.21 (dd, 1H), 3.67 (dd, 1H), 3.46–3.57 (m, 1H), 3.16 (dd, 1H), 2.94 (dd, 1H).

EXAMPLE 11 D

Benzyl 2-Benzyl-3-(2-oxo-piperazin-4-ylsulfonyl) propionate

To the resultant compound from Example 11C (320.5 mg, 0.908 mmol) in dichloromethane (5 mL) at $-10°$ C. was added 2-oxopiperazine (140 mg, 1.40 mmol, Yu et al. *J. Med. Chem.* 1900, 31, 1435) in pyridine (2 mL). After 30 min at $-10°$ C. and 30 min at ambient temperature, the solvent was evaporated and the residue was partitioned between ether and 0.5 M $H_3PO_4$. The organic layer was washed with 0.5 M $H_3PO_4$, saturated $NaHCO_3$ solution and brine, and then was dried over $MgSO_4$ and evaporated. Chromatography of the residue on silica gel with 2% methanol in chloroform afforded 237.1 mg (63%) of the desired product as a foam: TLC (5% methanol/95% chloroform) $R_f32$ 0.26; $^1H$ NMR ($CDCl_3$) 7.43–7.07 (m, 10H), 5.97 (br, 1H), 5.12 (d, 1H), 5.08 (d, 1H), 3.82 (d, 1H), 3.78 (d, 1H), 3.55 (dd, 1H), 3.43–3.17 (m, 5H), 3.07 (dd, 1H), 3.01 (dd, 1H), 2.87 (dd, 1H).

EXAMPLE 11E

2-Benzyl-3-(2-oxo-piperazin-4-ylsulfonyl) propionic Acid

The resultant compound from Example 11D (234 mg, 0.562 mmol) and 10% Pd/C (100 mg) in methanol (9 mL) were stirred under a hydrogen atmosphere for 90 min. The mixture was filtered and evaporated to afford 105.1 mg (57%) of the desired product as a solid: m.p. 168°–171° C.

Anal ($C_{14}H_{18}N_2O_5S$ . 0.9 $H_2O$)
Calcd: C, 49.08; H, 5.82; N, 8.18.
Found: C, 48.72; H, 5.36; N, 7.98.

EXAMPLE 11F (2S)-2-Benzyl-3-2-oxo-Piperazin-4-ylsulfonyl)propionyl-(L)-(4-Thiazolyl)Ala Amide of (2S,3R,4S)-2-Amino-1-cyclohexyl-3,4-dihydroxy-6-methylheptane Using the procedure of Example 1R and replacing the resultant acid from Example 1G with the resultant acid salt from Example 11E gave, after chromatography on silica gel with 2–4% methanol in chloroform, the (2R)-isomer (40%; TLC (10% methanol/90% chloroform) $R_f=0.33$) followed by the desired (2S)-isomer (38%) as a solid: m.p. 130°–140° C.; TLC (10% methanol/90% chloroform) $R_f=0.28$; $^1H$ NMR ($CDCl_3$) 8.78 (d, 1H), 7.78 (d, 1H), 7.40–7.17 (m, 6H), 6.46 (br s, 1H), 6.40 (d, 1H), 4.72 (dd, 1H), 4.33–4.18 (m, 1H), 3.86 (s, 2H), 0.95 (d, 3H), 0.87 (d, 3).

Anal ($C_{34}H_{51}N_5O_7S_2$)
Calcd: C, 57.85; H, 7.28; N, 9.92.
Found: C, 57.89; H, 7.38; N, 9.80.

EXAMPLE 12

(4-Methylpiperazin-1-yl) sulfonyl-(Phenylmethyl)alanine-N-Methyl-3-(4-thiazolyl)-L-alanine Amide of (2S,3R,4S)-2-amino-1-cyclohexyl-3,4-dihydroxy-6-methylheptane

EXAMPLE 12A

N-Boc-N-Methyl-3-(4-thiazolyl)-L-alanine

The resultant compound from Example 10 (825 mg, 3.03 mmol) in tetrahydrofuran (9 mL) at 0° C. was treated with NaH (390 mg, 9.75 mmol, 60% in oil) followed by iodomethane (1.50 mL, 24.1 mmol). The mixture was warmed to ambient temperature and stirred for 22 h. The mixture was diluted with water, washed with ether, acidified to pH 3 with 0.5 M $H_3PO_4$, and extracted into ethyl acetate which was washed with brine, dried over $Na_2SO_4$, and evaporated to afford 870 mg (100%) of the desired product as a foam: TLC (20% methanol/79% chloroform/1% acetic acid) $R_f=0.51$; $^1H$ NMR ($CDCl_3$) 8.82 (s, 1H), 7.12, 7.08 (2s, total 1H), 5.00–4.88, 4.80–4.70 (2m, total 1H), 3.60–3.22 (m, 2H), 2.81 (s, 3H), 1.43, 1.40 (2s, total 9H).

EXAMPLE 12B

N-Boc-N-Methyl-3-(4-thiazolyl)-L-alanine Amide of (2S,3R,4S)-2-Amino-1-cyclohexyl-3,4-dihydroxy-6-methylheptane Using the procedure of Example 1P with the resultant acid from Example 12A gave, after recrystalizing from ethyl acetate/hexane, the desired product in 84% yield: TLC (10% methanol/90% chloroform) $R_f=0.61$; 1H NMR ($CDCl_3$) 8.73 (s, 1H), 7.08 (d, 1H), 6.33 (br d, 1H), 5.15–5.00 (m, 1H), 2.82 (s, 3H), 1.43 (s, 9H), 0.92 (d, 3H), 0.83 (d, 3H).

EXAMPLE 12C

N-Methyl-3-(4-thiazolyl)-L-alanine Amide of (2S,3R,4S)-2-Amino-1-cyclohexyl-3,4-dihydroxy-6-methylheptane Using the procedure of Example 1Q with the resultant compound from Example 12B gave, after recrystalizing from dichloromethane/hexane, the desired product in 54% yield: TLC (15% methanol/85% chloroform) $R_f=0.46$; $^1H$ NMR ($CDCl_3$) 8.77 (d, 1H), 7.02 (d, 1H), 4.50 (br, 1H), 4.35–4.22 (m, 1H), 3.05 (dd, 1H), 2.38 (s, 3H, 0.95 (d, 3H), 0.86 (d, 3H).

EXAMPLE 12D

Boc-(Phenylmethyl)alanine-N-Methyl-3-(4-thiazolyl)-L-alanine Amide of (2S,3R,4S)-2-Amino-1-cyclohexyl-3,4-dihydroxy-6-methylheptane The resultant compound from Example 12C (103 mg, 0.250 mmol) and Boc-(homo)Phe-OH (85.0 mg, 0.30 mmol) in dichloromethane (3 mL), at 0° C. were treated with triethyl amine (0.110 mL, 0.790 mmol) and BOP-Cl (80.0 mg, 0.31 mmol). After 4 h at 0° C. and 19 h at ambient temperature the mixture was evaporated and the residue was taken up in ethyl acetate which was washed with saturated $NaHCO_3$ solution, water, and brine; and then was dried over $Na_2SO_4$ and evaporated.

Chromatography of the residue on silica gel with 50% ethyl acetate in hexane afforded 154 mg (92%) of the desired product: TLC (ethyl acetate) $R_f=0.51$; $^1$H NMR (CDCl$_3$) 8.83 (d, 1H), 7.34–7.02 (m, 6H), 5.09 (d, 1H), 4.96 (dd, 1H), 3.73 (dd, 1H), 3.00 (s, 3H), 1.44 (s, 9H), 0.97 (d, 3H), 0.90 (d, 3H).

Anal (C$_{36}$H$_{56}$N$_4$O$_6$S)
Calcd: C, 64.26; H, 8.39; N, 8.33.
Found: C, 63.88; H, 8.32; N, 8.18.

EXAMPLE 12E

H-(Phenylmethyl) alanine-N-Methyl-3-(4-thiazolyl)-L-alanine Amide of (2S,3R,4 S)-2-Amino-1-cyclohexyl-3,4-dihydroxy-6-methylheptane Using the procedure of Example 1Q with the resultant compound from Example 12D gave, after chromatography on silica gel with 3% methanol in chloroform, the desired product (93%): m.p. 84°–95° C.; TLC (15% methanol/85% chloroform) $R_f=0.47$.

Anal (C$_{31}$H$_{48}$N$_4$O$_4$S . 0.5 H$_2$O)
Calcd: C, 64.00; H, 8.49; N, 9.63.
Found: C, 64.25; H, 8.24; N, 9.74.

EXAMPLE 12F (4-Methylpiperazin-1-yl) sulfonyl-(Phenylmethyl)alanine-N-Methyl-3-(4-thiazolyl)-L-alanine Amide of (2S,3R,4S)-2-Amino-1-cyclohexyl-3,4-dihydroxy-6-methylheptane The resultant compound from Example 12E (111 mg, 0.194 mmol), (1-methylpiperazin-4-yl) sulfonyl chloride hydrochloride (120 mg, 0.51 mmol, Matier et al. *J. Med. Chem.* 1972, 15, 538), and triethylamine (0.210 mL, 1.51 mmol) in tetrahydrofuran (2 mL) were stirred at ambient temperature for 18 h and then at 45° C. for 24 h . The mixture was poured into saturated NaHCO$_3$ solution and extracted into ethyl acetate which was washed with brine, dried over Na$_2$SO$_4$ and evaporated. Chromatography of the residue on silica gel with 2.8% methanol in chloroform afforded 96.0 mg (67%) of the desired product: m.p. 90°–105° C.; $^1$H NMR (CDCl$_3$) 8.72, 8.52 (2d, total 1H), 2.95, 2.79 (2s, total 3H), 2.31, 2.27 (2s, total 3H).

Anal (C$_{36}$H$_{58}$N$_6$O$_6$S$_2$ . 0.5 H$_2$O)
Calcd: C, 58.12; H, 7.99; N, 11.30.
Found: C, 58.30; H, 7 67; N, 10 91.

EXAMPLE 13

[(1-Methylpiperazin-4-yl) sulfonyl]phenylalanine-3-(4-thiazolyl)-L-alanine Amide of (2S,3R,4S)-2-Amino-1-cyclohexyl-3,4-dihydroxy-6-methylheptane

EXAMPLE 13A

[(1-Methylpiperazin-4-yl) sulfonyl]phenylalanine Benzyl Ester

To a suspension of H-Phe-OBn p-toluenesulfonic acid salt (1.67 g, 3.91 mmol) and (1-methylpiperazin-4-yl) sulfonyl chloride hydrochloride (1.00 g, 4.25 mmol, Matier et al. *J. Med. Chem.* 1972, 15, 538) in dichloromethane (7 mL) was added triethylamine (1.7 mL, 12 . 7 mL, 12 mmol). After 24 h at ambient temperature, the mixture was diluted with ethyl acetate which was washed with saturated NaHCO$_3$ solution and brine, and then was dried over Na$_2$SO$_4$ and evaporated to afford 1.65 g (100% ) of the desired product as an oil: TLC (15% methanol/85% chloroform) $R_f=0.52$; $^1$H NMR (CDCl$_3$) 7.43–7.03 (m, 10H), 5.16 (s, 2H), 4.74 (d, 1H), 4.31–4.21 (m, 1H), 3.19–2.97 (m, 6H), 2.40–227 (m, 4H), 2.26 (s, 3H).

EXAMPLE 13B

[(1-Methylpiperazin-4-yl)sulfonyl]phenylalanine

The resultant compound from Example 13A (1.64 g, 3.92 mmol) and 10% Pd/C (0.13 g) in methanol (25 mL) were stirred under a hydrogen atmosphere for 30 min. 10% Pd/C (0.27 g) was added and the reaction was continued for an additional 2 h. The mixture was filtered with hot methanol washes and evaporated to afford 1.19 g (93%) of the desired product as a solid: m.p. >200° C.; $^1$H NMR (DMSO-D$_6$) 7.83 (d, 1H), 7.47–7.17 (m, 5H) , 3.87–3.73 (m, 1H), 3.03–2.63 (m, 6H), 2.25–2.10 (m, 4H), 2.12 (s, 3H).

EXAMPLE 13C

[(1-Methylpiperazin-4-yl) sulfonyl]phenylalanine-3-4-thiazolyl)-L-alanine Amide of (2S,3R,4S)-2-Amino-1-cyclohexyl-3,4-dihydroxy-6-methylheptane Using the procedure of Example 1P with the resultant compounds from Examples 1Q and 13B gave, after chromatography on silica gel with 2.5% methanol in chloroform, the desired product (100% ) as a solid: TLC (15% methanol/85% chloroform) $R_f=0.53$; $^1$H NMR (CDCl$_3$) 9.28 (d, 1H), 8.85 (d, 1H), 7.45–7.21 (m, 5H), 7.16 (d, 1H) , 6.54 (d, 1H), 4.82 (d, 1H), 4.74–4.66 (m, 1H), 4.27–4.10 (m, 2H), 3.97–3.84 (m, 1H), 3.54 (dd, 1H), 4.41 (dd, 1H), 2.78 (dd, 1H), 2.24 (s, 3H), 0.96 (d, 3H), 0.94 (d, 3H ).

Anal (C$_{34}$H$_{54}$N$_6$O$_6$S$_2$)
Calcd: C, 57.76; H, 7.70; N, 11.89.
Found: C, 57.49; H, 7.79; N, 11.48.

EXAMPLE 14 (parts i-ccclxxxi)

The following compounds can be prepared using the procedures outlined above:

(i) (2S)-2-Benzyl-3-(1-methylpiperazin-4-ylsulfonyl)-propionyl-(L)-(5-Thiazolyl)Ala Amide of (2S,3R,4S)-2-Amino-1-cyclohexyl-3,4-dihydroxy-6-methylheptane;

(ii) (2S)-2-Benzyl-3-(1-methylpiperazin-4-ylsulfonyl)-propionyl-(L)-(2-Thiazolyl)Ala Amide of (2S,3R,4S)-2-Amino-1-cyclohexyl-3,4-dihydroxy-6-methylheptane;

(iii) (2S)-2-Benzyl-3-(1-methylpiperazin-4-ylsulfonyl)-propionyl-(L)-(1-pyrazolyl)Ala Amide of (2S,3R,4S)-2-Amino-1-cyclohexyl-3,4-dihydroxy-6-methylheptane;

(iv) (2S)-2-Benzyl-3-(1-methylpiperazin-4-ylsulfonyl)-propionyl-(L)-(3-pyrazolyl)Ala Amide of (2S,3R,4S)-2-Amino-1-cyclohexyl-3,4-dihydroxy-6-methylheptane;

(v) (2S)-2-Benzyl-3-(1-methylpiperazin-4-ylsulfonyl)-propionyl-(L)-(1-imidazolyl)Ala Amide of (2S,3R,4S)-2-Amino-1-cyclohexyl3,4-dihydroxy-6-methylheptane;

(vi) (2S)-2-Benzyl-3-(1-methylpiperazin-4-ylsulfonyl)-propionyl-(L)-leucine Amide of (2S,3R,4S)-2-Amino-1-cyclohexyl-3,4-dihydroxy-6-menhylheptane;

(vii) (2S)-2-Benzyl-3-(1-methylpiperazin-4-ylsulfonyl)-propionyl-(L)-(nor)leucine Amide of (2S,3R,4S)-2-Amino-1-cyclohexyl3,4-dihydroxy-6-methylheptane;

(viii) (2S)-2-Benzyl-3-(1-methylpiperazin-4-ylsulfonyl)-propionyl-(L)-(2-aminothiazol-4-yl)Ala Amide of (2S,3R,4S)-2-Amino-1-cyclonexyl-3,4-dihydroxy-6-methylheptane;

(ix) (2S)-2-Benzyl-3-(1-methylpiperazin-4-ylsulfonyl)-propionyl-(L)-methionine Amide of (2S,3R,4S)-2-Amino-1-cyclohexyl-3,4-dihydroxy-6-methylheptane;

(x) (2S)-2-Benzyl-3-(1-methylpiperazin-4-ylsulfonyl)-propionyl-(L)-(S-Me)Cys Amide of (2S,3R,4S)-2-Amino-1-cyclohexyl-3,4-dihydroxy-6-methylheptane;

(xi) (2S)-2-Benzyl-3-(piperazin-4-ylsulfonyl)propionyl-(L)-(5-Thiazolyl)Ala Amide of (2S,3R,4S)-2-Amino-1-cyclohexyl-3,4-dihydroxy-6-methylheptane;

(xii) (2S)-2-Benzyl-3-(piperazin-4-ylsulfonyl)propionyl-(L)-(2-Thiazolyl)Ala Amide of (2S,3R,4S)-2-Amino-1-cyclohexyl3,4-dihydroxy-6-methylheptane;

(xiii) (2S)-2-Benzyl-3-(piperazin-4-ylsulfonyl)propionyl-(L)-(1-pyrazolyl)Ala Amide of (2S,3R,4S)-2-Amino-1-cyclohexyl3,4-dihydroxy-6-methylheptane;

(xiv) (2S)-2-Benzyl-3-(piperazin-4-ylsulfonyl)propionyl-(L)-(3-pyrazolyl)Ala Amide of (2S,3R,4S)-2-Amino-1-cyclohexyl3,4-dihydroxy-6-methylheptane;

(xv) (2S)-2-Benzyl-3-(piperazin-4-ylsuifonyl)propionyl-(L)-(1-imidazolyl)Ala Amide of (2S,3R,4S)-2-Amino-1-cyclohexyl3,4-dihydroxy-6-methylheptane;

(xvi) (2S)-2-Benzyl-3-(piperazin-4-ylsulfonyl)propionyl-(L)-leucine Amide of (2S,3R,4S)-2-Amino-1-cyclohexyl3,4-dihydroxy-6-methylheptane;

(xvii) (2S)-2-Benzyl-3-(piperazin-4-ylsulfonyl)propionyl-(L)-(nor)leucine Amide of (2S,3R,4S)-2-Amino-1-cyclohexyl3,4-dihydroxy-6-methylheptane;

(xviii) (2S)-2-Benzyl-3-(piperazin-4-ylsulfonyl)propionyl-(L)-(2-aminothiazol-4-yl)Ala Amide of (2S,3R,4S)-2-Amino-1-cyclohexyl3,4-dihydroxy-6-methylheptane;

(xix) (2S)-2-Benzyl-3-(piperazin-4-ylsulfonyl)propionyl-(L)-methionine Amide of (2S,3R,4S)-2-Amino-1-cyclonexyl-3,4-dihydroxy-6-methylheptane;

(xx) (2S)-2-Benzyl-3-(piperazin-4-ylsulfonyl) propionyl-(L)-(S-Me)Cys Amide of (2S,3R,4S)-2-Amino-1-cyclonexyl-3,4-dihydroxy-6-methylheptane;

(xxi) (2S)-2-Benzyl-3-(2-oxo-piperazin-4-ylsulfonyl)propionyl-(L)-(5-Thiazolyl)Ala Amide of (2S,3R,4S)-2-Amino-1-cyclohexyl3,4-dihydroxy-6-menthylheptane;

(xxii) (2S)-2-Benzyl-3-(2-oxo-piperazin-4-ylsulfonyl)-propionyl-(L)-(2-Thiazolyl)Ala Amide of (2S,3R,4S)-2-Amino-1-cyclohexyl3,4-dihydroxy-6-methylheptane;

(xxiii) (2S)-2-Benzyl-3-(2-oxo-piperazin-4-ylsulfonyl)-propionyl-(L)-(1-pyrazolyl)Ala Amide of (2S,3R,4S)-2-Amino-1-cyclohexyl3,4-dihydroxy-6-methylheptane;

(xxiv) (2S)-2-Benzyl-3-(2-oxo-piperazin-4-ylsulfonyl)-propionyl-(L)-(3-pyrazolyl)Ala Amide of (2S,3R,4S)-2-Amino-1-cyclohexyl-3,4-dihydroxy-6-methylheptane;

(xxv) (2S)-2-Benzyl-3-(2-oxo-piperazin-4-ylsulfonyl)-propionyl-(L)-(1-imidazolyl)Ala Amide of (2S,3R,4S)-2-Amino-1-cyclohexyl-3,4-dihydroxy-6-methylheptane;

(xxvi) (2S)-2-Benzyl-3-(2-oxo-piperazin-4-ylsulfonyl)-propionyl-(L)-leucine Amide of (2S,3R,4S)-2-Amino-1-cyclohexyl3,4-dihydroxy-6-methylheptane;

(xxvii) (2S)-2-Benzyl-3-(2-oxo-piperazin-4-ylsulfonyl)-propionyl-(L)-(nor) leucine Amide of (2S,3R,4S)-2-Amino-1-cyclohexyl3,4-dihydroxy-6-methylheptane;

(xxviii) (2S)-2-Benzyl-3-(2-oxo-piperazin-4-ylsulfonyl)-propionyl-(L)-(2-aminothiazol-4-yl)Ala Amide of (2S,3R,4S)-2-Amino-1-cyclohexyl3,4-dihydroxy-6-methylheptane;

(xxix) (2S)-2-Benzyl-3-(2-oxo-piperazin-4-ylsulfonyl)-propionyl-(L)-methionine Amide of (2S,3R,4S)-2-Amino-1-cyclohexyl3,4-dihydroxy-6-methylheptane;

(xxx) (2S)-2-Benzyl-3-(2-oxo-piperazin-4-ylsulfonyl)-propionyl-(L)-(S-Me)Cys Amide of (2S,3R,4S)-2-Amino-1-cyclohexyl3,4-dihydroxy-6-methylheptane;

(xxxi) (2S)-2-Benzyl-3-(1-methyl-homopmperazin-4-ylsulfonyl)propionyl-(L)-(5-Thiazolyl)Ala Amide of (2S,3R,4S)-2-Amino-1-cyclohexyl3,4-dihydroxy-6-methylheptane;

(xxxii) (2S)-2-Benzyl-3-(1-methyl-homopiperazin-4-ylsulfonyl)propionyl-(L)-(2-Thiazolyl)Ala Amide of (2S,3R,4S)-2-Amino-1-cyclohexyl3,4-dihydroxy-6-methylheptane;

(xxxiii) (2S)-2-Benzyl-3-(1-methyl-homopiperazin-4-ylsulfonyl)propionyl-(L)-(1-pyrazolyl)Ala Amide of (2S,3R,4S)-2-Amino-1-cyclohexyl3,4-dihydroxy-6-methylheptane;

(xxxiv) (2S)-2-Benzyl-3-(1-methyl-homopiperazin-4-ylsulfonyl)propionyl-(L)-(3-pyrazolyl)Ala Amide of (2S,3R,4S)-2-Amino-1-cyclohexyl-3,4-dihydroxy-6-methylheptane;

(xxxv) (2S)-2-Benzyl-3-(1-methyl-homopiperazin-4-ylsulfonyl)propionyl-(L)-(1-imidazolyl)Ala Amide of (2S,3R,4S)-2-Amino-1-cyclohexyl-3, 4-dihydroxy-6-methylheptane;

(xxxvi) (2S)-2-Benzyl-3-(1-methyl-homopiperazin-4-ylsulfonyl)propionyl-(L)-leucine Amide of (2S,3R,4S)-2-Amino-1-cyclohexyl-3,4-dihydroxy-6-methylheptane;

(xxxvii) (2S)-2-Benzyl-3-(1-methyl-homopiperazin-4-ylsulfonyl)propionyl-(L)-(nor) leucine Amide of (2S,3R,4S)-2-Amino-1-cyclohexyl3,4-dihydroxy- 6-methylheptane;

(xxxviii) (2S)-2-Benzyl-3-(1-methyl-homopiperazin-4-ylsulfonyl)propionyl-(L)-(2-aminothiazol-4-yl)Ala Amide of (2S,3R,4S)-2-Amino-1-cyclohexyl-3,4-dihydroxy-6-methylheptane;

(xxxix) (2S)-2-Benzyl-3-(1-methyl-homopiperazin-4-ylsulfonyl)propionyl-(L)-methionine Amide of (2S, 3R, 4S)-2-Amino-1-cyclohexyl- 3,4-dihydroxy-6-methylheptane;

(xl) (2S)-2-Benzyl-3-(1-methyl-homopiperazin-4-ylsulfonyl)propionyl-(L)-(S-Me)Cys Amide of (2S,3R,4S)-2-Amino-1-cyclohexyl-3,4-dihydroxy-6-methylheptane;

(xli) (2S)-2-Benzyl-3-(1-methyl-homopiperazin-4-ylsulfonyl)propionyl-(L)-(4-thiazolyl)Ala Amide of (2S,3R,4S)-2-Amino-1-cyclohexyl-3,4-dihydroxy-6-methylheptane;

(xlii) (2S)-2-Benzyl-3-(morpholin-4-ylsulfonyl)propionyl-(L)-(5-Thiazolyl)Ala Amide of (2S,3R,4S)-2-Amino-1-cyclohexyl-3,4-dihdroxy- 6-methylheptane;

(xliii) (2S)-2-Benzyl-3-(morpholin-4-ylsulfonyl)propionyl-(L)-(2-Thiazolyl)Ala Amide of (2S,3R,4S)-2-Amino-1-cyclohexyl3,4-dihydroxy-6-methylheptane;

(xliv) (2S)-2-Benzyl-3-(morpholin-4-ylsulfonyl)propionyl-(L)-(1-pyrazolyl)Ala Amide of (2S,3R,4S)-2-Amino-1-cyclohexyl-3,4-dihydroxy-6-methylheptane;

(xlv) (2S)-2-Benzyl-3-(morpholin-4-ylsulfonyl)propionyl-(L)-(3-pyrazolyl)Ala Amide of (2S,3R,4S)-2-Amino-1-cyclohexyl-3,4-dihydroxy-6-methylheptane;

(xlvi) (2S)-2-Benzyl-3-(morpholin-4-ylsulfonyl)propionyl-(L)-(1-imidazolyl)Ala Amide of (2S,3R,4S)-2-Amino-1-cyclohexyl-3,4-dihydroxy-6-methylheptane;

(xlvii) (2S)-2-Benzyl-3-(morpholin-4-ylsulfonyl)propionyl-(L)-leucine Amide of (2S,3R,4S)-2-Amino-1-cyclohexyl-3,4-dihydroxy-6-methylheptane;

(xlviii) (2S)-2-Benzyl-3-(morpholin-4-ylsulfonyl)propionyl-(L)-(nor)leucine Amide of (2S,3R,4S)-2-Amino-1-cyclohexyl-3,4-dihydroxy-6-methylheptane;

(xlix) (2S)-2-Benzyl-3-(morpholin-4-ylsulfonyl)propionyl-(L)-(2-aminothiazol-4-yl)Ala Amide of (2S,3R,4S)-2-Amino-1-cyclohexyl-3,4-dihydroxy-6-methylheptane;

(l) (2S)-2-Benzyl-3-(morpholin-4-ylsulfonyl)propionyl-(L)-methionine Amide of (2S,3R,4S)-2-Amino-1-cyclohexyl-3,4-dihydroxy-6-methylheptane;

(li) (2S)-2-Benzyl-3-(morpholin-4-ylsulfonyl)propionyl-(L)-(S-Me)-Cys Amide of (2S,3R,4S)-2-Amino-1-cyclohexyl-3,4-dihydroxy-6-methylheptane;

(lii) (2S)-2-Benzyl-3-(morpholin-4-ylsulfonyl)propionyl-(L)-(4-thiazolyl)Ala Amide of (2S,3R,4S)-2-Amino-1-cyclohexyl-3,4-dihydroxy-6-methylheptane;

(liii) (2S)-2-Benzyl-3-(1-methyl-1-oxo-piperazin-4-ylsulfonyl)propionyl-(L)-(5-Thiazolyl)Ala Amide of (2S,3R,4S)-2-Amino-1-cyclohexyl-3,4-dihydroxy-6-methylheptane;

(liv) (2S)-2-Benzyl-3-(1-methyl-1-oxo-piperazin-4-ylsulfonyl)propionyl-(L)-(2-Thiazolyl)Ala Amide of (2S,3R,4S)-2-Amino-1-cyclohexyl-3,4-dihydroxy-6-methylheptane;

(lv) (2S)-2-Benzyl-3-(1-methyl-1-oxo-piperazin-4-ylsulfonyl)propionyl-(L)-(1-pyrazolyl)Ala Amide of (2S,3R,4S)-2-Amino-1-cyclohexyl-3,4-dihydroxy-6-methylheptane;

(lvi) (2S)-2-Benzyl-3-(1-metnyl-1-oxo-piperazin-4-ylsulfonyl)propionyl-(L)-(3-pyrazolyl)Ala Amide of (2S,3R,4S)-2-Amino-1-cyclohexyl-3,4-dihydroxy-6-methylheptane;

(lvii) (2S)-2-Benzyl-3-(1-methyl-1-oxo-piperazin-4-ylsulfonyl)propionyl-(L)-(1-imidazolyl)Ala Amide of (2S,3R,4S)-2-Amino-1-cyclohexyl-3,4-dihydroxy-6-methylheptane;

(lviii) (2S)-2-Benzyl-3-(1-methyl-1-oxo-piperazin-4-ylsulfonyl)propionyl-(L)-leucine Amide of (2S,3R,4S)-2-Amino-1-cyclohexyl-3,4-dihydroxy-6-methylheptane;

(lix) (2S)-2-Benzyl-3-(1-methyl-1-oxo-piperazin-4-ylsulfonyl)propionyl-(L)-(nor)leucine Amide of (2S,3R,4S)-2-Amino-1-cyclohexyl-3,4-dihydroxy-6-methylheptane;

(lx) (2S)-2-Benzyl-3-(1-methyl-1-oxo-piperazin-4-ylsulfonyl)propionyl-(L)-(2-aminothiazol-4-yl)Ala Amide of (2S,3R,4S)-2-Amino-1-cyclohexyl-3,4-dihydroxy-6-methylheptane;

(lxi) (2S)-2-Benzyl-3-(1-methyl-1-oxo-piperazin-4-ylsulfonyl)propionyl-(L)-methionine Amide of (2S,3R,4S)-2-Amino-1-cyclohexyl-3,4-dihydroxy-6-methylheptane;

(lxii) (2S)-2-Benzyl-3-(1-methyl-1-oxo-piperazin-4-ylsulfonyl)propionyl-(L)-(S-Me)Cys Amide of (2S,3R,4S)-2-Amino-1-cyclohexyl-3,4-dihydroxy-6-methylheptane;

(lxiii) (1-methylpiperazin-4-ylsulfonyl)Phe-(L)-(5-Thiazolyl) Ala Amide of (2S,3R,4S)-2-Amino-1-cyclohexyl-3,4-dihydroxy-6-methylheptane;

(lxiv) (1-methylpiperazin-4-ylsulfonyl)Phe-(L)-(2-Thiazolyl)Ala Amide of (2S,3R,4S)-2-Amino-1-cyclohexyl-3,4-dihydroxy-6-methylheptane;

(lxv) (1-methylpiperazin-4-ylsulfonyl)Phe-(L)-(1-pyrazolyl)Ala Amide of (2S,3R,4S)-2-Amino-1-cyclohexyl-3,4-dihydroxy-6-methylheptane;

(lxvi) (1-methylpiperazin-4-ylsulfonyl)Phe-(L)-(3-pyrazolyl)Ala Amide of (2S,3R,4S)-2-Amino-1-cyclohexyl-3,4-dihydroxy-6-methylheptane;

(lxvii) (1-methylpiperazin-4-ylsulfonyl)Phe-(L)-(1-imidazolyl)Ala Amide of (2S,3R,4S)-2-Amino-1-cyclohexyl-3,4-dihydroxy-6-methylheptane;

(lxviii) (1-methylpiperazin-4-ylsulfonyl)Phe-(L)-leucine Amide of (2S,3R,4S)-2-Amino-1-cyclohexyl-3,4-dihydroxy-6-methylheptane;

(lxix) (1-methylpiperazin-4-ylsulfonyl)Phe-(L)-(nor)leucine Amide of (2S,3R,4S)-2-Amino-1-cyclohexyl-3,4-dihydroxy-6-methylheptane;

(lxx) (1-methylpiperazin-4-ylsulfonyl)Phe-(L)-methionine Amide of (2S,3R,4S)-2-Amino-1-cyclohexyl-3,4-dihydroxy-6-methylheptane;

(lxxi) (1-methylpiperazin-4-ylsulfonyl)Phe-(L)-(S-Me)Cys Amide of (2S,3R,4S)-2-Amino-1-cyclohexyl-3,4-dihydroxy-6-methylheptane;

(lxxii) (piperazin-4-ylsulfonyl)Phe-(L)-(5-Thiazolyl)Ala Amide of (2S,3R,4S)-2-Amino-1-cyclohexyl-3,4-dihydroxy-6-methylheptane;

(lxxiii) (piperazin-4-ylsulfonyl)Phe-(L)-(4-Thiazolyl)Ala Amide of (2S,3R,4S)-2-Amino-1-cyclohexyl-3,4-dihydroxy-6-methylheptane;

(lxxiv) (piperazin-4-ylsulfonyl)Phe-(L)-(2-Thiazolyl)Ala Amide of (2S,3R,4S)-2-Amino-1-cyclohexyl-3,4-dihydroxy-6-methylheptane;

(lxxv) (piperazin-4-ylsulfonyl)Phe-(L)-(1-pyrazolyl)Ala Amide of (2S,3R,4S)-2-Amino-1-cyclohexyl-3,4-dihydroxy-6-methylheptane;

(lxxvi) (piperazin-4-ylsulfonyl)Phe-(L)-(3-pyrazolyl)Ala Amide of (2S,3R,4S)-2-Amino-1-cyclohexyl-3,4-dihydroxy-6-methylheptane;

(lxxvii) (piperazin-4-ylsulfonyl)Phe-(L)-(1-imidazolyl)Ala Amide of (2S,3R,4S)-2-Amino-1-cyclohexyl-3,4-dihydroxy-6-methylheptane;

(lxxviii) (piperazin-4-ylsulfonyl)Phe-(L)-leucine Amide of (2S,3R,4S)-2-Amino-1-cyclohexyl-3,4-dihydroxy-6-methylheptane;

(lxxix) (piperazin-4-ylsulfonyl)Phe-(L)-(nor)leucine Amide of (2S,3R,4S)-2-Amino-1-cyclohexyl-3,4-dihydroxy-6-methylheptane;

(lxxx) (piperazin-4-ylsulfonyl)Phe-(L)-methionine Amide of (2S,3R,4S)-2-Amino-1-cyclohexyl-3,4-dihydroxy-6-methylheptane;

(lxxxi) (piperazin-4-ylsulfonyl)Phe-(L)-(S-Me)Cys Amide of (2S,3R,4S)-2-Amino-1-cyclohexyl-3,4-dihydroxy-6-methylheptane;

(lxxxii) (2-oxo-piperazin-4-ylsulfonyl)Phe-(L)-(5-Thiazolyl)Ala Amide of (2S,3R,4S)-2-Amino-1-cyclohexyl-3,4-dihydroxy-6-methylheptane;

(lxxxiii) (2-oxo-piperazin-4-ylsulfonyl)Phe-(L)-(4-Thiazolyl)Ala Amide of (2S,3R,4S)-2-Amino-1-cyclohexyl-3,4-dihydroxy-6-methylheptane;

(lxxxiv) (2-oxo-piperazin-4-ylsulfonyl)Phe-(L)-(2-Thiazolyl)Ala Amide of (2S,3R,4S)-2-Amino-1-cyclohexyl-3,4-dihydroxy-6-methylheptane;

(lxxxv) (2-oxo-piperazin-4-ylsulfonyl)Phe-(L)-(1-pyrazolyl)Ala Amide of (2S,3R,4S)-2-Amino-1-cyclohexyl-3,4-dihydroxy-6-methylheptane;

(lxxxvi) (2-oxo-piperazin-4-ylsulfonyl)Phe-(L)-(3-pyrazolyl)Ala Amide of (2S,3R,4S)-2-Amino-1-cyclohexyl-3,4-dihydroxy-6-methylheptane;

(lxxxvii) (2-oxo-piperazin-4-ylsulfonyl)Phe-(L)-(1-imidazolyl)Ala Amide of (2S,3R,4S)-2-Amino-1-cyclohexyl-3,4-dihydroxy-6-methylheptane;

(lxxxviii) (2-oxo-piperazin-4-ylsulfonyl)Phe-(L)-leucine Amide of (2S,3R,4S)-2-Amino-1-cyclohexyl-3,4-dihydroxy-6-methylheptane;

(lxxxix) (2-oxo-piperazin-4-ylsulfonyl)Phe-(L)-(nor)leucine Amide of (2S,3R,4S)-2-Amino-1-cyclohexyl-3,4-dihydroxy-6-methylheptane;

(xc) (2-oxo-piperazin-4-ylsulfonyl)Phe-(L)-methionine Amide of (2S,3R,4S)-2-Amino-1-cyclohexyl-3,4-dihydroxy-6-methylheptane;

(xci) (2-oxo-piperazin-4-ylsulfonyl)Phe-(L)-(S-Me)Cys Amide of (2S,3R,4S)-2-Amino-1-cyclohexyl-3,4-dihydroxy-6-methylheptane;

(xcii) (1-methyl-homopiperazin-4-ylsulfonyl)Phe-(L)-(5-Thiazolyl)Ala Amide of (2S,3R,4S)-2-Amino-1-cyclohexyl-3,4-dihydroxy-6-methylheptane;

(xciii) (1-methyl-homopiperazin-4-ylsulfonyl)Phe-(L)-(2-Thiazolyl)Ala Amide of (2S,3R,4S)-2-Amino-1-cyclohexyl-3,4-dihydroxy-6-methylheptane;

(xciv) (1-methyl-homopiperazin-4-ylsulfonyl)Phe-(L)-(1-pyrazolyl)Ala Amide of (2S,3R,4S)-2-Amino-1-cyclohexyl-3,4-dihydroxy-6-methylheptane;

(xcv) (1-methyl-homopiperazin-4-ylsulfonyl)Phe-(L)-(3-pyrazolyl)Ala Amide of (2S,3R,4S)-2-Amino-1-cyclohexyl-3,4-dihydroxy-6-methylheptane;

(xcvi) (1-methyl-homopiperazin-4-ylsulfonyl)Phe-(L)-(1-imidazolyl)Ala Amide of (2S,3R,4S)-2-Amino-1-cyclohexyl-3,4-dihydroxy-6-methylheptane;

(xcvii) (1-methyl-homopiperazin-4-ylsulfonyl)Phe-(L)-leucine Amide of (2S,3R,4S)-2-Amino-1-cyclohexyl-3,4-dihydroxy-6-methylheptane;

(xcviii) (1-methyl-homopiperazin-4-ylsulfonyl)Phe-(L)-(nor)leucine Amide of (2S,3R,4S)-2-Amino-1-cyclohexyl-3,4-dihydroxy-6-methylheptane;

(xcix) (1-methyl-homopiperazin-4-ylsulfonyl)Phe-(L)-methionine Amide of (2S,3R,4S)-2-Amino-1-cyclohexyl-3,4-dihydroxy-6-methylheptane;

(c) (1-methyl-homopiperazin-4-ylsulfonyl)Phe-(L)-(S-Me)Cys Amide of (2S,3R,4S)-2-Amino-1-cyclohexyl-3,4-dihydroxy-6-methylheptane;

(ci) (1-methyl-homopiperazin-4-ylsulfonyl)Phe-(L)-(4-thiazolyl)Ala Amide of (2S,3R,4S)-2-Amino-1-cyclohexyl-3,4-dihydroxy-6-methylheptane;

(cii) (morpholin-4-ylsulfonyl)Phe-(L)-(5-Thiazolyl)Ala Amide of (2S,3R,4S)-2-Amino-1-cyclohexyl-3,4-dihydroxy-6-methylheptane;

(ciii) (morpholin-4-ylsulfonyl)Phe-(L)-(2-Thiazolyl)Ala Amide of (2S,3R,4S)-2-Amino-1-cyclohexyl-3,4-dihydroxy-6-methylheptane;

(civ) (morpholin-4-ylsulfonyl)Phe-(L)-(1-pyrazolyl)Ala Amide of (2S,3R,4S)-2-Amino-1-cyclohexyl-3,4-dihydroxy-6-methylheptane;

(cv) (morpholin-4-ylsulfonyl)Phe-(L)-(3-pyrazolyl)Ala Amide of (2S,3R,4S)-2-Amino-1-cyclohexyl-3,4-dihydroxy-6-methylheptane;

(cvi) (morpholin-4-ylsulfonyl)Phe-(L)-(1-imidazolyl)Ala Amide of (2S,3R,4S)-2-Amino-1-cyclohexyl-3,4-dihydroxy-6-methylheptane;

(cvii) (morpholin-4-ylsulfonyl)Phe-(L)-leucine Amide of (2S,3R,4S)-2-Amino-1-cyclohexyl-3,4-dihydroxy-6-methylheptane;

(cviii) (morpholin-4-ylsulfonyl)Phe-(L)-(nor)leucine Amide of (2S,3R,4S)-2-Amino-1-cyclohexyl-3,4-dihydroxy-6-methylheptane;

(cix) (morpholin-4-ylsulfonyl)Phe-(L)-methionine Amide of (2S,3R,4S)-2-Amino-1-cyclohexyl-3,4-dihydroxy-6-methylheptane;

(cx) (morpholin-4-ylsulfonyl)Phe-(L)-(S-Me)Cys Amide of (2S,3R,4S)-2-Amino-1-cyclohexyl-3,4-dihydroxy-6-methylheptane;

(cxi) (morpholin-4-ylsulfonyl)Phe-(L)-(4-thiazolyl)Ala Amide of (2S,3R,4S)-2-Amino-1-cyclohexyl-3,4-dihydroxy-6-methylheptane;

(cxii) (1-methyl-1-oxo-piperazin-4-ylsulfonyl)Phe-(L)-(5-Thiazolyl)Ala Amide of (2S,3R,4S)-2-Amino-1-cyclohexyl-3,4-dihydroxy-6-methylheptane;

(cxiii) (1-methyl-1-oxo-piperazin-4-ylsulfonyl)Phe-(L)-(4-Thiazolyl)Ala Amide of (2S,3R,4S)-2-Amino-1-cyclohexyl-3,4-dihydroxy-6-methylheptane;

(cxiv) (1-methyl-1-oxo-piperazin-4-ylsulfonyl)Phe-(L)-Thiazolyl)Ala Amide of (2S,3R,4S)-2-Amino-1-cyclohexyl-3,4-dihydroxy-6-methylheptane;

(cxv) (1-methyl-1-oxo-piperazin-4-ylsulfonyl)Phe-(L)-(1-pyrazolyl)Ala Amide of (2S,3R,4S)-2-Amino-1-cyclohexyl-3,4-dihydroxy-6-methylheptane;

(cxvi) (1-methyl-1-oxo-piperazin-4-ylsulfonyl)Phe-(L)-pyrazolyl)Ala Amide of (2S,3R,4S)-2-Amino-1-cyclohexyl-3,4-dihydroxy-6-methylheptane;

(cxvii) (1-methyl-1-oxo-piperazin-4-ylsulfonyl)Phe-(L)-(1-imidazolyl)Ala Amide of (2S,3R,4S)-2-Amino-1-cyclohexyl-3,4-dihydroxy-6-methylheptane;

(cxviii) (1-methyl-1-oxo-piperazin-4-ylsulfonyl)Phe-(L)-leucine Amide of (2S,3R,4S)-2-Amino-1-cyclohexyl-3,4-dihydroxy-6-methylheptane;

(cxix) (1-methyl-1-oxo-piperazin-4-ylsulfonyl)Phe-(L)-(nor)leucine Amide of (2S,3R,4S)-2-Amino-1-cyclohexyl-3,4-dihydroxy-6-methylheptane;

(cxx) (1-methyl-1-oxo-piperazin-4-ylsulfonyl)Phe-(L)-methionine Amide of (2S,3R,4S)-2-Amino-1-cyclohexyl-3,4-dihydroxy-6-methylheptane;

(cxxi) (1-methyl-1-oxo-piperazin-4-ylsulfonyl)Phe-(L)-(S-Me)Cys Amide of (2S,3R,4S)-2-Amino-1-cyclohexyl-3,4-dihydroxy-6-methylheptane;

(cxxii) (1-methylpiperazin-4-ylsulfonyl)-(homo)Phe-(L)-methyl-(5-Thiazolyl)Ala Amide of (2S,3R,4S)-2-Amino-1-cyclohexyl-3,4-dihydroxy-6-methylheptane;

(cxxiii) (1-methylpiperazin-4-ylsulfonyl)-(homo)Phe-(L)-N-methyl-(2-Thiazolyl)Ala Amide of (2S,3R,4S)-2-Amino-1-cyclohexyl-3,4-dihydroxy-6-methylheptane;

(cxxiv) (1-methylpiperazin-4-ylsulfonyl)-(homo)Phe-(L)-N-methyl-(1-pyrazolyl)Ala Amide of (2S,3R,4S)-2-Amino-1-cyclohexyl-3,4-dihydroxy-6-methylheptane;

(cxxv) (1-methylpiperazin-4-ylsulfonyl)-(homo)Phe-(L)-N-methyl-(3-pyrazolyl)Ala Amide of (2S,3R,4S)-2-Amino-1-cyclohexyl-3,4-dihydroxy-6-methylheptane;

(cxxvi) (1-methylpiperazin-4-ylsulfonyl)-(homo)Phe-(L)-N-methyl-(1-imidazolyl)Ala Amide of (2S,3R,4S)-2-Amino-1-cyclohexyl-3,4-dihydroxy-6-methylheptane;

(cxxvii) (1-methylpiperazin-4-ylsulfonyl)-(homo)Phe-(L)-N-methyl-leucine Amide of (2S,3R,4S)-2-Amino-1-cyclohexyl-3,4-dihydroxy-6-methylheptane;

(cxxviii) (1-methylpiperazin-4-ylsulfonyl)-(homo)Phe-(L)-N-methyl-(nor)leucine Amide of (2S,3R,4S)-2-Amino-1-cyclohexyl-3,4-dihydroxy-6-methylheptane;

(cxxix) (1-methylpiperazin-4-ylsulfonyl)-(homo)Phe-(L)-N-methyl-methionine Amide of (2S,3R,4S)-2-Amino-1-cyclohexyl-3,4-dihydroxy-6-methylheptane;

(cxxx) (1-methylpiperazin-4-ylsulfonyl)-(homo)Phe-(L)-N-methyl-(S-Me)Cys Amide of (2S,3R,4S)-2-Amino-1-cyclohexyl-3,4-dihydroxy-6-methylheptane;

(cxxxi) (piperazin-4-ylsulfonyl)-(homo)Phe-(L)-N-methyl-(5-Thiazolyl)Ala Amide of (2S,3R,4S)-2-Amino-1-cyclohexyl-3,4-dihydroxy-6-methylheptane;

(cxxxii) (piperazin-4-ylsulfonyl)-(homo)Phe-(L)-N-methyl-(4-Thiazolyl)Ala Amide of (2S,3R,4S)-2-Amino-1-cyclohexyl-3,4-dihydroxy-6-methylheptane;

(cxxxiii) (piperazin-4-ylsulfonyl)-(homo)Phe-(L)-N-methyl-(2-Thiazolyl)Ala Amide of (2S,3R,4S)-2-Amino-1-cyclohexyl-3,4-dihydroxy-6-methylheptane;

(cxxxiv) (piperazin-4-ylsulfonyl)-(homo)Phe-(L)-N-methyl-(1-pyrazolyl)Ala Amide of (2S,3R,4S)-2-Amino-1-cyclohexyl-3,4-dihydroxy-6-methylheptane;

(cxxxv) (piperazin-4-ylsulfonyl)-(homo)Phe-(L)-N-methyl-(3-pyrazolyl)Ala Amide of (2S,3R,4S)-2-Amino-1-cyclohexyl-3,4-dihydroxy-6-methylheptane;

(cxxxvi) (piperazin-4-ylsulfonyl)-(homo)Phe-(L)-N-methyl-(1-imidazolyl)Ala Amide of (2S,3R,4S)-2-Amino-1-cyclohexyl-3,4-dihydroxy-6-methylheptane;

(cxxxvii) (piperazin-4-ylsulfonyl)-(homo)Phe-(L)-N-methyl-leucine Amide of (2S,3R,4S)-2-Amino-1-cyclohexyl-3,4-dihydroxy-6-methylheptane;

(cxxxviii) (piperazin-4-ylsulfonyl)-(homo)Phe-(L)-N-methyl-(nor)leucine Amide of (2S,3R,4S)-2-Amino-1-cyclohexyl-3,4-dihydroxy-6-methylheptane;

(cxxxix) (piperazin-4-ylsulfonyl)-(homo)Phe-(L)-N-methyl-methionine Amide of (2S,3R,4S)-2-Amino-1-cyclohexyl-3,4-dihydroxy-6-methylheptane;

(cxl) (piperazin-4-ylsulfonyl)-(homo)Phe-(L)-N-methyl-Me)Cys Amide of (2S,3R,4S)-2-Amino-1-cyclohexyl-3,4-dihydroxy-6-methylheptane;

(cxli) (2-oxo-piperazin-4-ylsulfonyl)-(homo)Phe-(L)-N-methyl-(5-Thiazolyl)Ala Amide of (2S,3R,4S)-2-Amino-1-cyclohexyl-3,4-dihydroxy-6-methylheptane;

(cxlii) (2-oxo-piperazin-4-ylsulfonyl)-(homo)Phe-(L)-N-methyl-(4-Thiazolyl)Ala Amide of (2S,3R,4S)-2-Amino-1-cyclohexyl-3,4-dihydroxy-6-methylheptane;

(cxliii) (2-oxo-piperazin-4-ylsulfonyl)-(homo)Phe-(L)-N-methyl-(2-Thiazolyl)Ala Amide of (2S,3R,4S)-2-Amino-1-cyclohexyl-3,4-dihydroxy-6-methylheptane;

(cxliv) (2-oxo-piperazin-4-ylsulfonyl)-(homo)Phe-(L)-N-methyl-(1-pyrazolyl)Ala Amide of (2S,3R,4S)-2-Amino-1-cyclohexyl-3,4-dihydroxy-6-methylheptane;

(cxlv) (2-oxo-piperazin-4-ylsulfonyl)-(homo)Phe-(L)-N-methyl-(3-pyrazolyl)Ala Amide of (2S,3R,4S)-2-Amino-1-cyclohexyl-3,4-dihydroxy-6-methylheptane;

(cxlvi) (2-oxo-piperazin-4-ylsulfonyl)-(homo)Phe-(L)-N-methyl-(1-imidazolyl)Ala Amide of (2S,3R,4S)-2-Amino-1-cyclohexyl-3,4-dihydroxy-6-methylheptane;

(cxlvii) (2-oxo-piperazin-4-ylsulfonyl)-(homo)Phe-(L)-N-methyl-leucine Amide of (2S,3R,4S)-2-Amino-1-cyclohexyl-3,4-dihydroxy-6-methylheptane;

(cxlviii) (2-oxo-piperazin-4-ylsulfonyl)-(homo)Phe-(L)-N-methyl-(nor)leucine Amide of (2S,3R,4S)-2-Amino-1-cyclohexyl-3,4-dihydroxy-6-methylheptane;

(cxlix) (2-oxo-piperazin-4-ylsulfonyl)-(homo)Phe-(L)-N-methyl-methionine Amide of (2S,3R,4S)-2-Amino-1-cyclohexyl-3,4-dihydroxy-6-methylheptane;

(cl) (2-oxo-piperazin-4-ylsulfonyl)-(homo)Phe-(L)-N-methyl-(S-Me)Cys Amide of (2S,3R,4S)-2-Amino-1-cyclohexyl-3,4-dihydroxy-6-methylheptane;

(cli) (1-methyl-homopiperazin-4-ylsulfonyl)-(homo)-Phe-(L)-N-methyl-(5-Thiazolyl)Ala Amide of (2S,3R,4S)-2-Amino-1-cyclohexyl-3,4-dihydroxy-6-methylheptane;

(clii) (1-methyl-homopiperazin-4-ylsulfonyl)-(homo)-Phe-(L)-N-methyl-(2-Thiazolyl)Ala Amide of (2S,3R,4S)-2-Amino-1-cyclohexyl-3,4-dihydroxy-6-methylheptane;

(cliii) (1-methyl-homopiperazin-4-ylsulfonyl)-(homo)-Phe-(L)-N-methyl-(1-pyrazolyl)Ala Amide of (2S,3R,4S)-2-Amino-1-cyclohexyl-3,4-dihydroxy-6-methylheptane;

(cliv) (1-methyl-homopiperazin-4-ylsulfonyl)-(homo)-Phe-(L)-N-methyl-(3-pyrazolyl)Ala Amide of (2S,3R,4S)-2-Amino-1-cyclohexyl-3,4-dihydroxy-6-methylheptane;

(clv) (1-methyl-homopiperazin-4-ylsulfonyl)-(homo)-Phe-(L)-N-methyl-(1-imidazolyl)Ala Amide of (2S,3R,4S)-2-Amino-1-cyclohexyl-3,4-dihydroxy-6-methylheptane;

(clvi) (1-methyl-homopiperazin-4-ylsulfonyl)-(homo)-Phe-(L)-N-methyl-leucine Amide of (2S,3R,4S)-2-Amino-1-cyclohexyl-3,4-dihydroxy-6-methylheptane;

(clvii) (1-methyl-homopiperazin-4-ylsulfonyl)-(homo)-Phe-(L)-N-methyl-(nor)leucine Amide of (2S,3R,4S)-2-Amino-1-cyclohexyl-3,4-dihydroxy-6-methylheptane;

(clviii) (1-methyl-homopiperazin-4-ylsulfonyl)-(homo)-Phe-(L)-N-methyl-methionine Amide of (2S,3R,4S)-2-Amino-1-cyclohexyl-3,4-dihydroxy-6-methylheptane;

(clix) (1-methyl-homopiperazin-4-ylsulfonyl)-(homo)-Phe-(L)-N-methyl-(S-Me)Cys Amide of (2S,3R,4S)-2-Amino-1-cyclohexyl-3,4-dihydroxy-6-methylheptane;

(clx) (1-methyl-homopiperazin-4-ylsulfonyl)-(homo)-Phe-(L)-N-methyl-(4-thiazolyl)Ala Amide of (2S,3R,4S)-2-Amino-1-cyclohexyl-3,4-dihydroxy-6-methylheptane;

(clxi) (morpholin-4-ylsulfonyl)-(homo)Phe-(L)-N-methyl-(5-Thiazolyl)Ala Amide of (2S,3R,4S)-2-Amino-1-cyclohexyl-3,4-dihydroxy-6-methylheptane;

(clxii) (morpholin-4-ylsulfonyl)-(homo)Phe-(L)-N-methyl-(2-Thiazolyl)Ala Amide of (2S,3R,4S)-2-Amino-1-cyclohexyl-3,4-dihydroxy-6-methylheptane;

(clxiii) (morpholin-4-ylsulfonyl)-(homo)Phe-(L)-N-methyl-(1-pyrazolyl)Ala Amide of (2S,3R,4S)-2-Amino-1-cyclohexyl-3,4-dihydroxy-6-methylheptane;
(clxiv) (morpholin-4-ylsulfonyl)-(homo)Phe-(L)-N-methyl-(3-pyrazolyl)Ala Amide of (2S,3R,4S)-2-Amino-1-cyclohexyl-3,4-dihydroxy-6-methylheptane;
(clxv) (morpholin-4-ylsulfonyl)-(homo)Phe-(L)-N-methyl-(1-imidazolyl)Ala Amide of (2S,3R,4S)-2-Amino-1-cyclohexyl-3,4-dihydroxy-6-methylheptane;
(clxvi) (morpholin-4-ylsulfonyl)-(homo)Phe-(L)-N-methyl-leucine Amide of (2S,3R,4S)-2-Amino-1-cyclohexyl-3,4-dihydroxy-6-methylheptane;
(clxvii) (morpholin-4-ylsulfonyl)-(homo)Phe-(L)-N-methyl-(nor)leucine Amide of (2S,3R,4S)-2-Amino-1-cyclohexyl-3,4-dihydroxy-6-methylheptane;
(clxviii) (morpholin-4-ylsulfonyl)-(homo)Phe-(L)-N-methyl-methionine Amide of (2S,3R,4S)-2-Amino-1-cyclohexyl-3,4-dihydroxy-6-methylheptane;
(clxix) (morpholin-4-ylsulfonyl)-(homo)Phe-(L)-N-methyl-(S-Me)Cys Amide of (2S,3R,4S)-2-Amino-1-cyclohexyl-3,4-dihydroxy-6-methylheptane;
(clxx) (morpholin-4-ylsulfonyl)-(homo)Phe-(L)-N-methyl-(4-thiazolyl)Ala Amide of (2S,3R,4S)-2-Amino-1-cyclohexyl-3,4-dihydroxy-6-methylheptane;
(clxxi) (1-methyl-1-oxo-piperazin-4-ylsulfonyl)-(homo)-Phe-(L)-N-methyl-(5-Thiazolyl)Ala Amide of (2S,3R,4S)-2-Amino-1-cyclohexyl-3,4-dihydroxy-6-methylheptane;
(clxxii) (1-methyl-1-oxo-piperazin-4-ylsulfonyl)-(homo)Phe-(L)-N-methyl-(4-Thiazolyl)Ala Amide of (2S,3R,4S)-2-Amino-1-cyclohexyl-3,4-dihydroxy-6-methylheptane;
(clxxiii) (1-methyl-1-oxo-piperazin-4-ylsulfonyl)-(homo)Phe-(L)-N-methyl-(2-Thiazolyl)Ala Amide of (2S,3R,4S)-2-Amino-1-cyclohexyl-3,4-dihydroxy-6-methylheptane;
(clxxiv) (1-methyl-1-oxo-piperazin-4-ylsulfonyl)-(homo)Phe-(L)-N-methyl-(1-pyrazolyl)Ala Amide of (2S,3R,4S)-2-Amino-1-cyclohexyl-3,4-dihydroxy-6-methylheptane;
(clxxv) (1-methyl-1-oxo-piperazin-4-ylsulfonyl)-(homo)Phe-(L)-N-methyl-(3-pyrazolyl)Ala Amide of (2S,3R,4S)-2-Amino-1-cyclohexyl-3, 4-dihydroxy-6-methylheptane;
(clxxvi) (1-methyl-1-oxo-piperazin-4-ylsulfonyl)-(homo)Phe-(L)-N-methyl-(1-imidazolyl)Ala Amide of (2S,3R,4S)-2-Amino-1-cyclohexyl-3,4-dihydroxy-6-methylheptane;
(clxxvii) (1-methyl-1-oxo-piperazin-4-ylsulfonyl)-(homo)Phe-(L)-N-methyl-leucine Amide of (2S,3R,4S)-2-Amino-1-cyclohexyl-3,4-dihydroxy-6-methylheptane;
(clxxviii) (1-methyl-1-oxo-piperazin-4-ylsulfonyl)-(homo)Phe-(L)-N-methyl-(nor)leucine Amide of (2S,3R,4S)-2-Amino-1-Cyclohexyl-3,4-dihydroxy-6-methylheptane;
(clxxix) (1-methyl-1-oxo-piperazin-4-ylsulfonyl)-(homo)Phe-(L)-N-methyl-methionine Amide of (2S,3R,4S)-2-Amino-1-cyclohexyl-3,4-dihydroxy-6-methylheptane;
(clxxx) (1-methyl-1-oxo-piperazin-4-ylsulfonyl)-(homo)Phe-(L)-N-methyl-(S-Me)Cys Amide of (2S,3R,4S)-2-Amino-1-cyclohexyl-3,4-dihydroxy-6-methylheptane;
(clxxxi) (2S)-2-Benzyl-3-(1-methylpiperazin-4-ylsulfonyl)propionyl-(L)-(5-Thiazolyl)Ala Amide of (2S,3R,4S)-2-Amino-1-cyclohexyl-3,4-dihydroxy-4-(cyclopropyl)butane;
(clxxxii) (2S)-2-Benzyl-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-4-(cyclopropyl)butane;
(clxxxiii) (2S)-2-Benzyl-3-(1-methylpiperazin-4-ylsulfonyl)propionyl-(L)-(2-Thiazolyl)Ala Amide of (2S,3R,4S)-2-Amino-1-cyclohexyl-3,4-dihydroxy-4-(cyclopropyl)butane;
(clxxxiv) (2S)-2-Benzyl-3-(1-methylpiperazin-4-ylsulfonyl)propionyl-(L)-(1-pyrazolyl)Ala Amide of (2S,3R,4S)-2-Amino-1-cyclohexyl-3,4-dihydroxy-4-(cyclopropyl)butane;
(clxxxv) (2S)-2-Benzyl-3-(1-methylpiperazin-4-ylsulfonyl)propionyl-(L)-(3-pyrazolyl)Ala Amide of (2S,3R,4S)-2-Amino-1-cyclohexyl-3,4-dihydroxy-4-(cyclopropyl)butane;
(clxxxvi) (2S)-2-Benzyl-3-(1-methylpiperazin-4-ylsulfonyl)propionyl-(L)-(1-imidazolyl)Ala Amide of (2S,3R,4S)-2-Amino-1-cyclohexyl-3,4-dihydroxy-4-(cyclopropyl)butane;
(clxxxvii) (2S)-2-Benzyl-3-(1-methylpiperazin-4-ylsulfonyl)propionyl-(L)-leucine Amide of (2S,3R,4S)-2-Amino-1-cyclohexyl-3,4-dihydroxy-4-(cyclopropyl)butane;
(clxxxviii) (2S)-2-Benzyl-3-(1-methylpiperazin-4-ylsulfonyl)propionyl-(L)-(nor)leucine Amide of (2S,3R,4S)-2-Amino-1-cyclohexyl-3,4-dihydroxy-4-(cyclopropyl)butane;
(clxxxix) (2S)-2-Benzyl-3-(1-methylpiperazin-4-ylsulfonyl)propionyl-(L)-(2-aminothiazol-4-yl)Ala Amide of (2S,3R,4S)-2-Amino-1-cyclohexyl-3, 4-dihydroxy-4-(cyclopropyl)butane;
(cxc) (2S)-2-Benzyl-3-(1-methylpiperazin-4-ylsulfonyl)propionyl-(L)-methionine Amide of (2S,3R,4S)-2-Amino-1-cyclohexyl-3,4-dihydroxy-4-(cyclopropyl)butane;
(cxci) (2S)-2-Benzyl-3-(1-methylpiperazin-4-ylsulfonyl)propionyl-(L)-(S-Me)Cys Amide of (2S,3R,4S)-2-Amino-1-cyclohexyl-3,4-dihydroxy-4-(cyclopropyl)butane;
(cxcii) (2S)-2-Benzyl-3-(piperazin-4-ylsulfonyl)propionyl-(L)-(5-Thiazolyl)Ala Amide of (2S,3R,4S)-2-Amino-1-cyclohexyl-3,4-dihydroxy-4-(cyclopropyl)butane;
(cxciii) (2S)-2-Benzyl-3-(piperazin-4-ylsulfonyl)propionyl-(L)-(4-Thiazolyl)Ala Amide of (2S,3R,4S)-2-Amino-1-cyclohexyl-3,4-dihydroxy-4-(cyclopropyl)butane;
(cxciv) (2S)-2-Benzyl-3-(piperazin-4-ylsulfonyl)propionyl-(L)-(2-Thiazolyl)Ala Amide of (2S,3R,4S)-2-Amino-1-cyclohexyl-3,4-dihydroxy-4-(cyclopropyl)butane;
(cxcv) (2S)-2-Benzyl-3-(piperazin-4-ylsulfonyl)propionyl-(L)-(1-pyrazolyl)Ala Amide of (2S,3R,4S)-2-Amino-1-cyclohexyl-3,4-dihydroxy-4-(cyclopropyl)butane;
(cxcvi) (2S)-2-Benzyl-3-(piperazin-4-ylsulfonyl)propionyl-(L)-(3-pyrazolyl)Ala Amide of (2S,3R,4S)-2-Amino-1-cyclohexyl-3,4-dihydroxy-4-(cyclopropyl)butane;
(cxcvii) (2S)-2-Benzyl-3-(piperazin-4-ylsulfonyl)propionyl-(L)-(1-imidazolyl)Ala Amide of (2S,3R,4S)-2-Amino-1-cyclohexyl-3,4-dihydroxy-4-(cyclopropyl)butane;

(cxcviii) (2S)-2-Benzyl-3-(piperazin-4-ylsulfonyl) propionyl-(L)-leucine Amide of (2S,3R,4S)-2-Amino-1-cyclohexyl-3,4-dihydroxy-4-(cyclopropyl) butane;

(cxcix) (2S)-2-Benzyl-3-(piperazin-4-ylsulfonyl) propionyl-(L)-(nor) leucine Amide of (2S,3R,4S)-2-Amino-1-cyclohexyl3,4-dihydroxy-4-(cyclopropyl) butane;

(cc) (2S)-2-Benzyl-3-(piperazin-4-ylsulfonyl) propionyl-(L)-(2-aminothiazol-4-yl)Ala Amide of (2S,3R,4S)-2-Amino-1-cyclohexyl-3,4-dihydroxy-4-(cyclopropyl)-butane;

(cci) (2S)-2-Benzyl-3-(piperazin-4-ylsulfonyl) propionyl-(L)-methionine Amide of (2S,3R,4S)-2-Amino-1-cyclohexyl-3, 4-dihydroxy-4-(cyclopropyl) butane;

(ccii) (2S)-2-Benzyl-3-(piperazin-4-ylsuifonyl) propionyl-(L)-(S-Me) Cys Amide of (2S,3R,4S)-2-Amino-1-cyclohexyl-3,4-dihydroxy-4-(cyclopropyl) butane;

(cciii) (2S)-2-Benzyl-3-(2-oxo-piperazin-4-ylsulfonyl) propionyl-(L)-(5-Thiazolyl) Ala Amide of (2S,3R,4S)-2-Amino-1-cyclohexyl-3,4-dihydroxy-4-(cyclopropyl) butane;

(cciv) (2S)-2-Benzyl-3-(2-oxo-piperazin-4-ylsulfonyl) propionyl-(L)-(4-Thiazolyl) Ala Amide of (2S,3R,4S)-2-Amino-1-cyclohexyl-3,4-dihydroxy-4-(cyclopropyl) butane;

(ccv) (2S)-2-Benzyl-3-(2-oxo-piperazin-4-ylsulfonyl) propionyl-(L)-(2-Thiazolyl) Ala Amide of (2S,3R,4S)-2-Amino-1-cyclohexyl3,4-dihydroxy-4-(cyclopropyl) butane;

(ccvi) (2S)-2-Benzyl-3-(2-oxo-piperazin-4-ylsulfonyl) propionyl-(L)-(1-pyrazolyl) Ala Amide of (2S,3R,4S)-2-Amino-1-cyclohexyl-3,4-dihydroxy-4-(cyclopropyl) butane;

(ccvii) (2S)-2-Benzyl-3-(2-oxo-piperazin-4-ylsulfonyl) propionyl-(L)-(3-pyrazolyl) Ala Amide of (2S,3R,4S)-2-Amino-1-cyclohexyl-3,4-dihydroxy-4-(cyclopropyl) butane;

(ccviii) (2S)-2-Benzyl-3-(2-oxo-piperazin-4-ylsulfonyl) propionyl-(L)-(1-imidazolyl) Ala Amide of (2S,3R,4S)-2-Amino-1-cyclohexyl-3,4-dihydroxy-4-(cyclopropyl) butane;

(ccix) (2S)-2-Benzyl-3-(2-oxo-piperazin-4-ylsulfonyl) propionyl-(L)-leucine Amide of (2S,3R,4S)-2-Amino-1-cyclohexyl-3,4-dihydroxy-4-(cyclopropyl) butane;

(ccx) (2S)-2-Benzyl-3-(2-oxo-piperazin-4-ylsulfonyl) propionyl-(L)-(nor) leucine Amide of (2S,3R,4S)-2Amino-1-cyclohexyl-3,4-dihydroxy-4-(cyclopropyl)butane;

(ccxi) (2S)-2-Benzyl-3-(2-oxo-piperazin-4-ylsulfonyl) propionyl-(L)-(2-aminothiazol-4-yl) Ala Amide of (2S,3R,4S)-2-Amino-1-cyclohexyl-3,4-dihydroxy-4-(cyclopropyl) butane;

(ccxii) (2S)-2-Benzyl-3-(2-oxo-piperazin-4-ylsulfonyl) propionyl-(L)-methionine Amide of (2S,3R,4S)-2-Amino-1-cyclohexyl-3,4-dihydroxy-4-(cyclopropyl) butane;

(ccxiii) (2S)-2-Benzyl-3-(2-oxo-piperazin-4-ylsulfonyl) propionyl-(L)-(S-Me) Cys Amide of (2S,3R,4S)-2-Amino-1-cyclohexyl-3,4-dihydroxy-4-(cyclopropyl) butane;

(ccxiv) (2S)-2-Benzyl-3-(1-methyl-homopiperazin-4-ylsulfonyl) propionyl-(L)-(5-Thiazolyl) Ala Amide of (2S,3R,4S)-2-Amino-1-cyclohexyl-3,4-dihydroxy-4-(cyclopropyl) butane;

(ccxv) (2S)-2-Benzyl-3-(1-methyl-homopiperazin-4-ylsulfonyl) propionyl-(L)-(2-Thiazolyl) Ala Amide of (2S,3R,4S)-2-Amino-1-cyclohexyl-3,4-dihydroxy-4-(cyclopropyl) butane;

(ccxvi) (2S)-2-Benzyl-3-(1-methyl-homopiperazin-4-ylsulfonyl) propionyl -(L)-(1-pyrazolyl)Ala Amide of (2S,3R,4S)-2-Amino-1-cyclohexyl-3,4-dihydroxy-4-(cyclopropyl) butane;

(ccxvii) (2S)-2-Benzyl-3-(1-methyl-homopiperazin-4-ylsulfonyl) propionyl-(L)-(3-pyrazolyl) Ala Amide of (2S,3R,4S)-2-Amino-1-cyclohexyl-3,4-dihydroxy-4-(cyclopropyl) butane;

(ccxviii) (2S)-2-Benzyl-3-(1-methyl-homopiperazin-4-ylsulfonyl) propionyl-(L)-(1-imidazolyl) Ala Amide of (2S,3R,4S)-2-Amino-1-cyclohexyl-3,4-dihydroxy-4-(cyclopropyl) butane;

(ccxix) (2S)-2-Benzyl-3-(1-methyl-homopiperazin-4-ylsulfonyl) propionyl-(L)-leucine Amide of (2S,3R,4S)-2-Amino-1-cyclohexyl-3,4-dihydroxy-4-(cyclopropyl)butane;

(ccxx) (2S)-2-Benzyl-3-(1-methyl-homopiperazin-4-ylsulfonyl) propionyl -(L)-(nor) leucine Amide of (2S,3R,4S)-2-Amino-1-cyclohexyl-3,4-dihydroxy-4-(cyclopropyl) butane;

(ccxxi) (2S)-2-Benzyl-3-(1-methyl-homopiperazin-4-ylsulfonyl) propionyl -(L)-(2-aminothiazol-4-yl) Ala Amide of (2S,3R,4S)-2-Amino-1-cyclohexyl-3,4-dihydroxy-4-(cyclopropyl) butane;

(ccxxii) (2S)-2-Benzyl-3-(1-methyl-homopiperazin-4-ylsulfonyl) propionyl-(L)-methionine Amide of (2S,3R,4S)-2-Amino-1-cyclohexyl-3,4-dihydroxy-4-(cyclopropyl) butane;

(ccxxiii) (2S)-2-Benzyl-3-(1-methyl-homopiperazin-4-ylsulfonyl) propionyl-(L)-(S-Me) Cys Amide of (2S,3R,4S)-2-Amino-1-cyclohexyl-3,4-dihydroxy-4-(cyclopropyl) butane;

(ccxxiv) (2S)-2-Benzyl-3-(1-methyl-homopiperazin-4-ylsulfonyl) propionyl-(L)-(4-thiazolyl) Ala Amide of (2S,3R,4S)-2-Amino-1-cyciohexyl-3,4-dihydroxy-4-(cyclopropyl) butane;

(ccxxv) (2S)-2-Benzyl-3-(morpholin-4-ylsulfonyl) propionyl-(L)-(5-Thiazolyl)Ala Amide of (2S,3R,4S)-2-Amino-1-cyclohexyl-3,4-dihydroxy-4-(cyclopropyl) butane;

(ccxxvi) (2S)-2-Benzyl-3-(morpholin-4-ylsulfonyl) propionyl-(L)-(2-Thiazolyl) Ala Amide of (2S,3R,4S)-2-Amino-1-cyclohexyl-3,4-dihydroxy-4-(cyclopropyl) butane;

(ccxxvii) (2S)-2-Benzyl-3-(morpholin-4-ylsulfonyl)propionyl-(L)-(1-pyrazolyl)Ala Amide of (2S,3R,4S)-2-Amino-1-cyclohexyl-3,4-dihydroxy-4-(cyclopropyl) butane;

(ccxxviii) (2S)-2-Benzyl-3-(morpholin-4-ylsulfonyl) propionyl-(L)-(3-pyrazolyl) Ala Amide of (2S,3R,4S)-2-Amino-1-cyclohexyl-3,4-dihydroxy-4-(cyclopropyl) butane;

(ccxxix) (2S)-2-Benzyl-3-(morpholin-4-ylsulfonyl) propionyl-(L)-(1-imidazolyl) Ala Amide of (2S,3R,4S)-2-Amino-1-cyclohexyl-3,4-dihydroxy-4-(cyclopropyl) butane;

(ccxxx) (2S)-2-Benzyl-3-(morphotin-4-ylsulfonyl) propionyl-(L)-leucine Amide of (2S,3R,4S)-2-Amino-1-cyclohexyl-3,4-dihydroxy-4-(cyclopropyl)butane;

(ccxxxi) (2S)-2-Benzyl-3-(morpholin-4-ylsulfonyl) propionyl-(L)-(nor) leucine Amide of (2S,3R,4S)-2-Amino-1-cyclohexyl-3,4-dihydroxy-4-(cyclopropyl) butane;

(ccxxxii) (2S)-2-Benzyl-3-(morpholin-4-ylsulfonyl) propionyl-(L)-(2-aminothiazol-4-yl) Ala Amide of (2S,3R,4S)-2-Amino-1-cyclohexyl-3,4-dihydroxy-4-(cyclopropyl) butane;

(ccxxxiii) (2S)-2-Benzyl-3-(morpholin-4-ylsulfonyl) propionyl-(L)-methionine Amide of (2S,3R,4S)-2-Amino-1-cyclohexyl-3,4-dihydroxy-4-(cyclopropyl) butane;

(ccxxxiv) (2S)-2-Benzyl-3-(morpholin-4-ylsulfonyl)propionyl-(L)-(S-Me)Cys Amide of (2S,3R,4S)-2-Amino-1-cyclohexyl-3,4-dihydroxy-4-(cyclopropyl) butane;

(ccxxxv) (2S)-2-Benzyl-3-(morpholin-4-ylsulfonyl) propionyl-(L)-(4-thiazolyt) Ala Amide of (2S,3R,4S)-2-Amino-1-cyclohexyl-3,4-dihydroxy-4-(cyclopropyl) butane;

(ccxxxvi) (2S)-2-Benzyl-3-(1-methyl-1-oxo-piperazin-4-ylsulfonyl)propionyl-(L)-(5-Thiazolyl)Ala Amide (2S,3R,4S)-2-Amino-1-cyclohexyl-3,4-dihydroxy-4-(cyclopropyl) butane;

(ccxxxvii) (2S)-2-Benzyl-3-(1-methyl-1-oxo-piperazin-4-ylsulfonyl) propionyl-(L)-(4-Thiazolyl) Ala Amide of (2S,3R,4S)-2-Amino-1-cyclohexyl-3,4-dihydroxy-4-(cyclopropyl) butane;

(ccxxxviii) (2S)-2-Benzyl-3-(1-methyl-1-oxo-piperazin-4-ylsulfonyl) propionyl-(L)-(2-Thiazolyl) Ala Amide of (2S,3R,4S)-2-Amino-1-cyclohexyl-3,4-dihydroxy-4-(cyclopropyl) butane;

(ccxxxix) (2S)-2-Benzyl-3-(1-methyl-1-oxo-piperazin-4-ylsulfonyl)propionyl-(L)-(1-pyrazoiyl)Ala Amide of (2S,3R,4S)-2-Amino-1-cyclohexyl-3,4-dihydroxy-4-(cyclopropyl) butane;

(ccxl) (2S)-2-Benzyl-3-(1-methyl-1-oxo-piperazin-4-ylsulfonyl) propionyl -(L)-(3-pyrazolyl) Ala Amide of (2S,3R,4S)-2-Amino-1-cyclohexyl-3,4-dihydroxy-4-(cyclopropyl) butane;

(ccxli) (2S)-2-Benzyl-3-(1-methyl-1-oxo-piperazin-4-ylsulfonyl) propionyl -(L)-(1-imidazolyl) Ala Amide of (2S,3R,4S)-2-Amino-1-cyclohexyl-3,4-dihydroxy-4-(cyclopropyl) butane;

(ccxlii) (2S)-2-Benzyl-3-(1-methyl-1-oxo-piperazin-4-ylsulfonyl) propionyl -(L)-leucine Amide of (2S,3R,4S)-2-Amino-1-cyclohexyl-3,4-dihydroxy-4-(cyclopropyl) butane;

(ccxliii) (2S)-2-Benzyl-3-(1-methyl-1-oxo-piperazin-4-ylsulfonyl) propionyl -(L)-(nor) leucine Amide of (2S,3R,4S)-2-Amnino-1-cyclohexyl-3,4-dihydroxy-4-(cyclopropyl) butane;

(ccxliv) (2S)-2-Benzyl-3-(1-methyl-1-oxo-piperazin-4-ylsulfonyl) propionyl -(L)-(2-aminothiazol-4-yl) Ala Amide of (2S,3R,4S)-2-Amino-1-cyclohexyl-3,4-dihydroxy-4-(cyclopropyl) butane;

(ccxlv) (2S)-2-Benzyl-3-(1-methyl-1-oxo-piperazin-4-ylsulfonyl) propionyl-(L)-methionine Amide of (2S,3R,4S)-2-Amino-1-cyclohexyl-3,4-dihydroxy-4-(cyclopropyl) butane;

(ccxlvi) (2S)-2-Benzyl-3-(1-methyl-1-oxo-piperazin-4-ylsulfonyl) propionyl-(L)-(S-Me) Cys Amide of (2S,3R,4S)-2-Amino-1-cyclohexyl-3,4-dihydroxy-4-(cyclopropyl) butane;

(ccxlvii) (1-methylpiperazin-4-ylsulfonyl) Phe-(L)-(5-Thiazolyl) Ala Amide of (2S,3R,4S)-2-Amino-1-cyclohexyl-3,4-dihydroxy-4-(cyclopropyl) butane;

(ccxlviii) (1-methylpiperazin-4-ylsulfonyl)Phe-(L)-(4-Thiazolyl) Ala Amide of (2S,3R,4S)-2-Amino-1-cyclohexyl-3,4-dihydroxy-4-(cyclopropyl) butane;

(ccxlix) (1-methylpiperazin-4-ylsulfonyl) Phe-(L)-(2-Thiazolyl) Ala Amide of (2S,3R,4S)-2-Amino-1-cyclohexyl-3,4-dihydroxy-4-(cyclopropyl) butane;

(ccl) (1-methylpiperazin-4-ylsulfonyl) Phe-(L)-(1-pyrazolyl) Ala Amide of (2S, 3R, 4S)-2-Amino-1-cyclohexyl-3,4-dihydroxy-4-(cyclopropyl) butane;

(ccli) (1-methylpiperazin-4-ylsulfonyl)Phe-(L)-(3-pyrazolyl) Ala Amide of (2S,3R,4S)-2-Amino-1-cyclohexyl-3,4-dihydroxy-4-(cyclopropyl) butane;

(cclii) (1-methylpiperazin-4-ylsulfonyl)Phe-(L)-(1-imidazolyl) Ala Amide of (2S,3R,4S)-2-Amino-1-cyclohexyl-3,4-dihydroxy-4-(cyclopropyl) butane;

(ccliii) (1-methylpiperazin-4-ylsulfonyl) Phe-(L)-(nor) leucine Amide of (2S, 3R, 4S)-2-Amino-1-cyclohexyl-3,4-dihydroxy-4-(cyclopropyl) butane;

(ccliv) (1-methylpiperazin-4-ylsulfonyl)Phe-(L)-(nor) leucine Amide of (2S, 3R, 4S)-2-Amino-1-cyclohexyl-3,4-dihydroxy-4-(cyclopropyl) butane;

(cclv) (1-methylpiperazin-4-ylsulfonyl) Phe-(L)-metnionine Amide of (2S, 3R, 4S)-2-Amino-1-cyclohexyl-3,4-dihydrox-4-(cyclopropyl) butane;

(cclvi) (1-methylpiperazin-4-ylsulfonyl) Phe-(L)-(S-Me) Cys Amide of (2S,3R,4S)-2-Amino-1-cyclohexyl-3,4-dihydroxy-4-(cyclopropyl) butane;

(cclvii) (piperazin-4-ylsulfonyl) Phe-(L)-(5-Thiazolyl) Ala Amide of (2S,3R,4S)-2-Amino-1-cyclohexyl-3,4-dihydroxy-4-(cyclopropyl) butane;

(cclviii) (piperazin-4-ylsulfonyl) Phe-(L)-(4-Thiazolyl) Ala Amide of (2S,3R,4S)-2-Amino-1-cyclohexyl-3,4-dihydroxy-4-(cyclopropyl) butane;

(cclix) (piperazin-4-ylsulfonyl) Phe-(L)-(2-Thiazolyl) Ala Amide of (2S,3R,4S)-2-Amino-1-cyclohexyl-3,4-dihydroxy-4-(cyclopropyl) butane;

(cclx) (piperazin-4-ylsulfonyl) Phe-(L)-(1-pyrazolyl) Ala Amide of (2S,3R,4S)-2-Amino-1-cyclohexyl-3,4-dihydroxy-4-(cyclopropyl) butane;

(cclxi) (piperazin-4-ylsulfonyl) Phe-(L)-(3-pyrazolyl) Ala Amide of (2S,3R,4S)-2-Amino-1-cyclohexyl-3,4-dihydroxy-4-(cyclopropyl) butane;

(cclxii) (piperazin-4-ylsulfonyl) Phe-(L)-(1-imidazolyl) Ala Amide of (2S,3R,4S)-2-Amino-1-cyclohexyl-3,4-dihydroxy-4-(cyclopropyl) butane;

(cclxiii) (piperazin-4-ylsulfonyl) Phe-(L)-leucine Amide of (2S,3R,4S)-2-Amino-1-cyclohexyl-3,4-dihydroxy-4-(cyclopropyl) butane;

(cclxiv) (piperazin-4-ylsuifonyl) Phe-(L)-(nor) leucine Amide of (2S, 3R, 4S)-2-Amino-1-cyclohexyl-3,4-dihydroxy-4-(cyclopropyl) butane;

(cclxv) (piperazin-4-ylsulfonyl) Phe-(L)-methionine Amide of (2S,3R,4S)-2-Amino-1-cyclohexyl-3,4-dihydroxy-4-(cyclopropyl) butane;

(cclxvi) (piperazin-4-ylsulfonyl) Phe-(L)-(S-Me) Cys Amide of (2S,3R,4S)-2-Amino-1-cyclohexyl-3,4-dihydroxy-4-(cyclopropyl) butane;

(cclxvii) (2-oxo-piperazin-4-ylsulfonyl) Phe-(L)-(b-Thiazolyl)Ala Amide of (2S,3R,4S)-2-Amino-1-cyclonexyl-3,4-dihydroxy-4-(cyclopropyl) butane;

(cclxviii) (2-oxo-piperazin-4-ylsulfonyl) Phe-(L)-(4-Thiazolyl) Ala Amide of (2S, 3R, 4S)-2-Amino-1-cyclonexyl-3,4-dihydroxy-4-(cyclopropyl) butane;

(cclxix) (2-oxo-piperazin-4-ylsulfonyl) Phe-(L)-(2-Thiazolyl) Ala Amide of (2S,3R,4S)-2-Amino-1-cyclohexyl-3,4-dihydroxy-4-(cyclopropyl) butane;

(cclxx) (2-oxo-piperazin-4-ylsulfonyl) Phe-(L)-(1-pyrazolyl) Ala Amide of (2S,3R,4S)-2-Amino-1-cyclohexyl-3,4-dihydroxy-4-(cyclopropyl) butane;

(cclxxi) (2-oxo-piperazin-4-ylsulfonyl) Phe-(L)-(3-pyrazolyl)Ala Amide of (2S,3R,4S)-2-Amino-1-cyclohexyl-3,4-dihydroxy-4-(cyclopropyl) butane;

(cclxxii) (2-oxo-piperazin-4-ylsulfonyl)Phe-(L)-(1-imidazolyl) Ala Amide of (2S,3R,4S)-2-Amino-1-cyclohexyl-3,4-dihydroxy-4-(cyclopropyl) butane;

(cclxxiii) (2-oxo-piperazin-4-ylsulfonyl) Phe-(L)-leucine Amide of (2S,3R,4S)-2-Amino-1-cyclohexyl-3,4-dihydroxy-4-(cyclopropyl) butane;

(cclxxiv) (2-oxo-piperazin-4-ylsulfonyl) Phe-(L)-(nor) leucine Amide of (2S,3R,4S)-2-Amino-1-cyclohexyl-3,4-dihydroxy-4-(cyclopropyl) butane;

(cclxxv) (2-oxo-piperazin-4-ylsulfonyl) Phe-(L)-methionine Amide of (2S,3R,4S)-2-Amino-1-cyclohexyl-3,4-dihydroxy-4-(cyclopropyl) butane;

(cclxxvi) (2-oxo-piperazin-4-ylsulfonyl) Phe-(L)-(S-Me) Cys Amide of (2S,3R,4S)-2-Amino-1-cyclohexyl-3,4-dihydroxy-4-(cyclopropyl) butane;

(cclxxvii) (1-methyl-homopiperazin-4-ylsulfonyl) Phe-(L)-(5-Thiazolyl) Ala Amide of (2S,3R,4S)-2-Amino-1-cyclohexyl-3,4-dihydroxy-4-(cyclopropyl) butane;

(cclxxviii) (1-methyl-homopiperazin-4-ylsulfonyl) Phe-(L)-(2-Thiazolyl) Ala Amide of (2S,3R,4S)-2-Amino-1-cyclohexyl-3,4-dihydroxy-4-(cyclopropyl) butane;

(cclxxix) (1-methyl-homopiperazin-4-ylsulfonyl) Phe-(L)-(1-pyrazolyl)Ala Amide of (2S,3R,4S )-2-Amino-1-cyclohexyl-3,4-dihydroxy-4-(cyclopropyl) butane;

(cclxxx) (1-methyl-homopiperazin-4-ylsulfonyl) Phe-(L)-(3-pyrazolyl) Ala Amide of (2S,3R,4S)-2-Amino-1-cyclohexyl-3,4-dihydroxy-4-(cyclopropyl) butane;

(cclxxxi) (1-methyl-homopiperazin-4-ylsulfonyl) Phe-(L)-(1-imidazolyl) Ala Amide of (2S,3R,4S)-2-Amino-1-cyclohexyl-3,4-dihydroxy-4-(cyclopropyl) butane;

(cclxxxii) (1-methyl-homopiperazin-4-ylsulfonyl) Phe-(L)-leucine Amide of (2S,3R,4S)-2-Amino-1-cyclohexyl-3,4-dihydroxy-4-(cyclopropyl) butane;

(cclxxxiii) (1-methyl-homopiperazin-4-ylsulfonyl) Phe-(L)-(nor) leucine Amide of (2S,3R,4S)-2-Amino-1-cyclohexyl-3,4-dihydroxy-4-(cyclopropyl) butane;

(cclxxxiv) (1-methyl-homopiperazin-4-ylsulfonyl) Phe-(L)-methionine Amide of (2S,3R,4S)-2-Amino-1-cyclohexyl-3,4-dihydroxy-4-(cyclopropyl) butane;

(cclxxxv) (1-methyl-homopiperazin-4-ylsulfonyl) Phe-(L)-(S-Me) Cys Amide of (2S,3R,4S)-2-Amino-1-cyclohexyl-3,4-dihydroxy-4-(cyclopropyl) butane;

(cclxxxvi) (1-methyl-homopiperazin-4-ylsulfonyl) Phe-(L)-(4-thiazolyl) Ala Amide of (2S, 3R, 4S)-2-Amino-1-cyclohexyl-3,4-dihydroxy-4-(cyclopropyl) butane;

(cclxxxvii) (morpholin-4-ylsulfonyl) Phe-(L)-(5-Thiazolyl) Ala Amide of (2S, 3R, 4S)-2-Amino-1-cyclohexyl-3,4-dihydroxy-4-(cyclopropyl) butane;

(cclxxxviii) (morpholin-4-ylsulfonyl)Phe-(L)-(2-Thiazolyl) Ala Amide of (2S,3R,4S)-2-Amino-1-cyclohexyl-3,4-dihydroxy-4-(cyclopropyl) butane;

(cclxxxix) (morpholin-4-ylsulfonyl) Phe-(L)-(1-pyrazolyl) Ala Amide of (2S,3R,4S)-2-Amino-1-cyclohexyl-3,4-dihydroxy-4-(cyclopropyl) butane;

(ccxc) (morpholin-4-ylsulfonyl) Phe-(L)-(3-pyrazolyl)Ala Amide of (2S,3R,4S)-2-Amino-1-cyclohexyl-3,4-dihydroxy-4-(cyclopropyl) butane;

(ccxci) (morpholin-4-ylsulfonyl)Phe-(L)-(1-imidazolyl)Ala Amide of (2S,3R,4S)-2-Amino-1-cyclohexyl-3,4-dihydroxy-4-(cyclopropyl) butane;

(ccxcii) (morpholin-4-ylsulfonyl) Phe-(L)-leucine Amide of (2S,3R,4S)-2-Amino-1-cyclohexyl-3,4-dihydroxy-4-(cyclopropyl) butane;

(ccxciii) (morpholin-4-ylsulfonyl) Phe-(L)-(nor) leucine Amide of (2S,3R,4S)-2-Amino-1-cyclohexyl-3,4-dihydroxy-4-(cyclopropyl) butane;

(ccxciv) (morpholin-4-ylsulfonyl) Phe-(L)-methionine Amide of (2S,3R,4S)-2-Amino-1-cyclohexyl-3,4-dihydroxy-4-(cyclopropyl) butane;

(ccxcv) (morpholin-4-ylsulfonyl) Phe-(L)-(S-Me) Cys Amide of (2S,3R,4S)-2-Amino-1-cyclohexyl-3,4-dihydroxy--4-(cyclopropyl) butane;

(ccxcvi) (morpholin-4-ylsulfonyl) Phe-(L)-(4-thiazolyl) Ala Amide of (2S,3R,4S)-2-Amino-1-cyclohexyl-3,4-dihydroxy-4-(cyclopropyl) butane;

(ccxcvii) (1-methyl-1-oxo-piperazin-4-ylsulfonyl) Phe-(L)-(5-Thiazolyl) Ala Amide of (2S,3R,4S)-2-Amino-1-cyclohexyl-3,4-dihydroxy-4-(cyclopropyl) butane;

(ccxcviii) (1-methyl-1-oxo-piperazin-4-ylsulfonyl) Phe-(L)-(4-Thiazolyl) Ala Amide of (2S,3R,4S)-2-Amino-1-cyclohexyl-3,4-dihydroxy-4-(cyclopropyl) butane;

(ccxcix) (1-methyl-1-oxo-piperazin-4-ylsulfonyl) Phe-(L)-(2-Thiazolyl) Ala Amide of (2S,3R,4S)-2-Amino-1-cyclohexyl-3,4-dihydroxy-4-(cyclopropyl) butane;

(ccc) (1-methyl-1-oxo-piperazin-4-ylsulfonyl) Phe-(L)-(1-pyrazolyl) Ala Amide of (2S,3R,4S)-2-Amino-1-cyclohexyl-3,4-dihydroxy-4-(cyclopropyl) butane;

(ccci) (1-methyl-1-oxo-piperazin-4-ylsulfonyl) Phe-(L)-(3-pyrazolyl) Ala Amide of (2S,3R,4S)-2-Amino-1-cyclohexyl-3,4-dihydroxy-4-(cyclopropyl) butane;

(cccii) (1-methyl-1-oxo-piperazin-4-ylsulfonyl) Phe-(L)-(1-imidazolyl)Ala Amide of (2S,3R,4S)-2-Amino-1-cyclohexyl-3,4-dihydroxy-4-(cyclopropyl) butane;

(ccciii) (1-methyl-1-oxo-piperazin-4-ylsulfonyl) Phe-(L)-leucine Amide of (2S,3R,4S)-2-Amino-1-cyclohexyl-3,4-dihydroxy-4-(cyclopropyl) butane;

(ccciv) (1-methyl-1-oxo-piperazin-4-ylsulfonyl) Phe-(L)-(nor) leucine Amide of (2S,3R,4S)-2-Amino-1-cyclohexyl-3,4-dihydroxy-4-(cyclopropyl) butane;

(cccv) (1-methyl-1-oxo-piperazin-4-ylsulfonyl) Phe-(L)-methionine Amide of (2S,3R,4S)-2-Amino-1-cyclohexyl-3,4-dihydroxy-4-(cyclopropyl) butane;

(cccvi) (1-methyl-1-oxo-piperazin-4-ylsulfonyl) Phe-(L)-(S-Me) Cys Amide of (2S,3R,4S)-2-Amino-1-cyclohexyl-3,4-dihydroxy-4-(cyclopropyl) butane;

(cccvii) (1-methylpiperazin-4-ylsulfonyl)-(homo) Phe-(L)-N-methyl-(5-Thiazolyl) Ala Amide of (2S, 3R, 4S)-2-Amino-1-cyclohexyl-3,4-dihydroxy-4-(cyclopropyl) butane;

(cccviii) (1-methylpiperazin-4-ylsulfonyl)-(homo) Phe-(L)-N-methyl-(4-Thiazolyl) Ala Amide of (2S,3R,4S)-2-Amino-1-cyclohexyl-3,4-dihydroxy-4-(cyclopropyl) butane;

(cccix) (1-methylpiperazin-4-ylsulfonyl)-(homo) Phe-(L)-N-methyl-(2-Thiazolyl)Ala Amide of (2S,3R,4S)-2-Amino-1-cyclohexyl-3,4-dihydroxy-4-(cyclopropyl) butane;

(cccx) (1-methylpiperazin-4-ylsulfonyl)-(homo) Phe-(L)-N-methyl-(1-pyrazolyl) Ala Amide of (2S,3R,4S)-2-Amino-1-cyclohexyl-3,4-dihydroxy-4-(cyclopropyl) butane;

(cccxi) (1-methylpiperazin-4-ylsulfonyl)-(homo) Phe-(L)-N-methyl-(3-pyrazolyl) Ala Amide of (2S,3R,4S)-2-Amino-1-cyclohexyl-3,4-dihydroxy-4-(cyclopropyl) butane;

(cccxii) (1-methylpiperazin-4-ylsulfonyl)-(homo)Phe-(L)-N-methyl-(1-imidazolyl) Ala Amide of (2S,3R,4S)-2-Amino-1-cyclohexyl-3,4-dihydroxy-4-(cyclopropyl) butane;

(cccxiii) (1-methylpiperazin-4-ylsulfonyl)-(homo) Phe-(L)-N-methyl-leucine Amide of (2S,3R,4S)-2-Amino-1-cyclohexyl-3,4-dihydroxy-4-(cyclopropyl) butane;

(cccxiv) (1-methylpiperazin-4-ylsulfonyl)-(homo) Phe-(L)-N-methyl-(nor) leucine Amide of (2S,3R,4S)-2-Amino-1-cyclohexyl-3,4-dihydroxy-4-(cyclopropyl) butane;

(cccxv) (1-methylpiperazin-4-ylsulfonyl)-(homo) Phe-(L)-N-methyl-methionine Amide of (2S,3R,4S)-2-Amino-1-cyclohexyl-3,4-dihydroxy-4-(cyclopropyl) butane;

(cccxvi) (1-methylpiperazin-4-ylsulfonyl)-(homo) Phe-(L)-N-methyl-(S-Me) Cys Amide of (2S,3R,4S)-2-Amino-1-cyclohexyl-3,4-dihydroxy-4-(cyclopropyl) butane;

(cccxvii) (piperazin-4-ylsulfonyl)-(homo) Phe-(L)-N-methyl-(5-Thiazolyl) Ala Amide of (2S,3R,4S)-2-Amino-1-cyclohexyl-3,4-dihydroxy-4-(cyclopropyl) butane;

(cccxviii) (piperazin-4-ylsulfonyl)-(homo) Phe-(L)-N-methyl-(4-Thiazolyl) Ala Amide of (2S,3R,4S)-2-Amino-1-cyclohexyl-3,4-dihydroxy-4-(cyclopropyl) butane;

(cccxix) (piperazin-4-ylsulfonyl)-(homo) Phe-(L)-N-methyl-(2-Thiazolyl) Ala Amide of (2S,3R,4S)-2-Amino-1-cyclohexyl-3,4-dihydroxy-4-(cyclopropyl) butane;

(cccxx) (piperazin-4-ylsulfonyl)-(homo) Phe-(L)-N-methyl-(1-pyrazolyl)Ala Amide of (2S,3R,4S)-2-Amino-1-cyclohexyl-3,4-dihydroxy-4-(cyclopropyl) butane;

(cccxxi) (piperazin-4-ylsulfonyl)-(homo) Phe-(L)-N-methyl-(3-pyrazolyl) Ala Amide of (2S,3R,4S)-2-Amino-1-cyclohexyl-3,4-dihydroxy-4-(cyclopropyl) butane;

(cccxxii) (piperazin-4-ylsulfonyl)-(homo) Phe-(L)-N-methyl-(1-imidazolyl)Ala Amide of (2S,3R,4S)-2-Amino-1-cyclohexyl-3,4-dihydroxy-4-(cyclopropyl) butane;

(cccxxiii) (piperazin-4-ylsulfonyl)-(homo) Phe-(L)-N-methyl-leucine Amide of (2S,3R,4S)-2-Amino-1-cyclohexyl-3,4-dihydroxy-4-(cyclopropyl) butane;

(cccxxiv) (piperazin-4-ylsulfonyl)-(homo) Phe-(L)-N-methyl-(nor) leucine Amide of (2S,3R,4S)-2-Amino-1-cyclohexyl-3,4-dihydroxy-4-(cyclopropyl) butane;

(cccxxv) (piperazin-4-ylsulfonyl)-(homo) Phe-(L)-N-methyl-methionine Amide of (2S,3R,4S)-2-Amino-1-cyclohexyl-3,4-dihydroxy-4-(cyclopropyl) butane;

(cccxxvi) (piperazin-4-ylsulfonyl)-(homo) Phe-(L)-N-methyl-(S-Me) Cys Amide of (2S,3R,4S)-2-Amino-1-cyclohexyl-3,4-dihydroxy-4-(cyclopropyl) butane;

(cccxxvii) (2-oxo-piperazin-4-ylsulfonyl)-(homo) Phe-(L)-N-methyl-(5-Thiazolyl) Ala Amide of (2S, 3R, 4S)-2-Amino-1-cyclohexyl-3,4-dihydroxy-4-(cyclopropyl) butane;

(cccxxviii) (2-oxo-piperazin-4-ylsulfonyl)-(homo) Phe-(L)-N-methyl-(4-Thiazolyl) Ala Amide of (2S,3R,4S)-2-Amino-1-cyciohexyl-3,4-dihydroxy-4-(cyclopropyl) butane;

(cccxxix) (2-oxo-piperazin-4-ylsulfonyl)-(homo) Phe-(L)-N-methyl-(2-Thiazolyl) Ala Amide of (2S,3R,4S)-2-Amino-1-cyclohexyl-3,4-dihydroxy-4-(cyclopropyl) butane;

(cccxxx) (2-oxo-piperazin-4-ylsulfonyl)-(homo) Phe-(L)-N-methyl-(1-pyrazolyl) Ala Amide of (2S,3R,4S)-2-Amino-1-cyclohexyl-3,4-dihydroxy-4-(cyclopropyl) butane;

(cccxxxi) (2-oxo-piperazin-4-ylsulfonyl)-(homo) Phe-(L)-N-methyl-(3-pyrazolyl) Ala Amide of (2S,3R 4S)-2-Amino-1-cyclohexyl-3,4-dihydroxy-4-(cyclopropyl) butane;

(cccxxxii) (2-oxo-piperazin-4-ylsulfonyl)-(homo) Phe-(L)-N-methyl-(1-imidazolyl)Ala Amide of (2S,3R,4S)-2-Amino-1-cyclohexyl-3,4-dihydroxy-4-(cyclopropyl) butane;

(cccxxxiii) (2-oxo-piperazin-4-ylsulfonyl)-(homo)Phe-(L)-N-methyl-leucine Amide of (2S,3R,4S)-2-Amino-1-cyclohexyl-3,4-dihydroxy-4-(cyclopropyl) butane;

(cccxxxiv) (2-oxo-piperazin-4-ylsulfonyl)-(homo) Phe-(L)-N-methyl-(nor) leucine Amide of (2S,3R,4S)-2-Amino-1-cyclohexyl-3,4-dihydroxy-4-(cyclopropyl) butane;

(cccxxxv) (2-oxo-piperazin-4-ylsulfonyl)-(homo) Phe-(L)-N-methyl-methionine Amide of (2S,3R,4S)-2-Amino-1-cyclohexyl-3,4-dihydroxy-4-(cyclopropyl) butane;

(cccxxxvi) (2-oxo-piperazin-4-ylsulfonyl)-(homo) Phe-(L)-N-methyl-(S-Me) Cys Amide of (2S,3R,4S)-2-Amino-1-cyclohexyl-3,4-dihydroxy-4-(cyclopropyl) butane;

(cccxxxvii) (1-methyl-homopiperazin-4-ylsulfonyl)-(homo) Phe-(L)-N-methyl-(5-Thiazolyl) Ala Amide of (2S,3R,4S)-2-Amino-1-cyclohexyl-3,4-dihydroxy-4-(cyclopropyl) butane;

(cccxxxviii) (1-methyl-homopiperazin-4-ylsulfonyl)-(homo) Phe-(L)-N-methyl-(2-Thiazolyl) Ala Amide of (2S,3R,4S)-2-Amino-1-cyclohexyl-3,4-dihydroxy-4-(cyclopropyl) butane;

(cccxxxix) (1-methyl-homopiperazin-4-ylsulfonyl)-(homo) Phe-(L)-N-methyl-(1-pyrazolyl) Ala Amide of (2S,3R,4S)-2-Amino-1-cyclohexyl-3,4-dihydroxy-4-(cyciopropyl) butane;

(cccxl) (1-methyl-homopiperazin-4-ylsulfonyl)-(homo) Phe-(L)-N-methyl-(3-pyrazolyl)Ala Amide of (2S,3R,4S)-2-Amino-1-cyclohexyl-3,4-dihydroxy-4-(cyclopropyl) butane;

(cccxli) (1-methyl-homopiperazin-4-ylsulfonyl)-(homo) Phe-(L)-N-methyl-(1-imidazolyl)Ala Amide of (2S,3R,4S)-2-Amino-1-cyclohexyl-3,4-dihydroxy-4-(cyclopropyl) butane;

(cccxlii) (1-methyl-homopiperazln-4-ylsulfonyl)-(homo) Phe-(L)-N-methyl-leucine Amide of (2S,3R,4S)-2-Amino-1-cyclohexyl-3,4-dihydroxy-4-(cyclopropyl) butane;

(cccxliii) (1-methyl-homopiperazin-4-ylsulfonyl)-(homo) Phe-(L)-N-methyl-(nor) leucine Amide of (2S, 3R; 4S)-2-Amino-1-cyclohexyl-3,4-dihydroxy-4-(cyclopropyl) butane;

(cccxliv) (1-methyl-homopiperazin-4-ylsulfonyl)-(homo) Phe-(L)-N-methyl-methionine Amide of (2S,3R,4S)-2-Amino-1-cyclohexyl-3,4-dihydroxy-4-(cyclopropyl) butane;

(cccxlv) (1-methyl-homopiperazin-4-ylsulfonyl)-(homo) Phe-(L)-N-methyl-(S-Me) Cys Amide of (2S,3R,4S)-2-Amino-1-cyciohexyl-3,4-dihydroxy-4-(cyclopropyl) butane;

(cccxlvi) (1-methyl-homopiperazin-4-ylsulfonyl)-(homo) Phe-(L)-N-methyl-(4-thiazolyl)Ala Amide of (2S,3R,4S)-2-Amino-1-cyclohexyl-3,4-dihydroxy-4-(cyclopropyl) butane;

(cccxlvii) (morpholin-4-ylsulfonyl)-(homo) Phe-(L) N-methyl-(5-Thiazolyl) Ala Amide of (2S,3R,4S)-2-Amino-1-cyclohexyl-3,4-dihydroxy-4-(cyclopropyl) butane;

(cccxlviii) (morpholin-4-ylsulfonyl)-(homo)Phe-(L)-N-methyl-(2-Thiazolyl)Ala Amide of (2S,3R,4S)-2-Amino-1-cyclohexyl-3,4-dihydroxy-4-(cyclopropyl)-butane;

(cccxlix) (morpholin-4-ylsulfonyl)-(homo)Phe-(L)-N-methyl-(1-pyrazolyl)Ala Amide of (2S,3R,4S)-2-Amino-1-cyclohexyl-3,4-dihydroxy-4-(cyclopropyl)-butane;

(cccl) (morpholin-4-ylsulfonyl)-(homo)Phe-(L)-N-methyl-(3-pyrazolyl)Ala Amide of (2S,3R,4S)-2-Amino-1-cyclohexyl-3,4-dihydroxy-4-(cyclopropyl)butane;

(cccli) (morpholin-4-ylsulfonyl)-(homo)Phe-(L)-N-methyl-(1-imidazolyl)Ala Amide of (2S,3R,4S)-2-Amino-1-cyclohexyl-3,4-dihydroxy-4-(cyclopropyl)butane;

(ccclii) (morpholin-4-ylsulfonyl)-(homo)Phe-(L)-N-methylleucine Amide of (2S,3R,4S)-2-Amino-1-cyclohexyl-3,4-dihydroxy-4-(cyclopropyl)butane;

(cccliii) (morpholin-4-ylsulfonyl)-(homo)Phe-(L)-N-methyl-(nor)leucine Amide of (2S,3R,4S)-2-Amino-1-cyclohexyl-3,4-dihydroxy-4-(cyclopropyl)butane;

(cccliv) (morpholin-4-ylsulfonyl)-(homo)Phe-(L)-N-methylmethionine Amide of (2S,3R,4S)-2-Amino-1-cyclohexyl-3,4-dihydroxy-4-(cyclopropyl)butane;

(ccclv) (morpholin-4-ylsulfonyl)-(homo)Phe-(L)-N-methyl-(S-Me)Cys Amide of (2S,3R,4S)-2-Amino-1-cyclohexyl-3,4-dihydroxy-4-(cyclopropyl)butane;

(ccclvi) (morpholin-4-ylsulfonyl)-(homo)Phe-(L)-N-methyl-(4-thiazolyl)Ala Amide of (2S,3R,4S)-2-Amino-1-cyclohexyl-3,4-dihydroxy-4-(cyclopropyl)butane;

(ccclvii) (1-methyl-1-oxo-piperazin-4-ylsulfonyl)-(homo)Phe-(L)-N-methyl-(5-Thiazolyl)Ala Amide of (2S,3R,4S)-2-Amino-1-cyclohexyl-3,4-dihydroxy-4-(cyclopropyl)butane;

(ccclviii) (1-methyl-1-oxo-piperazin-4-ylsulfonyl)-(homo)Phe-(L)-N-methyl-(4-Thiazolyl)Ala Amide of (2S,3R,4S)-2-Amino-1-cyclohexyl-3,4-dihydroxy-4-(cyclopropyl)butane;

(ccclix) (1-methyl-1-oxo-piperazin-4-ylsulfonyl)-(homo)Phe-(L)-N-methyl-(2-Thiazolyl)Ala Amide of (2S,3R,4S)-2-Amino-1-cyclohexyl-3,4-dihydroxy-4-(cyclopropyl)butane;

(ccclx) (1-methyl-1-oxo-piperazin-4-ylsulfonyl)-(homo)Phe-(L)-N-methyl-(1-pyrazolyl)Ala Amide of (2S,3R,4S)-2-Amino-1-cyclohexyl-3,4-dihydroxy-4-(cyclopropyl)butane;

(ccclxi) (1-methyl-1-oxo-piperazin-4-ylsulfonyl)-(homo)Phe-(L)-N-methyl-(3-pyrazolyl)Ala Amide of (2S,3R,4S)-2-Amino-1-cyclohexyl-3,4-dihydroxy-4-(cyclopropyl)butane;

(ccclxii) (1-methyl-1-oxo-piperazin-4-ylsulfonyl)-(homo)Phe-(L)-N-methyl-(1-imidazolyl)Ala Amide of (2S,3R,4S)-2-Amino-1-cyclohexyl-3, 4-dihydroxy-4-(cyclopropyl)butane;

(ccclxiii) (1-methyl-1-oxo-piperazin-4-ylsulfonyl)-(homo)Phe-(L)-N-methyl-leucine Amide of (2S,3R,4S)-2-Amino-1-cyclohexyl-3,4-dihydroxy-4-(cyclopropyl)butane;

(ccclxiv) (1-methyl-1-oxo-piperazin-4-ylsulfonyl)-(homo)Phe-(L)-N-methyl-(nor)leucine Amide of (2S,3R,4S)-2-Amino-1-cyclohexyl-3,4-dihydroxy-4-(cyclopropyl)butane;

(ccclxv) (1-methyl-1-oxo-piperazin-4-ylsulfonyl)-(homo)Phe-(L)-N-methyl-methionine Amide of (2S,3R,4S)-2-Amino-1-cyclohexyl-3,4-dihydroxy-4-(cyclopropyl)butane;

(ccclxvi) (1-methyl-1-oxo-piperazin-4-ylsulfonyl)-(homo)Phe-(L)-N-methyl-(S-Me)Cys Amide of (2S,3R,4S)-2-Amino-1-cyclohexyl-3,4-dihydroxy-4-(cyclopropyl)butane;

(ccclxvii) (1-methylpiperazin-4-ylsulfonyl)Phe-(L)-(2-aminothiazol-4-yl)Ala Amide of (2S,3R,4S)-2-Amino-1-cyclohexyl- 3,4-dihydroxy-4-(cyclopropyl)butane;

(ccclxviii) (piperazin-4-ylsulfonyl)Phe-(L)-(2-aminothiazol-4-yl)Ala Amide of (2S,3R,4S)-2-Amino-1-cyclohexyl-3,4-dihydroxy-4-(cyclopropyl)butane;

(ccclxix) (2-oxo-piperazin-4-ylsulfonyl)Phe-(L)-(2-aminothiazol-4-yl)Ala Amide of (2S,3R,4S)-2-Amino-1-cyclohexyl-3,4-dihydroxy-4-(cyclopropyl)butane;

(ccclxx) (1-methyl-homopiperazin-4-ylsulfonyl)Phe-(L)-(2-aminothiazol-4-yl)Ala Amide of (2S,3R,4S)-2-Amino-1-cyclohexyl-3,4-dihydroxy-4-(cyclopropyl)butane;

(ccclxxi) (morpholin-4-ylsulfonyl)Phe-(L)-(2-aminothiazol-4-yl)Ala Amide of (2S,3R,4S)-2-Amino-1-cyclohexyl-3,4-dihydroxy-4-(cyclopropyl)butane;

(ccclxxii) (1-methyl-1-oxo-piperazin-4-ylsulfonyl)Phe-(L)-(2-aminothiazol-4-yl)Ala Amide of (2S,3R,4S)-2-Amino-1-cyclohexyl-3,4-dihydroxy-4-(cyclopropyl)butane;

(ccclxxiii) (1-methylpiperazin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxiv) (piperazin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxv) (2-oxo-piperazin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxvi) (1-methyl-homopiperazin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxvii) (morpholin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxviii) (1-methyl-1-oxo-piperazin-4-ylsulfonyl)-(homo)Phe-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxix) (2S)-2-(Napth-1-ylmethyl)-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-6-methylheptane;

(ccclxxx) (morpholin-4-ylsulfonyl) (1-napthyl)ala-(L)-N-methyl-(2-aminothiazol-4-yl)Ala Amide of (2S,3R,4S)-2-Amino-1-cyclohexyl-3,4-dihydroxy-4-(cyclopropyl)butane;

(ccclxxxi) (2S)-2-(Napth-1-ylmethyl)-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-4-(cyclopropyl)butane.

EXAMPLE 15

Alternative Preparation of (2S,3R,4S) N-Boc-2-Amino-1-cyclohexyl-3,4-dihydroxy-6-methylheptane

EXAMPLE 15A (4S,5R)-2,2-Dimethyl-4-(isobutyl-1-ene)-5-hydroxymethyl-1,3-dioxolane 2,3-O-Isopropylidene-D-erythrose was prepared by literature procedures (Cohen, N. et al, J. Am. Chem. Soc. 1983, 105, 3661) from D-isoascorbic acid. To a suspension of isopropyltriphenylphosphine (121 g, 2.4 equiv, 0.314 mol) in tetrahydrofuran (1.5 L) at −40° C. under nitrogen was added n-butyllithium (1.6M solution in hexanes) (197 mL, 2.4 equiv) dropwise. The erythrose (21 g, 1 equiv, 0.131 mol) in tetrahydrofuran (231 mL) ,was also added dropwise maintaining the temperature at −40° C. The mixture was then allowed to warm to room temperature and stirred under nitrogen for 20 hours and then quenched by the addition of ammonium chloride (77 g). The insoluble material was removed by filtration through Celite and the filtrate concentrated at reduced pressure to afford a residue which was extracted (4×) with ether. The combined ether extracts were wasted with water an brine, dried over magnesium sulfate, and concentrated in vacuo to afford a yellow oil. Chromatography on silica gel eluting with 20% ethyl acetate in hexanes afforded the title compound (13.0 g, 53%). $^1$H NMR (CDCl$_3$, 300 MHz) δ 1.4 (s, 3H), 1.50 (s, 3H), 1.73 (s, 3H), 1.78 (s, 3H), 3.57 (t of d, J=1.5 Hz, J=6 Hz, 2H), 4.20 (q, J=6 Hz, 8 Hz, 1H), 4.44 (q, J=9 Hz, 9 Hz, 1H), and 5.75 (d, J=9 Hz, 1H). MS (DCI/NH$_3$) m/e 204 (M+H+NH$_3$)$^+$.

EXAMPLE 15B (4S,5R)-2,2-Dimethyl-4-(isobutyl-1-ene)-5-(formyl-N-benzylimine)-1,3-dioxolane To oxalyl chloride (1.66 mL, 1.1 equiv) in methylene chloride (29 mL) cooled to −60 ° C. was added dimethyl sulfoxide (2.01 mL, 2.2 equiv) in methylene chloride (5.5 mL). After 2 minutes, a solution of the product Example 15A in methylene chloride (10 mL) was added. After stirring for 15 minutes at −60° C., triethylamine (8.23 mL, 5 equiv) was added. After stirring for an additional 5 minutes, the reaction mixture was allowed warm to room temperature. Water was added and the phases were separated. The aqueous phase was extracted chloroform (2×) and the combined organic extracts were washed with 1% hydrochloric acid and 5% sodium sulfite, dried over magnesium sulfate, and concentrated under reduced pressure to afford crude product. Chromatography on silica gel eluting with 10% ether in hexanes afforded the aldehyde (1.26 g, 57%). $^1$H NMR (CDCl$_3$, 300 MHz) δ 1.45 (s, 3H), 1.62 (s, 3H), 1.73 (s, 3H), 1.77 (s, 3H), 4.35 (m, 1H), 5.14 (m, 2H), 9.58 (d, J=6 Hz, 1H).

To the aldehyde (1.26 g, 6.84 mmol) dissolved in toluene (32 mL) was added magnesium sulfate (1.64 g, 2 equiv); the reaction mixture was then cooled to 0°-5° C. Benzylamine (746 μL, 1 equiv) was added and the reaction mixture was stirred at 0°-5° C. for 90 minutes and then concentrated at reduced pressure. Methylene chloride was added, insoluble material was removed by filtration, and the solvent was removed at reduced pressure to afford the title compound. $^1$H NMR (CDCl$_3$, 300 MHz) δ 1.42 (s, 3H), 1.57 (s, 3H), 1.63 (s, 3H), 1.68 (s, 3H), 4.53 (d,¯J=12 Hz, 1H), 4.62 (d, J=6 Hz, 1H), 4.70 (d, J=12 Hz, 1H), 5.05 (dd, J=9 Hz, 6 Hz, 1H), 5.15 (d, J=9 Hz, 1H), 7.20–7.37 (m, 5H), 7.64 (d, J=6 Hz, 1H).

EXAMPLE 15C (4S,5R)-2,2-Dimethyl-4-(isobutyl-1-ene)-5-[(1S)-1-benzylamino-2-cyclohexyl)ethyl-1,3-dioxolane Cerium(III) chloride heptahydrate (11 g, 5 equiv) was warmed at 150° C. under 0.15 mm of mercury vacuum for 2 hours with stirring. After cooling to room temperature, tetrahydrofuran (30 mL) was added. The mixture was stirred for 2 hours and then cooled to −40° C.

The Grignard reagent was prepared by the dropwise addition of cyclohexylmethyl bromide (4.12 mL, 30 mmol) dissolved in tetrahydrofuran (30 mL) to magnesium (717 mg, 30 mmol) and 1,2-dibromoethane (4–5 drops). After the reaction mixture had cooled to room temperature, it was cannulated into the cooled cerium-(III) chloride solution and stirred for 30 minutes. The reaction mixture was allowed to warm to room temperature, stirred for 2 hours, and cooled to −40° C.

A solution of the product of Example 15B (1.62 g, 5.90 mmol), 1 equiv.) in THF was cannulated into the cooled reaction mixture. The reaction mixture was allowed to warm to room temperature and stirred overnight. Then ether was added followed by saturated sodium bicarbonate solution. The organic layer was separated, dried over magnesium chloride, and concentrated under reduced pressure to afford crude compound (2.38 g, 100%). Chromatography on silica gel eluting with 20% ethyl acetate in hexane afforded the title product (368 mg, 17%). $^1$H NMR (CDCl$_3$, 300 MHz) δ 2.79 (t of d, J=3 Hz, 7.5 Hz, 1H), 3.45 (d, J=6 Hz, 2H), 3.86 (S,1H), 4.08 (d of d, J=6 Hz, 9 Hz, 1H), 4.76 (d of d, J=10.5 Hz, 6 Hz, 1H), 5.26 (d, J=10.5 Hz, 1H). MS (DCI/NH$_3$) m/e 372 (M+H)$^+$.

EXAMPLE 15D (2S,3R,4S) N-Boc-2-Amino-cyclohexyl-3,4-dihydroxy-6-methylheptane The product of Example 15C (39 mg, 0.105 mmol) was dissolved in acidic methanol, treated with palladium on carbon, and placed under 4 atmospheres of hydrogen for 24 hours. The catalyst was removed by filtration through Celite and the filtrate concentrated at reduced pressure to afford the amine salt (29 mg, 100%). MS (DCI/NH$_3$) m/e 228 (M+H)$^+$, 244 (M+H+NH$_3$)$^+$.

To the amine salt (14.1 mg, 0.058 mmol) dissolved in methylene chloride (1 mL) was added N-methylmorpholine (NMM) (164 μL, 2.5 equiv) followed by di-tert-butyl dicarbonate (15 mg, 1.2 equiv). The reaction mixture was stirred overnight and then washed with saturated sodium bicarbonate, dried over magnesium sulfate, and concentrated under reduced pressure to afford the title compound (15.3 mg, 77 %). $^1$H NMR (CDCl$_3$, 300 MHz) δ 0.89 (d, J=7 Hz, 3H), 0.95 (d, J=7 Hz, 3H), 1.45 (s, 9H), 1.94 (m, 1H), 3.20 (d, J=8 Hz, 1H), 3.34 (m, 1H), 4.04 (br m, 2H), 4.25 (bd, 1H), 4.55 (bd, 1H).

EXAMPLE 16

Alternative Preparation of (2S,3R,4S) N-Boc-2-Amino-1-cyclohexyl-3,4-dihydroxy-6-methylheptane

EXAMPLE 16A (2S,3R)-3-(1-Methoxy-1-methyl)ethoxy-1,2-epoxy-4-pentene

To (2S,3R)-1,1-Epoxypent-4-en-3-ol (Schreiber, S. L.; Schreiber, T. S.; Smith, D. B. ; J. Amer. Chem. Soc., 1987, 109, 1525) (4.0 g, 40 mmol) and 2-methoxypropene (10 equivalents) dissolved in dichloromethane (50 mL) and cooled in an ice-water bath is added pyridinium p-toluenesulfonate (0.1 equivalents). The reaction mixture is stirred at room temperature for 24 hours and quenched with saturated sodium bicarbonate solution.

The organic layer is separated, dried over magnesium sulfate and the solvent removed by distillation. Vacuum distillation affords the title product.

EXAMPLE 16B (4S,5R)-2,2-Dimethyl-4-isobutyl-5-vinyl-1-3-dioxolane

Isopropylmagnesium chloride (2M in diethyl ether) (10 mL, 20 mmol) is added to a mixture of cuprous iodide (418 mg, 2.2 mmol) in anhydrous tetrahydrofuran cooled to −70° C. The mixture is stirred for 20 minutes and a solution of the product of Example 16A (14 mmol) in anhydrous tetrahydrofuran (10 mL) is added. After stirring for 2 hours, the reaction mixture is poured into saturated aqueous ammonium chloride. The solution is extracted with ethyl acetate, and the combined organic extracts dried over magnesium sulfate and concentrated under reduced pressure to give the addition product.

To the crude alcohol dissolved in dichloromethane is added camphorsulfonic acid (500 mg). The reaction is stirred at room temperature for 24 hours and poured into saturated sodium bicarbonate solution. The organic solvents are separated, dried over magnesium sulfate and concentrated by distillation to give the title compound.

EXAMPLE 16C (4S,5R)-2,2-Dimethyl-4-isobutyl-5-formyl-1,3-dioxolane

A dichloromethane solution of the product of Example 16B (1 g) is cooled to −78° C. and a stream of ozone is passed through the solution until a blue color persists. Excess ozone is removed with nitrogen ebullition and dimethyl sulfide (1 mL) is added. The reaction is allowed to warm to room temperature and stirred overnight. The solvents are removed under reduced pressure, and the title compound is obtained following purification by silica gel chromatography.

EXAMPLE 16D (2S,3R,4S) N-Boc-2-Amino-1-cyclohexyl-3,4-dihydroxy-6-methylheptane The product of Example 16C can be treated sequentially with benzylamine and cyclohexylmethyl Grignard and then N-protected according the procedures disclosed in Examples 15B, 15C and 15D, respectively, to provide the desired product.

EXAMPLE 17

Preparation of Salts of (2S)-2-Benzyl-3-(1-methyl-piperazin-4-ylsulfonyl)propionyl-(L)-(4-Thiazolyl)Ala Amide of (2S,3R,4S)-2-Amino-1-cyclohexyl-3,4-dihydroxy-6-methylheptane

EXAMPLE 17A (2S)-2-Benzyl-3-(1-methyl-piperazin-4-ylsulfonyl)propionyl-(L)-(4-Thiazolyl)Ala Amide of (2S,3R,4S)-2-Amino-1-cyclohexyl-3,4-dihydroxy-6-methylheptane hydrochloride salt Acetyl chloride (3.27 g, 41.65 mmol) was added to ethanol (150 ml) at 5° C. The mixture was stirred for two hours at 5° C. and added to a suspension of the product of Example 1R (30 g, 42.5 mmol) in ethanol (150 ml) at 5° C. After 2 hours, the mixture was filtered and the solvent removed under vacuum. The residue was dissolved in methylene chloride (300 ml) and the desired product was precipitated by the addition of either 3:1 heptane/ethyl acetate (1500 ml) or diethyl ether (1500 ml) or methyl t-butyl ether (1500 ml). Anal calcd for $C_{35}H_{56}N_5O_6S_2Cl.0.5\ H_2O$: C, 55.94; H, 7.65; N, 9.32; Cl, 4.72; S,8.53. Found: C, 56.06; H, 7.58; N, 9.30; Cl, 4.95; S, 8.17.

EXAMPLE 17B (2S)-2-Benzyl-3-(1-methyl-piperazin-4-ylsulfonyl)propionyl-(L)-(4-Thiazolyl)Ala Amide of (2S,3R,4S)-2-Amino-1-cyclohexyl-3,4-dihydroxy-6-methylheptane methanesulfonate salt Methanesulfonic acid (0.264 g, 2.74 mmol) was added to a suspension of the product of Example 1R (2.0 g, 2.84 mmol) in methylene chloride (20 ml). The mixture was stirred for 3 hours and filtered. The desired produce was precipitated by the addition of either 3:1 heptane/ethyl acetate (100 ml) or diethyl ether (100 ml) or methyl t-butyl ether. Anal calcd for $C_{36}H_{59}N_5O_9S_3.0.5\ H_2O$: C, 3.31; H, 7.46; N, 8.63; S, 11.86. Found: C, 53.32; H, 7.49; N, 8.54; S,11.91.

EXAMPLE 17C (2S)-2-Benzyl-3-(1-methylpiperazin-4-ylsulfonyl)propionyl-L-{4-Thiazolyl)Ala Amide of (2S,3R,4S)-2-Amino-1-cyclohexyl-3,4-dihydroxy-6-methylheptane Dihydrochloride Salt The resulting compound from Example 1R (200.4 mg, 0.284 mmol) was dissolved in ethanol (5 mL) with warming. After the solution had cooled to room temperature, it was treated with 4.8M hydrochloric acid in dioxane (175 μL, 0.84 mmol). After standing for 15 minutes, the reaction mixture was concentrated under reduced pressure to afford the title compound as a white solid (226.7 mg, 99.8%). Anal calcd for $C_{35}H_{57}N_5O_6S_2Cl_2$: C, 53.97; N, 7.38; N, 8.99; Cl, 9.10. Found: C, 53.04; H, 7.28; N, 8.80; Cl, 8.81.

EXAMPLE 17D (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Phosphoric acid Salt To the compound resulting from Example 1R (999 mg, 1.415 mmol) dissolved in hot ethanol (25 mL) and cooled to room temperature was added 0.694M phosphoric acid (2.00 mL, 1.39 mmol). The reaction mixture was concentrated in vacuo to afford an amorphous solid which was triturated with ether to afford the title compound as a white solid (1.0299 g, 91%). Anal calcd for $C_{35}H_{58}N_5O_{10}S_2P.0.75\ H_2O$: C, 51.42; H, 7.34; N, 8.57; S, 7.84; P, 3.79. Found: C, 51.77; H, 7.21; N, 8.55; S, 7.44; P, 3.26.

EXAMPLE 17E (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Citric acid Salt The compound resulting from Example 1R (2.0616 g, 2.92 mmol) was taken up in ethanol (25 mL) and placed in a 75° C. bath until dissolved. After dissolution, the reaction mixture was placed in an ice bath and cooled until the internal temperature was 10° C. Then citric acid (550.3 mg, 2.864 mmol) was added, the cooling bath was removed, and the mixture was stirred at room temperature for 30 minutes and then concentrated under reduced pressure to give a residue. The residue was washed with ether and then triturated with ether and stirred to afford the title compound as a white solid (2.0709 g, 79%). Anal calcd for $C_{41}H_{63}N_5O_{13}S_2 \cdot 1.4$ $H_2O$: C, 53.33; H, 7.18; N, 7.58; S, 6.95. Found: C, 53.66; H, 7.16; N, 7.49; S, 6.56.

EXAMPLE 17E (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Sodium Dihydrogen Citrate Salt To the compound resulting from Example 1R (1.5962 g, 2.261 mmol) dissolved in ethanol (25 mL) at 80° C. and cooled to room temperature was added citric acid monosodium salt (475 mg, 2.219 mmol). After stirring for 15 minutes, water (5 mL) was added. The reaction mixture was warmed at 50° C. for 15 minutes and additional water was added (2.5 mL followed by 1mL). After stirring at 50° C. an additional 15 minutes, the reaction mixture was concentrated under reduced pressure. The residue obtained was washed with ether (3×) and then ether (80 mL) was added and the mixture was stirred overnight to afford the title product as a white solid (1.55 g, 75%). Anal calcd for $C_{41}H_{62}N_5O_{13}S_2 \cdot Na \cdot 0.5 H_2O$: C, 53.00; H, 6.83; N, 7.54; Na, 2.47. Found: C, 52.61; H, 6.75; N, 7.32; Na, 2.42.

EXAMPLE 17G (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Potassium Dihydrogen Citrate Salt To the compound resulting from Example 1R (1.0345 g, 1.456 mmol) dissolved in hot ethanol (25 mL) and cooled to room temperature was added citric acid (282 mg, 1.468 mmol). After the citric acid had dissolved, 0.733M potassium hydroxide (2.00 mL, 1.47 mmol) was added followed by water (6 mL). The reaction mixture was stirred until clear and then concentrated under reduced pressure to afford a residue. The residue was triturated with ether to give the title compound as a white solid (1.1716 g, 85%). Anal calcd for $C_{41}H_{62}N_5O_{13}S_2K$: C, 52.60; H, 6.68; N, 7.48; K, 4.18. Found: C, 51.47; H, 6.58; N, 7.09; K, 4.67.

EXAMPLE 17H (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Choline Dihydrogen Citrate Salt The compound resulting from Example 1R (917 mg, 1.299 mmol) in ethanol (25 mL) was warmed at 80° C. until dissolved and then cooled to room temperature. Choline dihydrogen citrate (376 mg, 1.273 mmol) was added, and the reaction mixture was stirred for 15 minutes. Water (2 mL) was added, and when the solution became clear, it was concentrated under reduced pressure to afford a white solid. This solid was triturated with ether and filtered to afford the title product as a white powder (1.1915 g, 92%). Anal calcd for $C_{46}H_{76}N_6O_{14}S_2$: C, 55.18; H, 7.65; N, 8.39. Found: C, 55.37; H, 7.69; N, 8.38.

EXAMPLE 17I (2S)-2-Benzyl-3-(1-methylpiperazin-4-yl sulfonyl)propionyl-L-(4-Thiazolyl)Ala Amide of (2S,3R,4S)-2-Amino-1-cyclohexyl-3,4-dihydroxy-6-methylheptane Trizma Citrate Salt The compound resulting from Example 1R (763.8 mg, 1.082 mmol) was dissolved in ethanol (25 mL) with warming to 70° C. and was cooled to room temperature. Citric acid (207.8 mg, 1.082 mmol) was added and the reaction mixture was stirred for 15 minutes. Trizma (Tris[hydroxymethyl]aminomethane) (130.5 mg, 1.077 mmol) was added and the reaction mixture was stirred an additional 15 minutes. Water was added (2.5 mL) and after stirring for 15 minutes, a clear solution resulted. Concentration under reduced pressure afforded a residue which was taken up in ethanol (20 mL), warmed slightly to effect dissolution, and concentrated under reduced pressure to afford a residue which was triturated with ether to give the title product as a white solid (872.2 mg, 79%). Anal calcd for $C_{45}H_{74}N_6O_{16}S_2 \cdot 1.0 H_2O$: C, 52.11; H, 7.38; N, 8.10; S, 6.18. Found: C, 52.31; H, 7.31; N, 8.00; S, 5.80.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthaienesulfonate, oxalate, pamoate, pectinate, persulfate, phosphate, 3-phenylpropionate, picrate, pivalate, propionate, succinate, tartrate, thiocyanate, rosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of formula (I) which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The prodrugs are metabolically converted in vivo to the parent compound of formula (I). The preparation of the prodrug esters is carried out by reacting a hydroxyl-substituted compound of formula (I) with an activated amino acyl, phosphoryl or hemisuccinyl derivative. The resulting product is then deprotected to provide the desired prodrug ester. Other prodrugs include a hydroxyl-substituted compound of formula I wherein the hydroxyl group is functionalized with a substituent of the formula —CH($R_{20}$)OC(O)$R_{21}$ or —CH($R_{20}$)OC(S)$R_{21}$ wherein $R_{21}$ is loweralkyl, haloalkyl, alkoxy, thioalkoxy or haloalkoxy and $R_{20}$ is hydrogen, loweralkyl, haloalkyl, alkoxycarbonyl, aminocarbonyl, alkylaminocarbonyl or dialkylaminocarbonyl. These prodrugs can be prepared by condensation of the hydroxyl group with an activated aldehyde followed by acylation of the intermediate hemiacetal.

The novel compounds of the present invention possess an excellent degree of activity and specificity in treating hypertension in a human or other mammal. The novel compounds of the present invention are also useful for treating congestive heart failure in a human or other mammal. The present invention also relates to the use of the novel compounds of the invention for treating vascular abnormalities in a human or other mammal, especially those vascular diseases associated with diabetes, such as diabetic nephropathy, diabetic neuropathy and diabetic retinopathy. The compounds of the invention are also useful for the treatment of renal diseases in a human or other mammal, in particular acute and chronic renal failure. The compounds of the invention are also useful for the treatment of psoriasis in a human or other mammal.

The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C. and pH of 6.5. At the end of the incubation, the amount of angiotensin I formed is measured by radioimmunoassay and the molar concentration required to cause 50% inhibition, expressed as the $IC_{50}$ is calculated. When tested in accordance with the foregoing procedure, the compounds of the invention were found to inhibit renin with $IC_{50}$'s as shown in Table I.

TABLE I

| Example | $IC_{50}$ (nM) |
| --- | --- |
| 1R | 0.24 |
| 6D | 0.33 |
| 10B | 0.30 |
| 11F | 0.28 |
| 12F | 0.45 |
| 13C | 0.22 |

The ability of the compounds of the invention to reduce blood pressure can be demonstrated in vivo. Male beagle dogs (8–12 kg, Marshall/Hazelton) were converted to a salt-depleted status by dosing on the three consecutive days prior to the experiment with furosemide (Phoenix Pharmaceuticals, 10 mg/kg i.m.) and by placing them on a low sodium diet (approximately 2–5 meq/day; H/D; Hills Pet Products). Prior to the study, each dog was instrumented with an indwelling catheter ana conditioned to stand calmly in a restraining sling for periods of up to 8 hours. On the morning of the experiment, the arterial catheter was connected to a Sorenson Transpac II ® pressure transducer (Abbott Laboratories). For dogs receiving intravenous (i.v.) doses, a catheter (Abbott; 16 ga Venocath) was introduced in a rear leg saphenous vein by venipuncture. For dogs receiving receiving oral (p.o.) doses by garage, an 18 Fr. suction catheter (Mallinckrodt Critical Care) was used. Data samples of systemic hemodynamic variables were acquired by the MI2 computer at 5 minute intervals beginning 90 minutes prior to administration of the test compound and ending 6 hours after dosing. Arterial blood smaples (3.0 ml) to determine plasma drug concentrations and plasma renin activity (PRA) were taken for i.v. doses at −60, −30, 3, 10, 30, 60, 120, 240 and 360 minutes an for p.o. doses at −60, −30, 15, 30, 60, 90, 120, 180 and 360 minutes relative to the time of test compound administration.

Figure 1B:
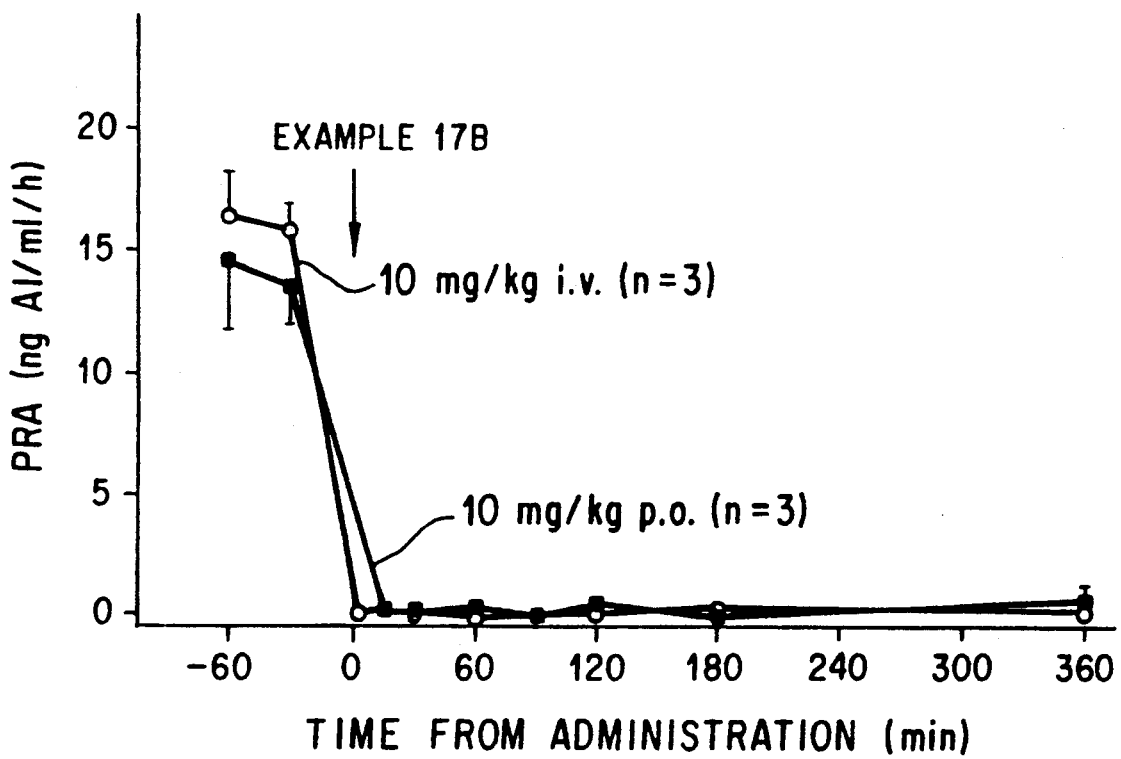

FIGS. 1A and 1B show the results in terms of mean arterial pressure (MAP, in mm Hg) and plasma renin activity respectively following administration of the compound of Example 17B (monomethanesulfonate). The compound of Example 17B was administered i.v. at a dose of 10 mg/kg as a solution (10 mg/ml) in 5% dextrose in water (D5W). The compound of Example 17B was also administered p.o. at a dose of 10 mg/kg as a solution in methylcellulose. Three dogs were studied for each route of administration. The results demonstrate that the compound inhibits renin in vivo and is effective for reducing blood pressure.

Total daily dose of a compound of the invention administered to a human or other mammal in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

A typical tablet dosage form comprises the active ingredient (no more than 35% by weight of the tablet, citric acid (5-15% by weight of the tablet), a filler such as microcrystalline cellulose (for example, Avicel® PH101), a disintegrant (8-12% by weight of the tablet, for example, crospovidone) and a lubricant (0.5-1.5% by weight of the tablet, for example, magnesium stearate). A tablet can also comprise one or more surfactants (for example, Tween 80, Brij®35, Emulphor 719 and the like), with the total amount of surfactants being 2-3% by weight of the tablet.

The tablet dosage form is prepared by blending the active ingredient, 50% of the citric acid and the Avicel®. Ethanol (200 proof) is added and the mixture is granulated. If surfactants are included, they are added as a solution in the ethanol during the granulation step. The granules are dried overnight and screened through a 14 mesh screen. The remaining 50% of the citric acid, the crospovidone and the magnesium stearate are blended with the granules and then compressed into tablets. The composition of two typical tablet dosage forms (containing 100 mg of active ingredient) is shown below

| Ingredient | Amount Per Tablet | |
|---|---|---|
| | mg | % |
| Tablet Composition A | | |
| compound of Example 17A | 107.2 | 30.6 |
| citric acid | 50.1 | 14.3 |
| Avicel ® PH101 | 150.0 | 42.8 |
| crospovidone | 40.0 | 11.4 |
| magnesium stearate | 3.0 | 0.9 |
| Tablet Composition B | | |
| compound of Example 17A | 107.2 | 30.3 |
| citric acid | 49.9 | 14.1 |
| Avicel ® PH101 | 150.7 | 42.6 |
| Brij ® 35 | 2.5 | 0.7 |
| Tween 80 | 0.7 | 0.2 |
| crospovidone | 40.0 | 11.3 |
| magnesium stearate | 2.8 | 0.8 |

A typical capsule dosage form comprises a soft elastic capsule filled with a solution comprising the active ingredient dissolved in a solvent comprising a mixture of PEG 400 (98% volume/volume) and glycerin (2% volume/volume).

A typical soft comprising gelatin capsule has a composition comprising gelatin NF (38.3% by weight), glycerin (96% active; 29% by weight) and water (32.7%).

The capsule dosage form is prepared by mixing appropriate volumes of PEG 400 and glycerin to give a mixture which is 98% by volume PEG 400 and 2% by volume glycerin. Nitrogen is bubbled through the mixture for several hours. While maintaining the mixture under a nitrogen atmosphere, the mixture is heated to about 40° C. and then the desired amount of the active ingredient is dissolved. The solution of active ingredient is then filled into soft elastic gelatin capsules. The filling operation is conducted under a nitrogen atmosphere.

Using the method described above, soft elastic gelatin capsules can be prepared which contain 0.1 ml of a PEG 400/glycerin (985/2% by volume)solution of the compound of Example 17A at concentrations of 0.7 mg/ml, 7 mg/ml and 21 mg/ml.

Liquid dosage forms or oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use to novel compounds, pharmaceutical compositions containing the novel compounds and the use of the compounds and compositions to inhibit renin for treating glaucoma or reducing and/or controlling intraocular pressure. The present invention also relates to the use of novel compounds and pharmaceutical compositions which inhibit renin in combination with a beta-adrenergic antagonist agent or an angiotensin converting enzyme inhibiting compound for treating glaucoma or reducing and/or controlling intraocular pressure.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta-adrenergic antagonist agent in a suitable pharmaceutical vehicle or an angiotensin converting enzyme inhibiting compound in a suitable pharmaceutical vehicle.

The compositions of the invention are administered as topical or systemic pharmaceutical compositions when used for treating or reducing and/or controlling intraocular pressure.

These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboxymethyl cellulose salts, hydroxyethyl cellulose, hydroxypropyl cellulose;

acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvlnyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration.

The term "controlling intraocular pressure" as use herein means the regulation, attenuation and modulation of increased intraocular tension. The term also means that the decrease, in the otherwise elevated intraocular pressure, obtained by the methods and compositions of the invention is maintained for a significant period of the as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta-adrenergic antagonist compounds.

The term "beta-adrenergic antagonist" as used herein means a compound which by binding to beta-adrenergic plasma membrane receptors reduces or eliminates sympathetic activity or blocks the effects of exogenously adminstered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

Timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:
Renin inhibitor: 1 ng to 0.1 mg
Beta-adrenergic antagonist: 5 ug to 125 ug When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme (ACE) inhibiting compound. Examples of angiotensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 ug of the compositon of the invention. The preferred ranges of the components in the composition of the invention in unit dosage form are:
Renin inhibitor: 1 ng to 0.1 mg
ACE inhibitor: 5 ng to 50 ug When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response or the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasone, methylprednisolone, triamcinolone, betamethasone, alclometasone, flunisotide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectable dosage form of a steroidal antiinflammatory agent and a topical or oral dosage form of the novel renin inhibitor may be used. A preferred combination comprises a topical steroidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 25 ng. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 ug to about 600 ug. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The effect on intraocular pressure of the novel compounds of the invention can be determined in rabbits by using the following method.

Effects of Topically Administered Renin Inhibiting Compounds on Intraocular Pressure of Rabbits a. Method The antiglaucoma activity of the compounds was tested by measuring the effect on intraocular pressure in rabbits as described by Tinjum, A. M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards.

The ability of a compound of the invention to treat vascular diseases, especially those associated with diabetes, can be demonstrated by comparing urinary protein excretion in control diabetic Wistar rats with urinary protein excretion in diabetic Wistar rats treated with a compound of the invention. Wistar rats are made diabetic by streptozocin treatment.

The ability of a compound of the invention to treat psoriasis can be demonstrated using the methods outlined in Hofbauer, et al., Br. J. Dermatol. 118 85 (1988); Lowe, et al., Arch. Dermatol. 117 394 (1981); and Du Vivier, et al., J. Invest. Dermatol. 65 235 (1975).

The effect of a compound of the invention on renal failure can be demonstrated by observing the effects on renal henodynamics that ultimately can alter glomerular filtration rate (GFR) when a compound of the invention is administered to an animal in which acute renal failure has been modeled. Acute renal failure can be modeled by ischemia, ureteral obstruction or nephrotoxic agents such as gentamicin, cis-platin and the like. In addition, the effect of a compound of the invention on chronic renal failure can be demonstrated by observing the effects on proteinuria, hitopathologic improvement and long term stabilization of GFR when a compound of the invention has been administered to an animal in which chronic renal failure has been modeled. Chronic renal failure can be modeled by reduced renal mass, puromycin-induced nephrosis or diabetic nephropathy.

The present invention is also directed to the use of a compound of the formula I in combination with one or more cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors and other agents useful for treating (in a human or other mammal) hypertension, congestive heart failure, vascular diseases related to diabetes or for treating renal diseases such as acute or chronic renal failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula I and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula I to inhibit retroviral proteases and in particular to inhibit HIV-1 protease and HIV-2 protease. Compounds of formula I are useful for treatment or prophylaxis (in a human or other mammal) of diseases caused by retroviruses, especially acquired immune deficiency syndrome or an HIV infection.

The inhibitory potency of the compound of the invention against HIV protease can be determined by the following method.

Fluorogenic Assay for Screening Inhibitors of HIV Protease

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 uM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmission 490 nM) is recorded as a function of time. The reaction rate is determined for the first six to eight minutes. The observed rate is directly proportional to the moles of substrate cleaved per unit time. The percent inhibition is $100 \times (1 - (\text{rate in presence of inhibitor})/(\text{rate in absence of inhibitor}))$.

Fluorogenic substrate: Dabcyl-Ser-Gln-Asp-Tyr-Pro-Ile-Val-Gln-EDANS wherein DABCYL=4-(4-dimethylaminophenyl)azobenzoic acid and EDANS=5-((2-aminoethyl)amino)naphthalene-1-sulfonic acid.

The antiviral activity of compound of the invention can be demonstrated using the following method.

A mixture of 0.1 ml ($4 \times 10^6$ cells/ml) of H9 cells and 0.1 ml (100 infectious units) of HIV-1$_{3B}$ is incubated on a shaker for 2 h. The resulting culture is washed three times, resuspended into 2 ml of medium, and treated with 10 μl of the compound of the invention (5 mM in dimethylsulfoxide). The control culture is treated in an identical manner except the last step was omitted. After incubation of the culture for eight days without change of medium, an aliquot (0.1 ml) of the supernatent is withdrawn and incubated with fresh H9 cells on a shaker for 2 h. The resulting culture is washed three times, resuspended into 2 ml of medium, and incubated. Virus infectivity is determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for treating glaucoma or reducing and/or controlling intraocular pressure comprising administering to a mammal in need of such treatment a therapeutically effective amount of a compound of the formula:

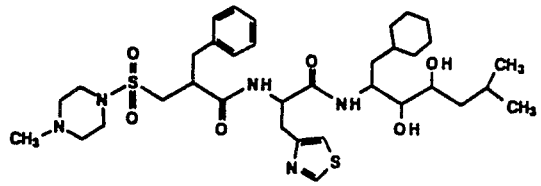

or a pharmaceutically acceptable salt or ester thereof.

2. A method for treating glaucoma or reducing and/or controlling intraocular pressure comprising administering to a mammal in need of such treatment a therapeutically effective amount of the compound (2S)-2-Benzyl-3-(1-methyl-piperazin-4-ylsulfonyl)propionyl-(L)-(4-Thiazolyl)Ala Amide of (2S,3R,4S)-2-Amino-1-cyclohexyl-3,4-dihydroxy-6-methylheptane; or a pharmaceutically acceptable salt or ester thereof.

3. The method of claim 2 wherein the compound is (2S)-2-Benzyl-3-(1-methyl-piperazin-4-ylsulfonyl)propionyl-(L)-(4-(Thiazolyl)Ala Amide of (2S,3R,4S)-2-Amino-1-cyclohexyl-3,4-dihydroxy-6-methylheptane hydrochloride.

4. A topical ocular pharmaceutical composition for treating glaucoma or reducing and/or controlling intraocular pressure comprising an ophthalmologically acceptable pharmaceutical carrier and a therapeutically effective amount of a compound of the formula:

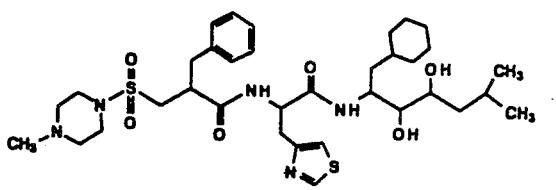

or a pharmaceutically acceptable salt or ester thereof.

5. A topical ocular pharmaceutical composition for treating glaucoma or reducing and/or controlling intraocular pressure comprising an ophthalmologically acceptable pharmaceutical carrier and a therapeutically effective amount of the compound (2S)-2-Benzyl-3-(1-methyl-piperazin-4-ylsulfonyl)propionyl-(L)-(4-Thiazolyl)Ala Amide of (2S,3R,4S)-2-Amino-1-cyclohexyl-3,4-dihydroxy-6-methylheptane; or a pharmaceutically acceptable salt or ester thereof.

6. The composition of claim 5 wherein the compound is (2S)-2-Benzyl-3-(1-methyl-piperazin-4-ylsulfonyl)-propionyl-(L)-(4-Thiazolyl)Ala Amide of (2S,3R,4S)-2-Amino-1-cyclohexyl-3,4-dihydroxy-6-methylheptane hydrochloride.

* * * * *